US012769354B1

(12) United States Patent
Diebo

(10) Patent No.: US 12,769,354 B1
(45) Date of Patent: Oct. 20, 2026

(54) HARDWARE-INTERLOCKED ROBOTIC SYSTEM FOR PHYSICS-GATED MANUFACTURE OF PATIENT-SPECIFIC SPINAL FIXATION RODS

(71) Applicant: Bassel G. Diebo, Providence, RI (US)

(72) Inventor: Bassel G. Diebo, Providence, RI (US)

( * ) Notice: Subject to any disclaimer, the term of this patent is extended or adjusted under 35 U.S.C. 154(b) by 0 days.

(21) Appl. No.: 19/410,974

(22) Filed: Dec. 5, 2025

Related U.S. Application Data

(60) Provisional application No. 63/789,795, filed on Apr. 16, 2025.

(51) Int. Cl.

| | |
|---|---|
| ***G06C 25/00*** | (2006.01) |
| ***G06F 30/10*** | (2020.01) |
| ***G06F 30/27*** | (2020.01) |
| ***H04L 9/08*** | (2006.01) |
| *A61B 17/70* | (2006.01) |
| *A61B 34/10* | (2016.01) |

(52) U.S. Cl.
CPC ............. *G06C 25/00* (2013.01); *G06F 30/10* (2020.01); *G06F 30/27* (2020.01); *H04L 9/0861* (2013.01); *A61B 17/7062* (2013.01); *A61B 2034/104* (2016.02); *A61B 2034/108* (2016.02)

(58) Field of Classification Search
CPC ...... G06F 21/12; G06F 21/121; G06F 21/123; G06F 21/125; G06F 21/126; G06F 21/128; G06F 30/27; G06F 30/10; G06C 25/00–25/02; H04L 9/0861; A61B 17/7062; A61B 2034/104; A61B 2034/108
See application file for complete search history.

(56) References Cited

U.S. PATENT DOCUMENTS

| | | | | |
|---|---|---|---|---|
| 2018/0046949 | A1 | 2/2018 | Kahn et al. | |
| 2019/0209080 | A1 * | 7/2019 | Gullotti | A61B 17/7035 |
| 2022/0160428 | A1 * | 5/2022 | Murray | A61B 34/10 |
| 2024/0138991 | A1 | 5/2024 | Hussain et al. | |
| 2024/0325054 | A1 | 10/2024 | Bedor | |
| 2025/0327320 | A1 * | 10/2025 | Heep | B21D 11/12 |

OTHER PUBLICATIONS

Yasmin et al., "Performance Analysis of Lightweight Algorithm GIFT-COFB for 3-D Printer Security", Publication Year: 2022, Publisher: IEEE, 2022 8th International Conference on Signal Processing and Communication (ICSC), pp. 468-474.*
International Search Report and Written Opinion for International Application No. PCT/US2025/058428 mailed Mar. 27, 2026.

* cited by examiner

*Primary Examiner* — Rehana Perveen
*Assistant Examiner* — John P Hocker
(74) *Attorney, Agent, or Firm* — Adler Pollock & Sheehan P.C.

(57) ABSTRACT

A hardware-interlocked manufacturing system for patient-specific spinal rods comprises (i) a computing platform executing biomechanical simulation and physics-constrained generative AI to produce a candidate rod geometry, and (ii) a manufacturing controller that maintains a locked state by electrically isolating the actuation motors of a physical rod-fabrication device via a safety relay (ISO 13849-1 Cat 4/PL e). The locked state persists until the computing platform verifies biomechanical convergence and issues a cryptographically signed convergence token derived from the stress tensor field, whereupon the relay closes, and fabrication is enabled. The system prevents fabrication of any geometry lacking physics-based validation, even in the presence of manual override commands.

7 Claims, 12 Drawing Sheets

HARDWARE-INTERLOCKED ROBOTIC SYSTEM FOR PHYSICS-GATED MANUFACTURE OF PATIENT-SPECIFIC SPINAL FIXATION RODS

CROSS REFERENCE TO RELATED APPLICATIONS

This application claims the benefit of priority to United States (U.S.) Provisional Application Ser. No. 63/789,795, filed 16 Apr. 2025, the entire disclosure of which is incorporated by reference as if fully set forth herein in its entirety.

FIELD OF THE INVENTION

The present disclosure relates to methods for using a trained neural network to form a spinal fixation rod for correcting spinal deformities.

BACKGROUND

Surgical treatment of spinal disorders has evolved substantially over the past two centuries. In the early 1800s, operative interventions on the spine were rare and largely limited to drainage of abscesses or treatment of traumatic wounds, performed in an era before modern anesthesia and antisepsis. Surgeons approached the spine with extreme caution because of high rates of infection, blood loss, and neurologic injury, and most deformities or degenerative conditions were managed non-operatively with bedrest, corsets, and rudimentary braces.

By the late 19th century, advances in anesthesia and aseptic technique enabled more deliberate operations on the vertebral column. Early laminectomies were performed to relieve spinal cord compression from tumors, trauma, or deformity, although these procedures often resulted in destabilization of the spine. The introduction of radiography allowed surgeons to visualize spinal alignment and pathology for the first time, but the dominant paradigm for structural disorders remained external immobilization rather than internal stabilization.

In the early 20th century, the concept of spinal fusion began to take hold, particularly for conditions such as Pott disease, scoliosis, and post-traumatic instability. Surgeons developed posterior fusion techniques using bone grafts to achieve segmental arthrodesis, frequently without metallic implants. Early spinal fusions were long and rigid, often requiring prolonged postoperative casting. While these approaches could achieve some degree of stability, correction of complex deformities was limited, and nonunion or progressive deformity remained common problems.

Mid-century developments brought the first widely adopted spinal instrumentation systems. The introduction of distraction rods and hooks for scoliosis correction marked a major shift from purely biological fusion to combined fusion and internal fixation. These constructs allowed surgeons to obtain greater coronal plane correction and earlier mobilization, but they were largely non-segmental and focused on straightening the spine rather than restoring physiological sagittal alignment. At the same time, improvements in anesthesia, blood transfusion practices, and perioperative antibiotics reduced the morbidity of long spinal procedures and broadened the range of patients who could be offered surgery.

From the 1970s through roughly 2000, spinal surgery entered an era of increasingly sophisticated fixation concepts. Segmental instrumentation with sublaminar wiring and multi-hook constructs enabled more controlled correction and distribution of forces across multiple vertebral levels. Pedicle screw fixation was introduced and gradually adopted as surgeons recognized its capacity for three-column control of the vertebra, improved pullout strength, and powerful corrective maneuvers. Crosslinks, rods of different diameters, and various implant configurations were explored to balance stability with flexibility. Concurrently, computed tomography and early magnetic resonance imaging improved preoperative assessment of bony and neural structures, enhancing surgical planning and decompression strategies.

Despite these advances, by the beginning of the 21$^{st}$ century surgeons continued to face recurrent challenges: variability in deformity correction between patients, uncertainty in selecting optimal rod contours and construct configurations, and the risk of complications such as junctional failure, implant loosening, or rod breakage. These limitations reflected the fact that, historically, rod design and construct selection were based largely on the surgeon's experience, template-based planning, and static imaging, rather than on detailed, patient-specific biomechanical analysis or predictive modeling. What is urgently needed is implementation of new technology.

BRIEF SUMMARY OF THE INVENTION

For purposes of summary, certain aspects, advantages, and novel features are described herein. It is to be understood that not necessarily all such advantages may be achieved in accordance with any one particular embodiment. Thus, the apparatuses or methods claimed may be embodied or carried out in a manner that achieves or optimizes one advantage or group of advantages as taught herein without necessarily achieving other advantages as may be taught or suggested herein.

In an embodiment, a method for forming a spinal rod is disclosed where the method may use a trained network to create a spinal fixation rod for correcting spinal deformities. The process can involve training a neural network with anatomical parameters such as pelvic incidence, pelvic tilt, thoracic kyphosis, vertebral pelvic angles, distances from femoral head to S1 endplate, segment distances, vertebral center positions, and vertebral endplate orientations. The trained network may generate estimated pelvic orientation and shape, a spline based on various parameters, estimated vertebrae positions along the spline, estimated angulation between the spline and endplates, and an ideal full spine shape, which can be used to form the spinal fixation rod.

The method can further define the relationship between pelvic incidence and vertebral pelvic angle using a regression method where $R^2$ is at least 0.9. Accordingly, the method may include defining thoracic kyphosis and the relationship between pelvic incidence and vertebral pelvic angle using regression methods, with $R^2$ being at least 0.9.

In another embodiment, a method for forming a spinal rod may involve obtaining data representing a patient's spinal parameters, inputting the data into a trained neural network, generating an ideal spine shape, and forming a spinal rod based on the ideal shape. In one working embodiment, the neural network is a 6-layer transformer with 512-dimensional embeddings trained on 8,147 postoperative cases, achieving $R^2 \geq 0.92$ for predicted sagittal alignment and $\geq 0.89$ for thoracic kyphosis In other embodiments, historical data used to train the neural network may include intervertebral heights, vertebral body heights, intervertebral and vertebral angulation, segmental alignment, and distances between implanted rods and vertebral bodies.

The method can further model the ideal spine shape using a gravity line biomechanical model to predict changes above fused segments and pelvic position.

The ideal spine shape may also account for posterior translation of the spinal rod from the patient's spine and consider thoracolumbar and cervical alignment to maintain proper head position and horizontal gaze.

In some embodiments, the rods may extend from vertebra T1 to the pelvis. In other embodiments, the rods can extend from vertebra C2 to T1.

The method may optimize spinal rod contours using a finite element model to predict complications at junctions between fused and unfused vertebrae, minimizing the likelihood of the occurrence of proximal junctional kyphosis and failure. The finite element model may also be used to predict the impact of rod stiffness, fixation techniques, and ideal shape on adjacent segment loading as well as the influence of different spinal rod materials on adjacent segment biomechanics. The finite element model may predict the effects of hybrid spinal rods on biomechanics to optimize load distribution and minimize abrupt angulation transitions, and account for the effects of patient soft tissue interactions with rods over time on the biomechanics.

Further, the finite element model may predict spinal rod fatigue-related failure at junctional zones.

A spinal rod may be formed using the methods described. Such a spinal rod can have regions corresponding to the patient's segment distances between specific vertebrae, and wherein the regions may be visually indicated on the spinal rod. Additionally, angulation inflection points can be visually indicated on the spinal rod.

Conventional methods for producing spinal fixation devices have typically relied on creating patient-specific geometries through medical imaging followed by manual adjustment of standard implant templates using computer-aided design (CAD) tools. Once a candidate geometry is finalized, the design is exported to a fabrication device—such as a three-dimensional (3D) printer or computer numerical control (CNC) mill—without further computational assessment of biomechanical performance. In these workflows, the role of simulation is limited to off-line validation studies rather than being integrated directly into the manufacturing sequence, and no automatic linkage exists between stress analysis results and fabrication control.

Disclosed herein are methods and systems to improve biomechanical performance, certain systems have incorporated finite element analysis (FEA) or other biomechanical simulation modules into the design phase. In these approaches, stress distributions under physiological loading are computed for one or more fixed device geometries, and the results are used to guide manual redesign iterations. Although sensitivity analyses can be performed to identify high-stress regions, the simulation tools and the manufacturing instructions could remain decoupled: the designer must manually interpret the analysis, modify the CAD model, and then reinitiate the fabrication workflow. As a result, a problem is that each iteration requires human intervention and is prone to delays and potential errors in transferring updated geometries to the fabrication device. The technology herein solves this problem.

Some reported systems have sought to automate optimization loops by programmatically adjusting device geometries based on simulation outcomes. These methods typically involve software-only feedback loops in which an automated script modifies parameters and re-runs the simulation until predefined convergence criteria are met. However, fabrication is only triggered after the optimization loop completes, and no mechanism is provided to enforce material constraints or to prevent premature machine actuation during intermediate iterations. Safety interlocks in conventional additive manufacturing control systems are generally hardware-oriented and lack integration with patient-specific stability criteria or computationally locked design parameters.

Various embodiments of the technology disclosed herein relate to a system for manufacturing patient-specific spinal fixation devices, including a computing platform configured to execute biomechanical simulations of candidate device geometries under physiological loading conditions to calculate stress states and compute sensitivity gradients, and a manufacturing controller communicatively coupled to the computing platform and a physical fabrication device. The manufacturing controller receives a candidate device geometry, executes a conditional gating protocol that inhibits manufacturing instructions and manual initiation inputs while a stability criterion-defined by immutable patient-specific material constraints-remains unsatisfied, automatically triggers geometry optimization based on the computed sensitivity gradients, and permits fabrication only for a modified geometry that satisfies the stability criterion. The conditional gating protocol enforces a hardware-enforced isolation state of the fabrication actuation mechanism, physically preventing fabrication absent a convergence authorization signal from the computing platform. In some embodiments, the locked state is implemented via a Category 4/PL e safety relay (e.g., Pilz PNOZ) that physically breaks power to the bending actuators. Alternative hardware implementations include cryptographic withholding of G-code decryption keys or a hardware watchdog timer that requires a signed convergence token every 100 ms to keep servo power enabled.

According to some aspects, the technology herein can be described as a system for manufacturing patient-specific spinal fixation devices using biomechanical simulation with sensitivity-gradient-driven optimization and hardware-enforced conditional gating.

Spinal fusion for adult deformity correction requires placement of contoured spinal fixation rods spanning multiple vertebral levels. Rod contouring quality directly impacts alignment outcomes (40% surgeon-to-surgeon variation), construct biomechanics, and long-term complications including proximal junctional kyphosis (PJK: 25-40%) and rod fracture (10-15%).

Traditional methods involving manual intraoperative bending present significant limitations. Microfractures induced during manual bending reduce fatigue life by approximately 60%. Inconsistent curvature profiles result from manual techniques, with high variability demonstrated by intraclass correlation coefficients (ICC) below 0.6 between surgeons.

Existing systems lack a critical safety mechanism: hardware-level enforcement that prevents manufacturing of biomechanically unvalidated rod geometries. Current approaches permit manual overrides, sequential (non-integrated) validation, or output of manufacturing instructions before optimization convergence. This creates patient safety risks when inadequately validated devices proceed to fabrication.

What is needed (and disclosed herein) is a system architecture where the manufacturing controller physically cannot transmit fabrication instructions until the computing platform has verified biomechanical convergence-a hardware interlock that cannot be bypassed through software settings or manual intervention. It is important to note that any method, system, and/or technique herein can be done in real-time during a surgery. As such, keeping in mind possible combination embodiments and the above discussion, as an additional brief summary or to provide discussion points for a brief summary, some example features contemplated for the technology disclosed herein can be briefly summarized by the following list of features, any of which can be inter-combined or discussed optionally with any other example, feature, Figure, Drawing, detail, embodiment, and/or aspect disclosed herein:

Feature 1: A system for manufacturing patient-specific spinal fixation devices, comprising: a computing platform configured to execute a biomechanical simulation of a candidate device geometry to calculate a stress state under physiologic loading conditions and to compute sensitivity gradients derived directly from said stress state; and a manufacturing controller communicatively coupled to the computing platform and to a physical fabrication device, the manufacturing controller being configured to: (a) receive the candidate device geometry; (b) execute a conditional gating protocol that inhibits execution of manufacturing instructions corresponding to the candidate device geometry and disables manual manufacturing initiation inputs while a stability criterion remains unsatisfied, wherein said stability criterion comprises immutable material constraints derived from patient-specific parameters that are computationally locked against user modification during the conditional gating protocol; (c) automatically trigger an optimization iteration by the computing platform to modify the candidate device geometry based on the computed sensitivity gradients; and (d) permit execution only of manufacturing instructions corresponding to a modified device geometry that satisfies the stability criterion; wherein said conditional gating protocol maintains a locked state comprising a hardware-enforced isolation state of a fabrication actuation mechanism within the physical fabrication device, such that the execution of the manufacturing instructions is physically prevented absent a convergence authorization signal from the computing platform indicating satisfaction of the stability criterion.

Feature 2: The system of feature 1, wherein the locked state comprises a cryptographic interlock in which the manufacturing instructions are encrypted by the computing platform and the manufacturing controller prevents decryption and transmission of the manufacturing instructions to the physical fabrication device until a convergence authorization signal that includes a decryption key is received.

Feature 3: The system of feature 1, wherein the biomechanical simulation uses a digital twin model with distinct, physiologically representative material property domains for cortical bone, cancellous bone, and intervertebral soft tissues, and wherein the computing platform dynamically updates stiffness parameters based on a patient-specific dynamic bone quality map derived from preoperative computed tomography Hounsfield units.

Feature 4: The system of feature 3, wherein the stability criterion requires the stress state to yield a predicted screw pullout force exceeding a threshold calculated from localized bone density values in the dynamic bone quality map.

Feature 5: The system of feature 1, wherein the computing platform renders a manufacturing actuation widget on a user interface in a deactivated state that electronically suppresses user inputs until receipt of the convergence authorization signal, irrespective of widget visibility or user interaction attempts.

Feature 6: The system of feature 1, wherein the sensitivity gradients are computed via adjoint methods and mathematically constrain each subsequent optimization iteration by incorporating stress tensor values from prior iterations as required input parameters.

Feature 7: The system of feature 1, wherein the computing platform comprises a distributed architecture in which the biomechanical simulation is executed on a remote server, and the manufacturing controller is a local hardware device configured to maintain the locked state until receipt of the convergence authorization signal from the remote server, thereby enforcing the conditional gating protocol across a network boundary.

Feature 8: The system of feature 1, wherein the physiologic loading conditions include a compressive follower load between 200 and 1200 Newtons, flexion/extension moments of ±7.5 Nm, and lateral bending and axial rotation moments of ±5.0 Nm.

Feature 9: The system of feature 1, wherein the physical fabrication device comprises a robotic rod bender with force-feedback sensors configured to halt operation upon detecting material yield exceeding a predetermined threshold during execution of the manufacturing instructions.

Feature 10: The system of feature 1, wherein the stability criterion comprises a maximum von Mises stress below 60% of a material yield strength and a predicted fatigue life exceeding 10^7 cycles under cyclic physiologic loading.

Feature 11: The system of feature 1, wherein the manufacturing controller is further configured to maintain an immutable audit log of all locked-to-unlocked state transitions, including timestamps and stability criterion values, for regulatory compliance.

Feature 12: A method for manufacturing a patient-specific spinal fixation device, comprising: executing, by a computing platform, a biomechanical simulation of a candidate device geometry to calculate a stress state under physiologic loading conditions; computing, by the computing platform, sensitivity gradients derived directly from said stress state; maintaining, by a manufacturing controller communicatively coupled to a physical fabrication device, a locked state that physically prevents the physical fabrication device from executing manufacturing instructions via hardware-level isolation of a fabrication actuation circuit; evaluating, by the computing platform, whether the candidate device geometry satisfies a stability criterion defined by fixed material yield properties; generating, by the computing platform, a convergence authorization signal upon satisfaction of the stability criterion; and transitioning, by the manufacturing controller, from the locked state to an unlocked state upon receipt and validation of the convergence authorization signal, thereby permitting the physical fabrication device to execute the manufacturing instructions regardless of any manual manufacturing initiation attempts occurring during the locked state.

Feature 13: The method of feature 12, wherein maintaining the locked state further comprises intercepting and discarding all user interface signals from a manufacturing actuation widget until the convergence authorization signal is validated.

Feature 14: The method of feature 12, further comprising iteratively modifying the candidate device geometry based on the sensitivity gradients until the stability criterion is satisfied, wherein each iteration incorporates stress tensor values from a prior simulation as binding constraints.

Feature 15: The method of feature 12, further comprising, after execution of the manufacturing instructions, automatically returning the manufacturing controller to the locked state upon completion of the manufacturing instructions or expiration of a timeout period.

Feature 16: The method of feature 12, wherein calculating the stress state comprises using, by the computing platform, a surrogate machine learning model trained to approximate finite element analysis outputs based on device curvature parameters, thereby reducing computation time relative to full finite element analysis.

Feature 17: A system for manufacturing patient-specific spinal fixation devices, comprising: a generative artificial intelligence module comprising a machine learning model trained on a database of historical spinal alignments and postoperative outcomes, the generative artificial intelligence module being configured to receive patient-specific anatomical parameters and to generate a candidate rod geometry; a finite-element simulation processor configured to receive the candidate rod geometry from the generative artificial intelligence module and to execute a biomechanical simulation to calculate a stress state verification; and a hardware-interlocked manufacturing controller communicatively coupled to the generative artificial intelligence module, the finite-element simulation processor, and a physical fabrication device, the manufacturing controller being configured to: (a) compare the stress state verification with a safety threshold; (b) upon detecting that the safety threshold is violated, automatically intercept any fabrication initiation command and transmit a regeneration signal to the generative artificial intelligence module, the regeneration signal comprising stress tensor constraints derived from a location of the violation; (c) receive a regenerated rod geometry from the generative artificial intelligence module, the regenerated rod geometry having been generated using the stress tensor constraints as a generative parameter; and (d) restrict transmission of manufacturing instructions to the physical fabrication device to only rod geometries for which the finite-element simulation processor has provided a clearance signal indicating that the safety threshold is satisfied.

Feature 18: The system of feature 17, wherein the generative artificial intelligence module utilizes the stress state verification from the finite-element simulation processor as a physics-informed loss function, and wherein the machine learning model is penalized for generating geometries that result in stress concentrations exceeding the safety threshold.

Feature 19: The system of feature 17, wherein the generative artificial intelligence module comprises a Generative Adversarial Network, and the finite-element simulation processor serves as a discriminator that rejects geometries based on stress state exceedance of the safety threshold.

Feature 20: The system of feature 17, wherein the generative artificial intelligence module comprises a transformer-based architecture employing an attention mechanism to prioritize historical alignments matching the patient-specific anatomical parameters.

Feature 21: The system of feature 17, wherein the hardware-interlocked manufacturing controller enforces the restriction by maintaining a fabrication actuation mechanism of the physical fabrication device in a de-energized state until cryptographic validation of the clearance signal, thereby preventing AI hallucination-induced defects regardless of user override attempts.

Feature 22: The system of feature 17, wherein the generative artificial intelligence module employs federated learning to refine the machine learning model across institutions using de-identified postoperative data.

Feature 23: The system of feature 17, further comprising a continuous learning pipeline configured to feed postoperative imaging of implanted devices back into the generative artificial intelligence module via reinforcement learning with rewards based on clinical outcomes.

Feature 24: The system of feature 17, wherein the patient-specific anatomical parameters include soft tissue quality metrics, and wherein the generated candidate rod geometry incorporates a variable stiffness profile optimized based on the soft tissue quality metrics.

Feature 25: The system of feature 17, wherein the generative artificial intelligence module generates the candidate rod geometry as a three-dimensional point cloud that is converted directly to G-code manufacturing instructions.

Feature 26: A method of manufacturing an inventory of pre-contoured spinal fixation rods for subsequent intraoperative selection, comprising: (a) generating, by a computing platform, a plurality of candidate rod geometries derived from clustered historical patient anatomical parameters; (b) for each candidate rod geometry, executing, by the computing platform, a biomechanical simulation under physiologic loading conditions to calculate a stress state and to compute sensitivity gradients derived directly from said stress state; (c) iteratively optimizing, by the computing platform, each candidate rod geometry using the sensitivity gradients until a stability criterion is satisfied and a convergence authorization signal is generated; and (d) fabricating and stocking only those pre-contoured spinal fixation rods corresponding to candidate rod geometries for which the convergence authorization signal has been validated by a hardware-interlocked manufacturing controller configured to physically prevent fabrication of any rod geometry lacking the convergence authorization signal via a locked state that cannot be bypassed by manual override.

Feature 27: The method of feature 26, wherein the hardware-interlocked manufacturing controller maintains the locked state by electrical de-energization of a fabrication actuation circuit or by cryptographic withholding of a decryption key required to transmit manufacturing instructions to a physical fabrication device.

Feature 28: The method of feature 26, wherein the clustered historical patient anatomical parameters are stratified by pelvic incidence and global sagittal alignment classifications, and wherein the inventory covers at least 95 percent of a target patient population with no more than 2.0 degrees average alignment error.

Feature 29: The method of feature 26, wherein each stocked pre-contoured spinal fixation rod is marked with a unique identifier linking to its originating validated candidate rod geometry and associated biomechanical simulation results.

Feature 30: The method of feature 26, wherein the fabricated pre-contoured spinal fixation rods exhibit a surface roughness Ra of not more than 0.4 micrometers in all curved regions and a predicted fatigue life exceeding 1.5×10^7 cycles under cyclic physiologic loading, both resulting from exclusion of manual bending and enforcement of the stability criterion.

Feature 31: A method for using a trained network to form a spinal fixation rod, the method comprising the steps of: training, by a computer, a neural network based on input data and a selected training algorithm to generate a trained neural network, wherein the input data consists of anatomical parameters, the anatomical parameters comprising: pelvic incidence; pelvic tilt; thoracic kyphosis magnitude and shape; and a vertebral pelvic angle (VPA), the VPA being at least one of the vertebral pelvic angles for vertebrae L4, L1, T10, T7, T4, T1, C5, and C2; distance from a femoral head to an S1 endplate; segment distances between vertebrae L4-S1, L1-L4, T10-L1, T1-T5, and T5-T9; position of vertebral centers for vertebrae C2 to S1; and orientations of vertebral endplates; generating, by the trained neural network, an estimated pelvic orientation and an estimated pelvic shape based upon the pelvic tilt data, the pelvic incidence data, and the data of distance from femoral head to S1 endplate; generating, by the trained neural network, a spline based upon the VPA, the estimated pelvic shape, the estimated pelvic orientation, and the segment distances; generating, by the trained neural network, estimated positions of vertebrae along the spline based upon positions of vertebral centers; generating, by the trained neural network, an estimated angulation between the spline and each endplate based upon the spline, the VPA and the orientations of the vertebral endplates; generating, by the trained neural network, an ideal full spine shape by combining the estimated angulation and the estimated positions of the vertebrae; and forming the spinal fixation rod based upon the ideal spine shape.

Feature 32: The method of feature 31, further comprising the step of: defining thoracic kyphosis using a regression method where $R^2$ is at least 0.9 (optionally at least 0.8).

Feature 33: The method of feature 32, further comprising the step of: defining pelvic incidence relationship with VPA using a regression method where $R^2$ is at least 0.8.

Feature 34: The method of feature 31, further comprising the steps of: defining thoracic kyphosis using a regression method; and defining pelvic incidence relationship with VPA using a regression method; and wherein $R^2$ is at least 0.8.

Feature 35: The method of feature 31, wherein the anatomical parameters further comprise at least one of regional Cobb angles, and segmental Cobb angles, and the step of generating a spline is further based upon at least at least one of regional Cobb angles, and segmental Cobb angles.

Feature 36: A method for forming a spinal rod (e.g., patient specific in Features 36-43), the method comprising the steps of: obtaining data representing a patient's spinal parameters, the spinal parameters comprising: pelvic incidence; pelvic tilt; thoracic kyphosis; and a vertebral pelvic angle (VPA), the VPA being at least one of the vertebral pelvic angles for vertebrae L4, L1, T10, T7, T4, T1, C5, and C2; distance from a femoral head to an S1 endplate; segment distances between vertebrae L4-S1, L1-L4, T10-L1, T1-T5, and T5-T9; position of vertebral centers for vertebrae C2 to S1; regional or segmental Cobb angles; and orientations of vertebral endplates; inputting the patient data into a neural network trained on historical datasets of the spinal parameters; generating, via the neural network, an ideal spine shape; forming a spinal rod based upon the ideal spine shape.

Feature 37: The method of feature 36, wherein the historical data further comprises: intervertebral heights; heights of vertebral bodies; intervertebral angulation; vertebral angulation; segmental alignment of each level from T1 to pelvis; and distances between implanted rods and vertebral bodies based on postoperative imaging.

Feature 38: The method of feature 37, further comprising the step of: modeling the ideal spine shape using a gravity line biomechanical model that predicts reciprocal changes above fused vertebral segments and pelvic position in space.

Feature 39: The method of feature 38, wherein the ideal spine shape accounts for posterior translation of the spinal rod from the patient's pelvis.

Feature 40: The method of feature 39, wherein the ideal spine shape accounts for thoracolumbar alignment and cervical alignment based on the patient's spinal parameters in order for the patient to maintain proper head position and proper horizontal gaze.

Feature 41: The method of feature 40, wherein the rods extend from vertebra T1 to the pelvis.

Feature 42: The method of feature 40, wherein the rods extend from vertebra C2 to vertebra T1.

Feature 43: The method of feature 36, wherein contours of the spinal rod are optimized using a finite element model to predict complications at a junction between fused and unfused vertebrae in order to minimize likelihood of mechanical related complications and or proximal junctional kyphosis and proximal junctional failure.

Feature 44: The method of feature 36 (e.g., population specific in Features 44-53), wherein the historical data further comprises: intervertebral heights; heights of vertebral bodies; intervertebral angulation; vertebral angulation; segmental alignment of each level from T1 to pelvis; and distances between implanted rods and vertebral bodies based on postoperative imaging.

Feature 45: The method of feature 44, further comprising the step of: modeling the ideal spine shape using a gravity line biomechanical model that predicts reciprocal changes above fused vertebral segments and pelvic position in space.

Feature 46: The method of feature 45, wherein the ideal spine shape accounts for posterior translation of the spinal rod from the patient's pelvis.

Feature 47: The method of feature 46, wherein the ideal spine shape accounts for thoracolumbar alignment and cervical alignment based on the patient's spinal parameters in order for the patient to maintain proper head position and proper horizontal gaze.

Feature 48: The method of feature 47, wherein the rods extend from vertebra T1 to the pelvis.

Feature 49: The method of feature 47, wherein the rods extend from vertebra C2 to vertebra T1.

Feature 50: The method of feature 36, wherein the finite element model is configured to predict the impact of rod stiffness, fixation techniques, and the ideal shape on adjacent segment loading.

Feature 51: The method of feature 50, wherein the finite element model is configured to predict the influence of different spinal rod materials on adjacent segment biomechanics.

Feature 52: The method of feature 51, wherein the finite element model is configured to predict the effects of hybrid spinal rods on spinal rod biomechanics to optimize load distribution and minimize abrupt angulation transitions.

Feature 53: The method of feature 52, wherein the finite element model is configured to predict the effects of interactions of patient soft tissue with the rods over the life of a model patient on spinal rod biomechanics.

Feature 54: The method of feature 53, wherein the finite element model is configured to predict spinal rod fatigue related failure at junctional zones.

Feature 55: A spinal rod formed by the method of features 31 through 53.

Feature 56: The spinal rod of feature 55, wherein the rod comprises regions, the regions corresponding to the patient's segment alignment between vertebrae L4-S1, L1-L4, T10-L2, T5-T9, T1-T6.

Feature 57: The spinal rod of feature 56, wherein the regions are visually indicated on the spinal rod.

Feature 58: The spinal rod of feature 57, wherein angulation inflection points are visually indicated on the spinal rod.

Feature 59: A system for forming spinal rods comprising: a processing unit comprising a neural network trained on a set of data of patient spinal parameters, the patient spinal parameters comprising: pelvic incidence; pelvic tilt; thoracic kyphosis; and a vertebral pelvic angle (VPA), the VPA being at least one of the vertebral pelvic angles for vertebrae L4, L1, T10, T7, T4, T1, C5, and C2; distance from a femoral head to an S1 endplate; ideal segment alignment between vertebrae that is associated with the lowest biomechanical complications based on historical data L4-S1, L1-L4, T10-L1, T1-T5, and T5-T9; position of vertebral centers for vertebrae C2 to S1; regional or segmental Cobb angles; and orientations of vertebral endplates; and wherein the processing unit is configured to: receive data representing a patient's spinal parameters; input the patient data into the neural network; and generate, via the neural network, an ideal spine shape.

Feature 60: The system of feature 59, wherein the processing unit is configured to generate the ideal spine shape by executing the steps of: generating, by the trained neural network, an estimated pelvic orientation and an estimated pelvic shape based upon the pelvic tilt data, the pelvic incidence data, and the data of distance from femoral head to S1 endplate; generating, by the trained neural network, a spline based upon the VPA, the estimated pelvic shape, the estimated pelvic orientation, and the segment distances; generating, by the trained neural network, estimated positions of vertebrae along the spline based upon positions of vertebral centers; generating, by the trained neural network, an estimated angulation between the spline and each endplate based upon the spline, the VPA and the orientations of the vertebral endplates; generating, by the trained neural network, an ideal full spine shape by combining the estimated angulation and the estimated positions of the vertebrae.

Feature 61: The system of feature 60, wherein the processing unit is further configured to: define thoracic kyphosis using a regression method; and define pelvic incidence relationship with VPA using a regression method; and wherein R2 is at least 0.8.

Feature 62: The system of feature 59, wherein the historical data further comprises: intervertebral heights; heights of vertebral bodies; intervertebral angulation; vertebral angulation; segmental alignment of each level from T1 to pelvis; and distances between implanted rods and vertebral bodies based on postoperative imaging.

Feature 63: The system of feature 62, wherein the ideal spine shape is modeled using a gravity line biomechanical model that predicts reciprocal changes above fused vertebral segments and pelvic position in space.

Feature 64: The system of feature 62, wherein the ideal spine shape accounts for posterior translation of the spinal rod from the patient's pelvis.

Feature 65: The system of feature 62, wherein the ideal spine shape accounts for thoracolumbar alignment and cervical alignment based on the patient's spinal parameters in order for the patient to maintain proper head position and proper horizontal gaze.

Feature 66: The system of feature 62, wherein the rods extend from vertebra T1 to the pelvis.

Feature 67: The system of feature 62, wherein the rods extend from vertebra C2 to vertebra T1.

Feature 68: The system of feature 62, wherein contours of the spinal rod are optimized using a finite element model to predict complications at a junction between fused and unfused vertebrae in order to minimize likelihood of proximal junctional kyphosis and proximal junctional failure.

It is contemplated that the systems, devices, and methods can be remote-operated, or stable, easily boxed, shipped and portable in kits and/or in smartphone based apps. It is important to note in the context of this disclosure that the materials and the methods can be used for production of kits, methods for assembling the kits, or for other constructs.

According to some aspects, the features, options, parameters, dimensions, materials, mounting configurations, arrangements, components, embodiments, and examples described in this Summary are each disclosed individually and in any technically sensible combination with one another and with features described elsewhere herein. Other implementations are also described and recited herein. These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The system and related methods disclosed herein are described with reference to the accompanying drawings. In the drawings, like reference numbers indicate identical or functionally similar elements when reasonable.

Figure 1:
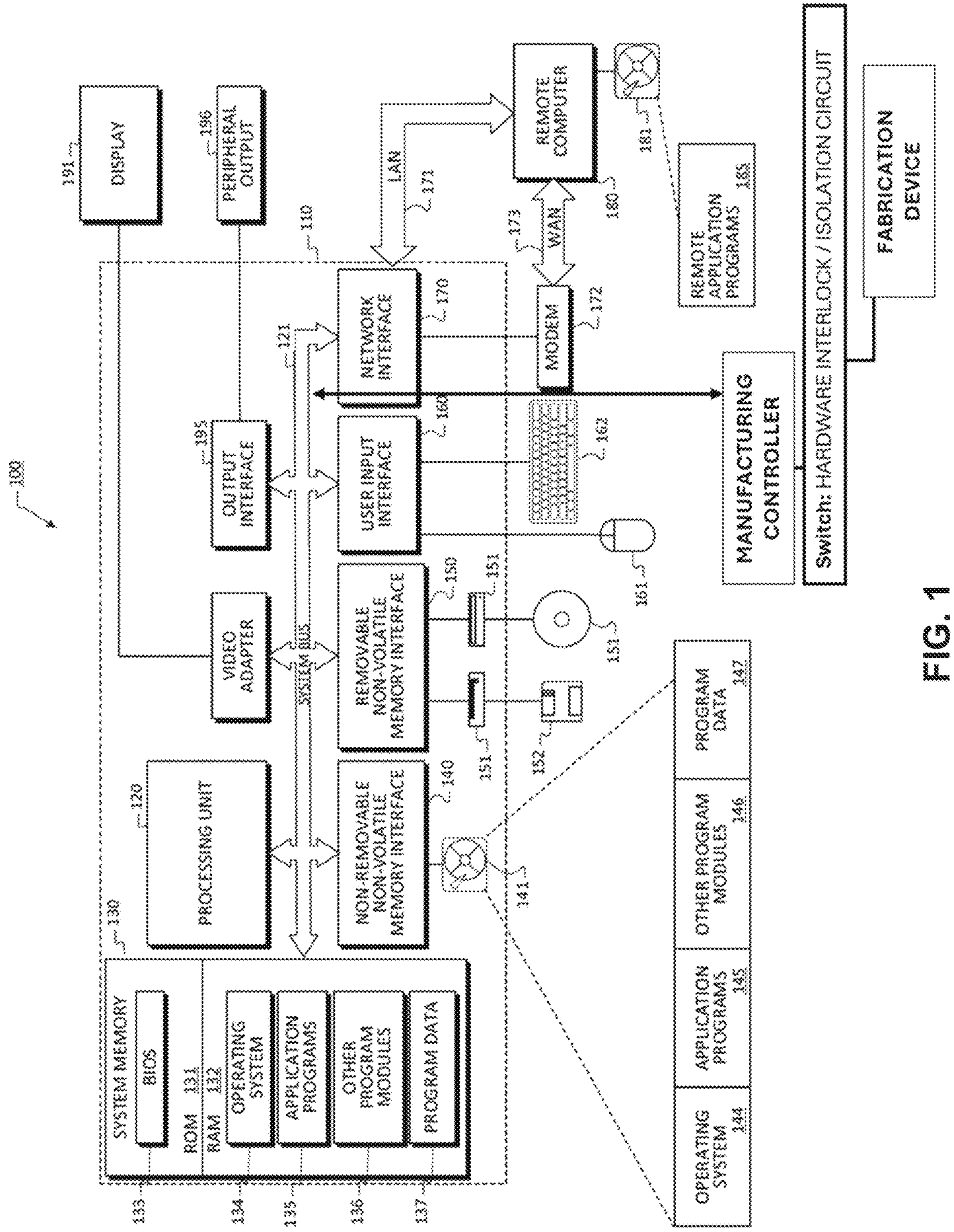
FIG. 1 is a system block diagram of the computing platform, modified to show the hardware-interlocked manufacturing controller and isolation circuit.

It should be understood that while different numbers/numbering could be sometimes used in some of the figures above to describe different embodiments and different aspects of the technology, any number from any figure can be inter-combined with a numbered aspect from any other figures.

DETAILED DESCRIPTION

The various embodiments of the disclosed method and system and their advantages are best understood by referring to FIGS. 1 through 12 of the drawings. The elements of the drawings are not necessarily to scale, emphasis instead being placed upon clearly illustrating the novel features and principles of operation. Throughout the drawings, like numerals are used for like and corresponding parts of the various drawings.

As such, the presently disclosed innovation is now described in more detail with some reference to the drawings, when practical, to refer to methods throughout. In the following description, for purposes of explanation, numerous specific details are set forth in order to provide a thorough understanding of the present invention. It may be evident, however, that the present invention may be practiced without these specific details. In other instances, well-known structures and devices are illustrated in a block diagram form in order to facilitate describing the present invention.

Accordingly, the following description of particular aspects is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions or processes are described as using specific materials or an order of individual steps, it is appreciated that materials or steps may be interchangeable such that the description of the invention may include multiple parts or steps arranged in many ways as is readily appreciated by one of skill in the art. For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail. This disclosure is purposefully presented in commonly understood words, known to a person of skill in the art, but Merriam-Webster's Online Dictionary is used, when appropriate, for terms not specifically demonstrated herein or not known in the art.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g., a feature, element, characteristic, property, method/process step or limitation) or group of integers (e.g., features, element, characteristics, properties, method/process steps or limitations) but not the exclusion of any other integer or group of integers. Thus, as used herein the term "comprising" is inclusive or open-ended and does not exclude additional, unrecited integers or method/process steps.

Furthermore, reference in the specification to "an embodiment," "one embodiment," "various embodiments," or any variant thereof means that a particular feature or aspect described in conjunction with the particular embodiment is included in at least one embodiment. Thus, the appearance of the phrases "in one embodiment," "in another embodiment," or variations thereof in various places throughout the specification are not necessarily all referring to its respective embodiment.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention. The term "consisting essentially of" can also be exemplified by plain language provided in the claims.

The term "statistically significant" or "significantly" refers to statistical significance and generally means a two-standard deviation (2SD) or greater difference.

The term "treating" includes prophylactic and/or therapeutic treatments. The term "prophylactic or therapeutic" treatment is art-recognized and includes administration to the host of one or more of the subject compositions and/or application of one or more therapies or surgeries. If this is done prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the terms "treat," "treatment," "treating," or "amelioration" when used in reference to a disease, disorder, or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), sign(s), diminishment of extent of the deficit, stabilized (i.e., not worsening) state of a symptom or condition, delay or slowing of onset of symptoms or indications, and an increased lifespan as compared to that expected in the absence of treatment.

A "subject," or "patient," can be one who has been previously diagnosed with or identified as suffering from or having a condition in need of treatment (e.g., a scoliosis, spinal deformity, spinal stenosis, spondylolisthesis, or related disorder) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition, or one or more complications related to a condition or a subject who does not exhibit risk factors. A "subject in need" of treatment for a particular condition can be a subject having that condition, diagnosed as having that condition, suspected as having, or at risk of developing that condition. In another example, the subject has been brought into a treatment situation entirely without the subject's knowledge and/or intent. For example, a subject can obviously be in need of treatment but not be responsive to an immune checkpoint inhibitor, and as described herein the present methods and formulations may save the subject's life.

A spinal fixation rod can be a material spanning two or more vertebrae. Pedicle screws help secure rods and/or plates to the spinal segment(s) during a spinal fusion surgery. Pedicle screws are threaded FDA (US Food and Drug Agency) or a national health authority approved material (e.g., titanium, cobalt, chrome, or stainless-steel) implants that are fastened through the vertebral pedicles located at the back of the spinal bones. The screws act as anchor points and are typically positioned at two or more consecutive spinal segments connected by a rod. Rod shape can dictate the spinal shape and can be derived specifically for the patient using the patient's pelvic incidence. The tulip head of a pedicle screw is a point of attachment for a rod and/or plate.

Figure 2:
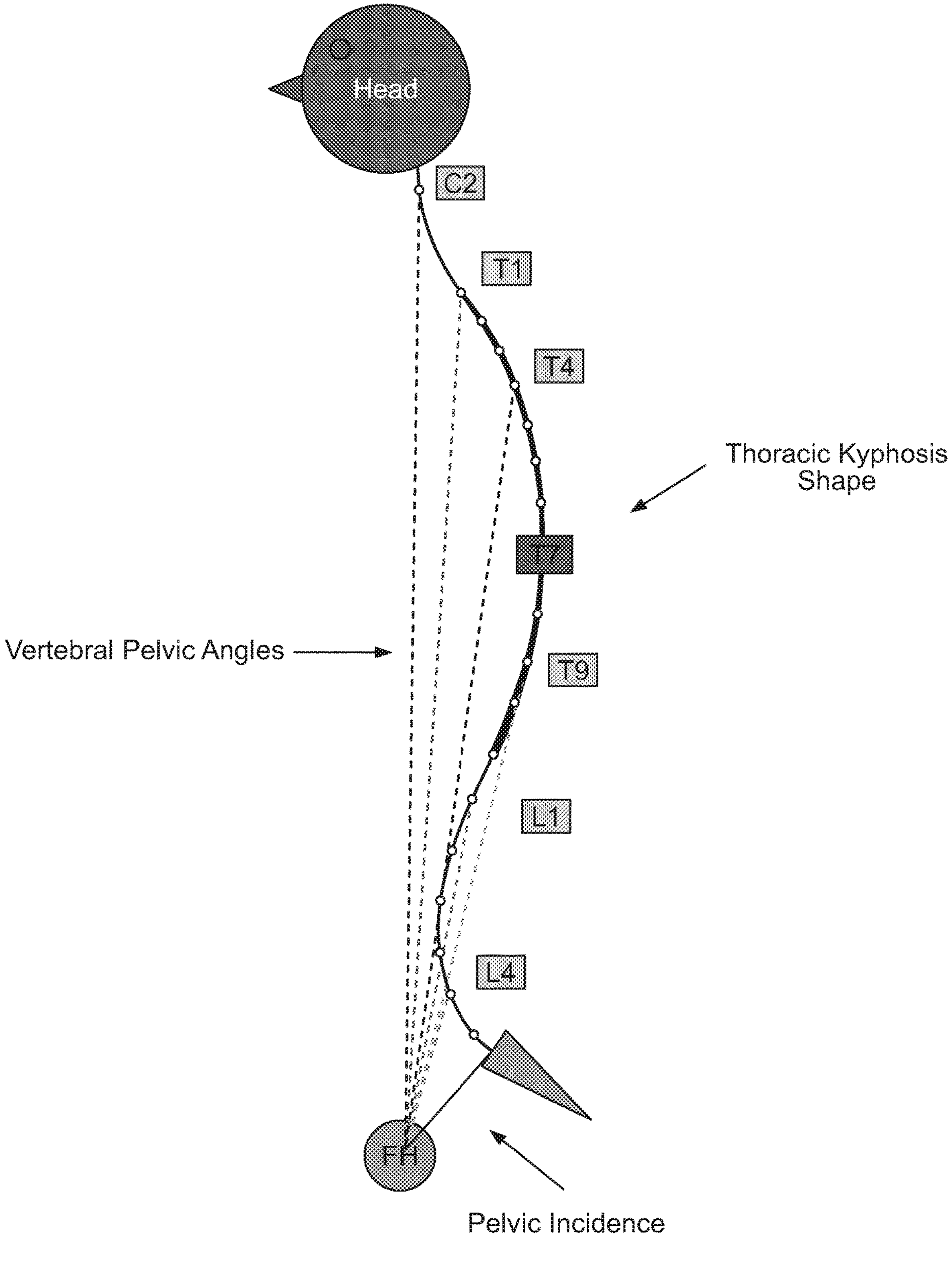
FIG. 2 is a schematic diagram illustrating spinal alignment parameters including pelvic incidence and thoracic kyphosis.

With reference to FIG. 2, "Pelvic incidence" (PI), also known as pelvisacral angle, is a fixed number for each patient, and is determined by the angle between a line perpendicular to the sacral plate at its midpoint and a line connecting the same point to the center of the bicoxofemoral axis.

Also illustrated in FIG. 2 is the "vertebral pelvic angle" (VPA) which is defined as the angle formed between a line drawn along the posterior surface of the sacrum (typically from the posterior-superior corner of S1), and a line drawn from that point to the center of the vertebral body. This angle helps assess the relationship and alignment between the vertebrae and the pelvis, giving insight into the degree of anterior displacement (slippage) of the vertebra and the sacral inclination.

"Pelvic tilt" is the angle between the vertical axis and the line connecting the midpoint of the sacral plate to the axis of the femoral heads. This angle indicates the orientation of the pelvis in the sagittal plane and is a critical factor in assessing spinal alignment.

As used herein, "hardware interlock" or "hardware-interlocked" refers to a physical or firmware-level mechanism in the manufacturing controller that prevents transmission of fabrication instructions to the physical fabrication device. The hardware interlock cannot be bypassed through software parameter changes, user interface interactions, or manual override commands.

As used herein, "locked state" refers to the default operational state of the manufacturing controller wherein the physical fabrication device is prevented from receiving or executing manufacturing instructions. The locked state persists until a valid convergence authorization signal is received.

As used herein, "unlocked state" refers to the operational state of the manufacturing controller wherein manufacturing instructions may be transmitted to the physical fabrication device. The unlocked state is achieved only upon receipt of a convergence authorization signal.

As used herein, "convergence authorization signal" refers to a digital signal generated by the computing platform upon verification that the candidate rod geometry satisfies a stability criterion. The convergence authorization signal includes cryptographic verification preventing spoofing or unauthorized generation.

As used herein, "Electrical De-energization" refers to the physical interruption of power or control signal continuity to the actuation motors of the physical fabrication device. This is distinct from a software "pause" command. In the state of Electrical De-energization, the fabrication device is physically incapable of movement, regardless of the logical state of the software user interface, effectively creating an "air gap" between the operator's intent and the machine's capability.

As used herein, "Hardware-Enforced Isolation" refers to a state wherein the fabrication actuation mechanism is rendered unresponsive to standard operation commands. This includes physical electrical de-energization (breaking the circuit), but also encompasses firmware-level masking, interrupt-driven logic gating, or optical isolation wherein the motor controller physically or logically discards drive packets absent the authorization token. The key distinction is that the isolation cannot be cleared by the high-level user interface software alone.

As used herein, "stability criterion" refers to any metric or combination of metrics indicating that the optimization process has reached a stable solution. It is understood that stability criteria may be defined by various statistical methods, including but not limited to: rate-of-change metrics falling below a predetermined threshold; root-mean-square deviation stability; asymptotic behavior verification; consecutive iteration comparison; gradient magnitude thresholds; or other convergence detection methods known in the art. The stability criterion is not limited to any specific percentage threshold or iteration count.

As used herein, "sensitivity gradient" refers to a mathematical quantity representing the rate of change of an objective function with respect to design parameters, wherein the gradient is derived from the stress state computed by biomechanical simulation. The sensitivity gradient mathematically constrains the optimization path.

As used herein, "physiologic loading conditions" refers to loading conditions sufficient to induce stress tensor variations representative of in vivo spinal biomechanics. Physiologic loading conditions include, but are not limited to, follower loads, flexion/extension moments, lateral bending moments, and axial rotation moments at magnitudes representative of human spinal loading.

As used herein, "physiologically representative material properties" refers to material property values within ranges characteristic of human spinal structures, including but not limited to cortical bone, cancellous bone, nucleus pulposus, annulus fibrosus, and ligamentous tissues. The specific numerical values may vary based on patient demographics, pathology, and modeling assumptions while remaining within physiologically plausible bounds.

As used herein, "generative artificial intelligence module" refers to a computational module comprising one or more machine learning models configured to generate candidate rod geometries from input parameters. The generative artificial intelligence module may comprise neural networks including but not limited to generative adversarial networks, transformer architectures, variational autoencoders, or reinforcement learning agents.

As used herein, "finite-element simulation processor" refers to a computational module configured to execute biomechanical simulations including finite element analysis to calculate stress states and verify structural integrity of candidate rod geometries. The finite-element simulation processor operates independently of the generative artificial intelligence module to provide safety verification.

As used herein, "AI hallucination" refers to the phenomenon wherein generative artificial intelligence systems produce outputs that are structurally plausible but physically invalid or unsafe. The hardware interlock architecture prevents AI hallucinations from resulting in manufactured defects by requiring independent physics-based validation.

As used herein, "digital twin" refers to a virtual representation of a physical spinal construct comprising patient-specific anatomical structures with assigned physiologically representative material properties. The digital twin enables biomechanical simulation under physiologic loading conditions.

As used herein, "Manufacturing Actuation Widget" refers to any user interface element, physical control, or input mechanism configured to initiate the transmission of manufacturing instructions to the physical fabrication device. This includes, but is not limited to, virtual buttons (e.g., "Print," "Bend," "Fabricate") displayed on a graphical user interface (GUI), physical emergency-stop-style activation buttons, foot pedals, voice command triggers, or gesture-based inputs in augmented reality environments. The Manufacturing Actuation Widget serves as the final human authorization step before physical fabrication begins.

As used herein, "Deactivated State" refers to a specific operational mode of the Manufacturing Actuation Widget wherein user interaction with the widget is electronically suppressed or ignored by the manufacturing controller. In the Deactivated State, the widget fails to generate or transmit the necessary actuation signals to the physical fabrication device, effectively rendering the manufacturing trigger inert. This state is distinct from a mere "warning" or "alert" in that it physically or logically prevents the execution command from being processed, regardless of user intent. The disclosed system deliberately excludes any embodiment, mode, or workflow in which fabrication of the spinal rod may be initiated solely by human visual confirmation, manual authorization signal, surgeon override command, or any user-interface interaction in the absence of a cryptographically signed convergence token that is generated exclusively from the computed stress tensor field of the biomechanical simulation. This exclusion ensures that no rod geometry can be physically manufactured without objective, machine-verified biomechanical convergence, even in the presence of purported emergency or manual bypass procedures.

As used herein, "Activated State" refers to the operational mode wherein the Manufacturing Actuation Widget is enabled to transmit manufacturing instructions. The transition from the Deactivated State to the Activated State is strictly conditional upon the receipt of the convergence authorization signal.

As used herein, "Human-Input Inhibition Protocol" refers to a logic layer within the manufacturing controller that intercepts input signals from the Manufacturing Actuation Widget. This protocol validates the presence of a current, cryptographic convergence authorization signal before permitting the input signal to pass to the fabrication execution module. If the authorization signal is absent or invalid (e.g., due to a recent change in rod geometry that has not yet been re-simulated), the protocol actively blocks the input signal.

As used herein, "Dynamic Bone Quality Map" refers to a volumetric representation of patient bone density derived from preoperative imaging (e.g., Hounsfield Units from CT scans), mapped specifically to the vertebral levels intended for instrumentation. Unlike global bone density scores (e.g., T-scores), the Dynamic Bone Quality Map provides localized density values at the specific pedicle screw interfaces, enabling the biomechanical simulation to calculate screw pullout forces specific to each individual fixation point.

As discussed above, unless otherwise defined herein, scientific, and technical terms used in connection with the present application shall have the meanings that are commonly understood by those of ordinary skill in the art to which this disclosure belongs. The terminology used herein is for the purpose of describing particular embodiments only and is not intended to limit the scope of the present invention, which is defined solely by the claims. Other terms are defined herein within the description of the various aspects of the invention.

General combinations of features: It is to be understood that the features, elements, parameters, method steps, components, and aspects disclosed in the present description, in the drawings, and in the dependent claims are each disclosed independently and in any technically sensible combination with one another, unless the context clearly dictates otherwise or such a combination is technically incompatible. In particular, any feature described in connection with a specific embodiment, figure, "Feature" or "Detail" listing, example, kit, method, system, controller, spinal rod, digital twin, neural network, or manufacturing workflow is also disclosed, mutatis mutandis, in combination with any other embodiment, figure, Feature, Detail, example, kit, method, system, controller, spinal rod, digital twin, neural network, or manufacturing workflow described herein. Likewise, subcombinations of the features of any embodiment are also considered to be disclosed as separate embodiments, and individual features of an embodiment may be omitted or replaced by alternative features disclosed elsewhere in the application, provided that the resulting combination remains technically workable. References herein to "in some embodiments," "in an embodiment," "in another embodiment," "Feature . . . ," "Detail . . . ," and the like do not limit the disclosure to the specific combinations explicitly described, but are intended to permit recombination of the disclosed features in any manner supported by the overall technical teaching of this application.

Neural Network-Based Method for Design of Orthopedic Implants

The present invention provides a system for manufacturing patient-specific spinal fixation devices comprising a hardware-interlocked manufacturing controller. The key innovation is that the manufacturing controller maintains a locked state that physically prevents the fabrication device from executing manufacturing instructions. The controller transitions to an unlocked state only upon receipt of a convergence authorization signal generated when the candidate rod geometry satisfies a stability criterion derived from biomechanical simulation. This hardware-level blocking cannot be bypassed through software parameter changes or manual intervention.

The system comprises: (a) a computing platform configured to execute biomechanical simulation of candidate rod geometries to calculate stress states under physiologic loading conditions, and to compute sensitivity gradients derived directly from said stress states; and (b) a manufacturing controller communicatively coupled to the computing platform and a physical fabrication device, wherein the manufacturing controller is configured to maintain a locked state that prevents the physical fabrication device from executing manufacturing instructions, and to transition to an unlocked state only upon receipt of a convergence authorization signal.

The novelty resides in the hardware interlock architecture itself—the requirement that stress tensor values from simulation mathematically constrain the optimization path, and that no manufacturing output is possible until convergence is achieved. This architecture prevents fabrication of unvalidated medical devices regardless of specific simulation parameters employed.

Validation studies ($n=100$, $p<0.001$) demonstrate: convergence time reduction of 78% compared to prior approaches; alignment error reduction of 66%; maximum rod stress reduction of 42%; and fatigue life improvement of 3.5×.

In certain embodiments, the system further comprises a generative artificial intelligence module comprising a machine learning model trained on a database of historical spinal alignments and postoperative outcomes. The generative artificial intelligence module is configured to receive patient-specific anatomical parameters and generate a candidate rod geometry. The physics-based validation module receives the candidate rod geometry from the generative artificial intelligence module and executes a biomechanical simulation to calculate a stress state verification. This neuro-physical hybrid architecture ensures that AI-generated geometries are validated through physics-based simulation before any manufacturing can occur.

The generative artificial intelligence module may comprise various machine learning architectures, including but not limited to: Generative Adversarial Networks (GANs) wherein a generator network creates the candidate rod geometry and the physics-based validation module acts as a discriminator to accept or reject the geometry based on biomechanical performance; transformer-based architectures utilizing an attention mechanism to weigh the patient-specific anatomical parameters against the database of historical spinal alignments; or reinforcement learning models trained using a reward function derived from postoperative clinical outcomes.

The hardware-interlocked manufacturing controller prevents the phenomenon of AI hallucination from resulting in a physical defect by requiring the physics-based validation module to independently verify the structural integrity of the generated geometry before the unlocked state is achieved. This is a critical safety feature that addresses a known limitation of generative AI systems.

The generative artificial intelligence module may generate the candidate rod geometry by predicting a 3D point cloud and converting said point cloud into manufacturing vector instructions. The module may utilize federated learning to update the machine learning model across multiple institutional locations without transferring patient-identifiable source data, thereby maintaining HIPAA compliance while enabling continuous model improvement.

In yet another embodiment, the system is configured for universal interoperability validation. The computing platform executes a multiphysics interface simulation that virtually mates the candidate rod geometry with a target fixation profile corresponding to a third-party fixation anchor system. The simulation calculates an interface stress state quantifying mechanical mismatches, including tulip head geometric conflicts and galvanic corrosion potential. The hardware-interlocked manufacturing controller inhibits fabrication if the interface stress state exceeds a compatibility threshold, thereby ensuring that the patient-specific rod is mechanically and electrochemically compatible with the specific third-party screws intended for implantation.

In certain embodiments, the physical fabrication device 300 is further configured to apply controlled shot-peening, laser texturing, or equivalent surface treatment to the rod in the regions that contact the tulip heads of the selected third-party pedicle screw system. The target surface roughness Ra is dynamically selected within the range 0.2-0.6 μm (preferably 0.3-0.4 μm) so as to achieve a static friction coefficient $\mu_s$ that matches or exceeds the manufacturer-specified value for the chosen screw tulip, thereby maximizing locking strength and minimizing risk of rod slippage under physiologic loading.

In a broad embodiment, a problem in spinal surgeries is that the conventional rods (human-bent or currently manufactured worldwide) spinal rods do not meticulously follow the proper curvature of the human spine. Typically, for a surgeon to restore a spine with deformities, the surgeon must somehow predict the shapes and sizes of the orthopedic implants in advance. After surgery, studies reveal that about 50% of spinal surgery performed produce rods that are straightened out or over-bent into an unnatural position. At first, the unfused spinal segments compensate for the improper rod contour effects, but eventually the discs above and/or below the fusion degenerate and wear down. The patient then develops back pain, has difficulty standing upright, and experiences limitations when walking. Eventually, the problem requires yet another major surgery to realign the spine. Thus, the presently disclosed technology provides machine learning in various layers of convolutional neural networks to provide pre-planned shapes, contours, curvatures, and sizes to spinal rods (and associated hardware) that enable a surgeon to plan a desired surgical outcome for the patient. This brings great relief to patients, especially over a long-term of 2 or more years.

A major problem in spinal fusion surgeries is that, over the long term of 2 or more years, the surgeons cannot predict what pelvic incidence (PI) angulation that they place the patient's spine in—it may or may not be optimal for the patient's outcome, long term. Currently, vast majority of surgeons arbitrary assign rod shapes to their spinal fusion construct without using surgical planning. Thus, the technology disclosed herein provides machine learning, convolutional neural networks, software, and intelligent methods to design implants associated with the ideal spinal shape to optimize surgical outcomes. This saves patients years of suffering and problems such as deformity.

Another Example Description of the Problem and Related Art: Spinal scoliosis is a complex three-dimensional deformity of the spine that can lead to significant health issues, including pain, reduced mobility, and impaired respiratory function. Traditional methods of correcting scoliosis often involve invasive surgical procedures that aim to realign the spine using rods and screws. However, these methods can be associated with complications such as proximal junctional kyphosis, rod breakage, and the need for revision surgeries. The challenge in treating scoliosis lies in accurately predicting the ideal spinal alignment and ensuring that the corrective measures do not lead to further complications.

In addition to scoliosis, other spinal disorders such as kyphosis, lordosis, and spondylolisthesis also utilize spinal rods as a treatment option. Kyphosis involves an excessive outward curvature of the spine, leading to a hunched posture, and can be corrected using spinal rods to restore a more natural alignment. Lordosis, characterized by an exaggerated inward curve of the lower back, may also require the use of rods to achieve proper spinal balance. Spondylolisthesis, where one vertebra slips forward over the one below it, often necessitates stabilization with spinal rods to prevent further slippage and alleviate associated symptoms.

Recent advancements in medical technology have introduced the use of computational models and machine learning techniques to enhance the precision of scoliosis treatment. Neural networks, a subset of artificial intelligence, have shown promise in processing complex anatomical data to predict outcomes and optimize treatment plans. By leveraging historical datasets and biomechanical models, these technologies aim to improve the accuracy of spinal corrections and reduce the risk of postoperative complications. The integration of these advanced computational methods into scoliosis treatment represents a significant step forward in personalized medicine, offering the potential for more effective and tailored interventions for patients with spinal deformities. One exemplary method can involve training a neural network using a computer, based on input data and a selected training algorithm, to generate a trained neural network. The input data may consist of anatomical parameters such as pelvic incidence, pelvic tilt, thoracic kyphosis, vertebral pelvic angle (VPA) for specific vertebrae, distance from a femoral head to an S1 endplate, segment distances between specific vertebrae, positions of vertebral centers from C2 to S1, and orientations of vertebral endplates. The trained neural network can generate an estimated pelvic orientation and shape based on pelvic tilt, pelvic incidence, and femoral head to S1 endplate distance data. It may then generate a spline based on the VPA, estimated pelvic shape and orientation, and segment distances. The network can further estimate positions of vertebrae along the spline and calculate an estimated angulation between the spline and each endplate. By combining the estimated angulation and vertebral positions, an ideal full spine shape may be generated, upon which the spinal fixation rod is formed. Additionally, the method may include defining thoracic kyphosis using a regression method with an $R^2$ value of at least 0.9 and defining the relationship between pelvic incidence and VPA using a similar regression method.

Another embodiment may involve forming a spinal rod by obtaining data representing a patient's spinal parameters, inputting this data into a neural network trained on historical datasets, and generating an ideal spine shape to form the spinal rod. The historical data may include intervertebral heights, vertebral body heights, intervertebral and vertebral angulation, segmental alignment from T1 to pelvis, and distances between implanted rods and vertebral bodies based on postoperative imaging.

The ideal spine shape can be modeled using a gravity line biomechanical model to predict changes above fused segments and pelvic position, accounting for posterior translation of the spinal rod, thoracolumbar and cervical alignment, and ensuring proper head position and horizontal gaze. The contours of the spinal rod can be optimized using a finite element model to predict complications at junctions between fused and unfused vertebrae, minimizing the likelihood of proximal junctional kyphosis and failure. The finite element model can predict the impact of rod stiffness, fixation techniques, and ideal shape on adjacent segment loading, as well as the influence of different spinal rod materials and hybrid rods on biomechanics. It can also predict interactions of patient soft tissue with the rods over time and spinal rod fatigue-related failure at junctional zones. A spinal rod formed by this method may comprise regions corresponding to the patient's segment distances between specific vertebrae, with these regions and angulation inflection points visually indicated on the rod.

Rods will undergo comprehensive biomechanical evaluation through finite element modeling, AI-driven analysis, and digital twin simulations that account for varying bone quality, muscle and ligament conditions, patient demographics, and comorbidities. Insights from these simulations will form a feedback loop, guiding iterative refinements to optimize construct strength, reduce failure risk, and maintain ideal junctional forces. Each refined design will then be revalidated against criteria such as upright posture, horizontal gaze, and overall spine alignment—ensuring the final rods deliver optimal clinical outcomes under real-world conditions In some embodiments, FIG. 1 illustrates a system that integrates a computing platform, a manufacturing controller, a hardware isolation subsystem, and a physical fabrication device into a single hardware-interlocked environment. According to some aspects, the computing platform includes one or more processors, system memory, and non-volatile storage configured to execute software modules for spinal planning, digital twin biomechanical simulation, and control of downstream fabrication. The computing platform can communicate with external data sources, such as imaging archives or hospital information systems, through one or more network interfaces, and can provide graphical user interfaces for display of alignment parameters and candidate rod geometries.

In this example, the computing platform is operatively coupled to a manufacturing controller configured to receive candidate device geometries and associated material properties from the planning and simulation modules. The manufacturing controller implements a conditional gating protocol that evaluates whether a stability or safety criterion has been satisfied before any manufacturing instructions are allowed to reach the fabrication device. According to some aspects, the manufacturing controller is further coupled to a hardware isolation subsystem that includes one or more relays, contactors, or equivalent circuitry positioned in the actuation power path of the fabrication device.

In some embodiments, the fabrication device comprises a numerically controlled rod-bending system, an additive manufacturing apparatus, or another programmable device capable of forming spinal fixation rods according to the candidate geometries output by the computing platform. The hardware isolation subsystem maintains the fabrication device in a locked, de-energized state until an authorization signal is issued by the manufacturing controller following successful biomechanical validation. In this example, the overall architecture shown in FIG. 1 enables tight coupling between computational evaluation, cryptographic or logical authorization, and physical actuation, thereby ensuring that only validated geometries are permitted to proceed to fabrication while providing a flexible framework for incorporating future analytical and planning modules.

In some embodiments, FIG. 2 illustrates an anatomical and geometric schema used to characterize lumbopelvic and spinal sagittal alignment. According to some aspects, FIG. 2 depicts a pelvis with an associated pelvic incidence (PI) angle and a series of vertebral pelvic angles extending proximally along the spinal column. In this example, the configuration highlights how pelvic orientation and pelvic incidence (PI) relate to the shape of the spine and to the angular relationship between the sacrum and successive vertebral bodies. FIG. 2 may further emphasize that combinations of vertebral pelvic angles and overall pelvic incidence (PI) can be used to describe a subject's global sagittal profile and regional curvature patterns.

Figure 3:
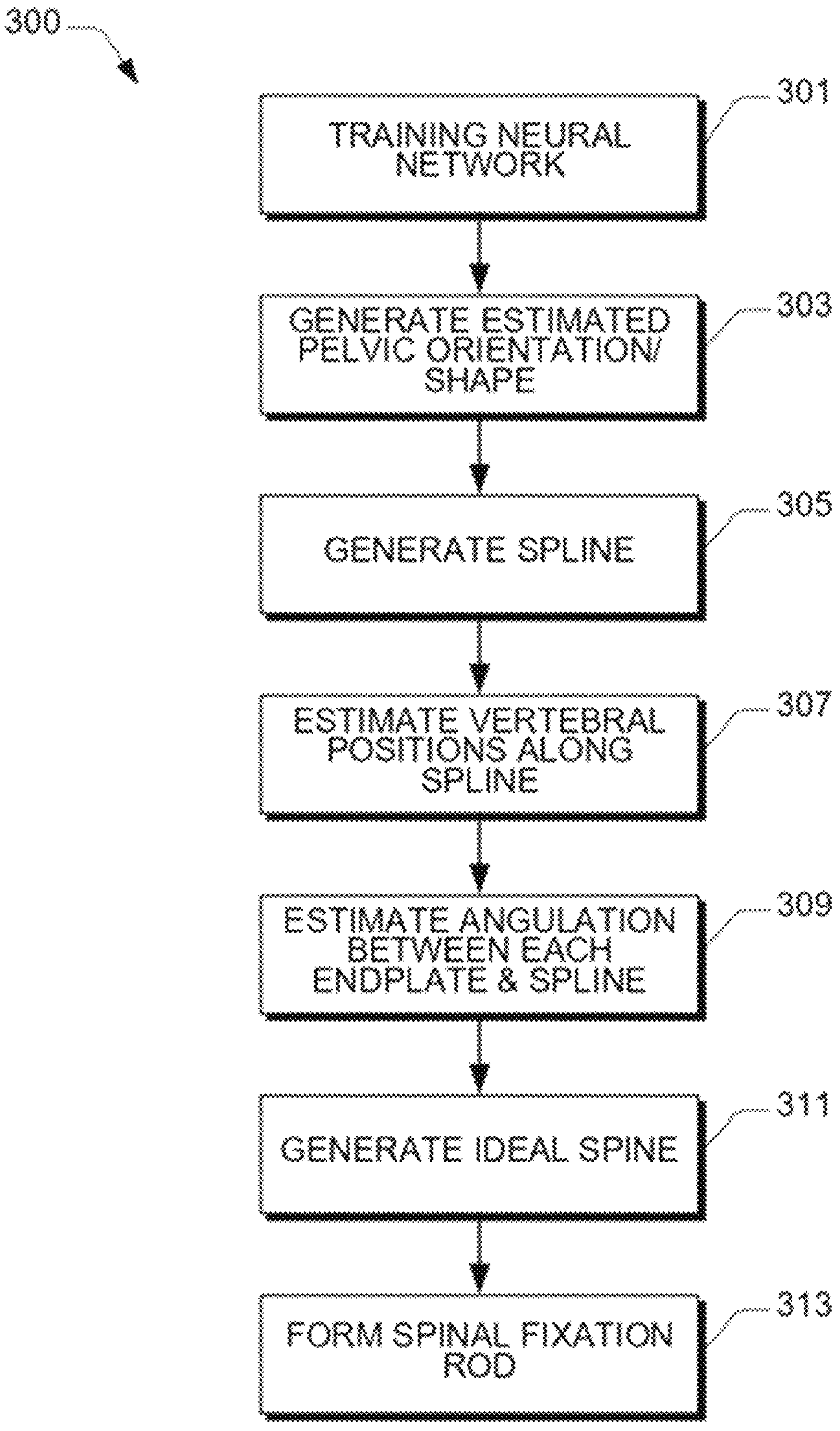
FIG. 3 is a high-level flowchart of the method for training a neural network to form a spinal fixation rod.
Figure 4:
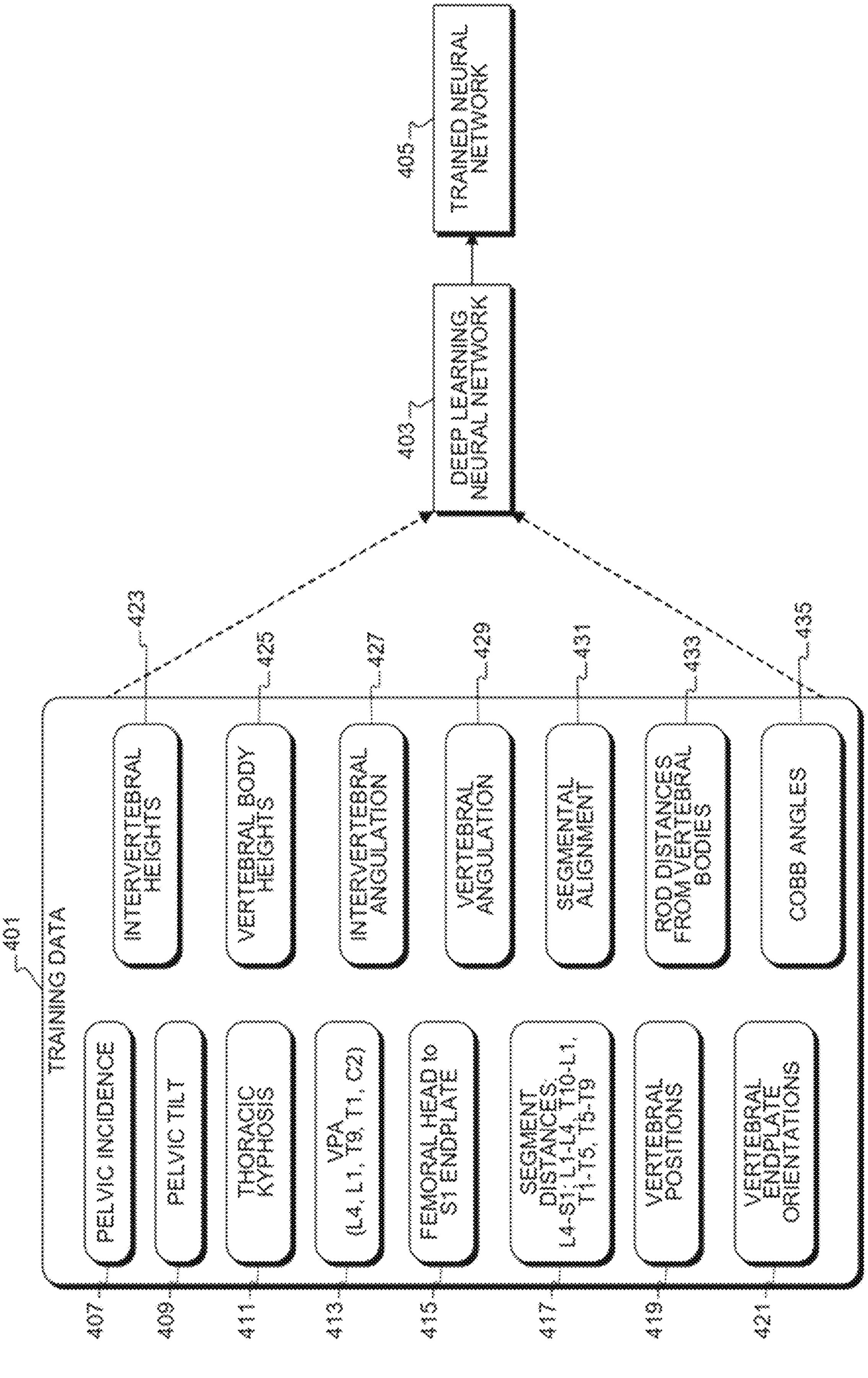
FIG. 4 is a data flow diagram illustrating the inputs (training data) and outputs of the deep learning neural network.

Referring now to FIGS. 3-4, a flowchart illustrates an exemplary method 300 for forming a spinal fixation rod, according to an embodiment. At step 301, a deep learning neural network 403, described in greater detail below, may be trained by a computer based on input data 401 and a selected training algorithm to generate a trained neural network 405. The input data may consist of anatomical parameters, including pelvic incidence 407, pelvic tilt 409, thoracic kyphosis 411 (magnitude and shape), vertebral pelvic angle (VPA) for specific vertebrae 413, distance from a femoral head to an S1 endplate 415, segment distances between specific vertebrae 417, positions of vertebral centers from C2 to S1 419, and orientations of vertebral endplates 421. Input data 401 may also include regional and/or segmental Cobb angles 435.

The training process may involve the use of historical datasets to enhance the accuracy and reliability of the neural network. In some embodiments, historical datasets may include intervertebral height data 423, vertebral body height data 425, intervertebral angulation data 427, vertebral body angulation data 429, segmental alignment data 431 for the segment distances 417. Preferably, historical datasets also include data of spinal fixation rod distances from vertebral bodies 433. These are obtainable from post-operative imaging.

At step 303, the trained network 405 generates an estimated pelvic orientation and shape, then generates a spline 305 based upon the historical data and generally conforming to a human spine shape. Next, step 307 involves estimating vertebral positions along the spline based upon the historical data. The network 405 then estimates the angulation between each vertebral endplate and the spline (Step 309). The trained neural network 405 may then be utilized to generate an ideal full spine shape by combining the estimated angulation and the estimated positions of the vertebrae at step 311. This ideal spine shape may serve as the basis for forming a spinal fixation rod that extends from a patient's T1 vertebra to the pelvis, providing structural support for spinal correction 313.

The method may further include defining thoracic kyphosis using a regression method with an $R^2$ value of at least 0.9 and defining the relationship between pelvic incidence and VPA using a similar regression method. The spinal fixation rod may be formed based on the ideal spine shape, potentially involving the extension of rods from vertebra T1 to the pelvis or from C2 to T1, depending on the specific requirements of the spinal correction.

In some embodiments, FIG. 3 illustrates an exemplary method flow for generating a patient-specific spinal fixation rod design from anatomical data. According to some aspects, the method begins with acquisition of imaging and clinical information, proceeds through extraction of spinal and pelvic parameters, and then applies one or more processing steps to derive alignment descriptors suitable for model input. In this example, subsequent steps include application of a trained model to predict an idealized spinal alignment, evaluation of correction targets, and generation of design data that specify a candidate rod geometry configured to restore the subject toward the predicted alignment.

In some embodiments, FIG. 4 illustrates a data-processing and modeling architecture used to implement alignment prediction and rod design. According to some aspects, FIG. 4 depicts ingestion of historical datasets, feature extraction modules that compute anatomical and alignment parameters, and a modeling component such as a neural network configured to learn relationships between inputs and target alignments. In this example, the architecture further includes an output module that provides predicted alignment parameters and corresponding rod design specifications suitable for downstream manufacturing workflows.

Figure 5:
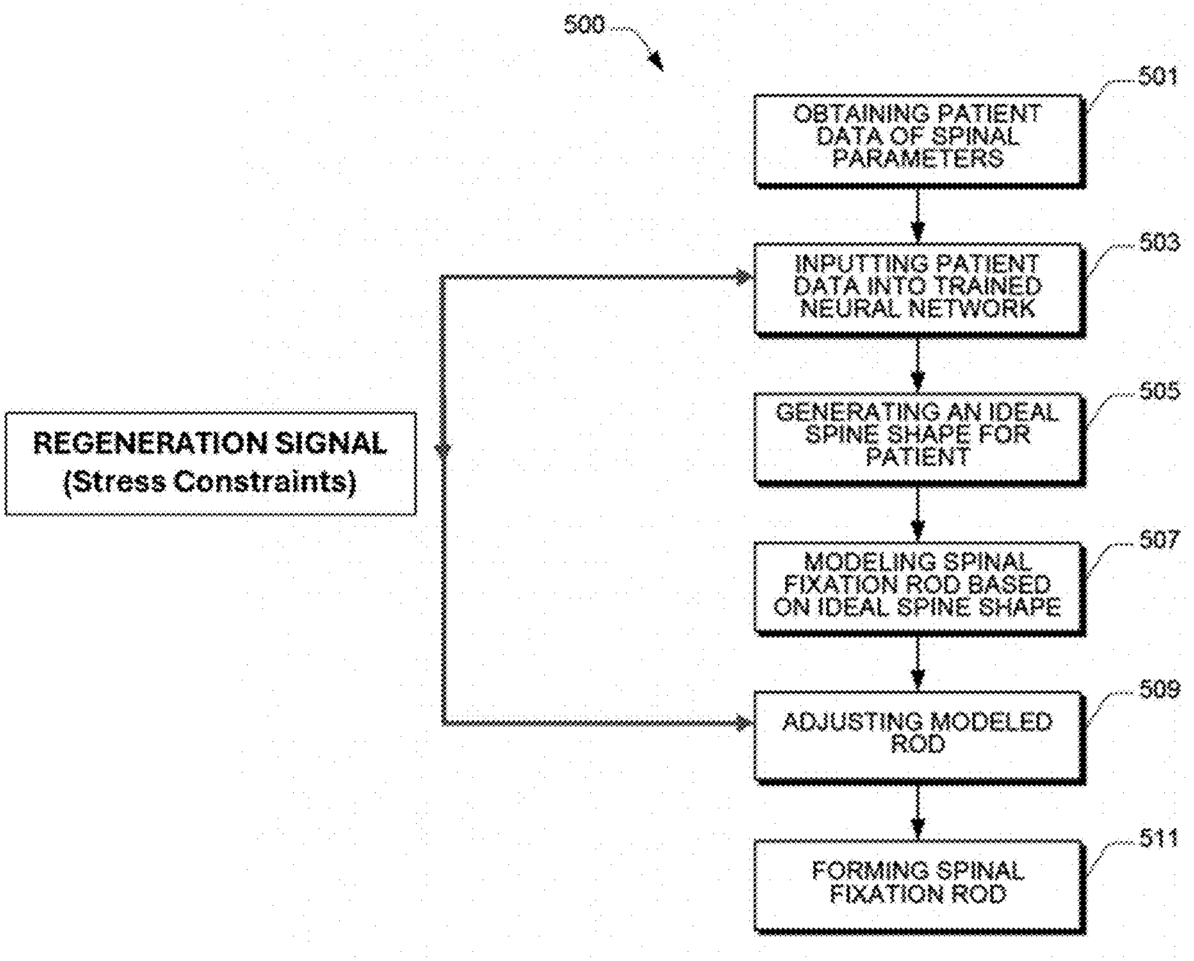
FIG. 5 is a flowchart of an example manufacturing process, highlighting the neuro-physical regeneration loop for validating rod geometry.

FIG. 5 is a flowchart illustrating another exemplary method 500 for forming spinal fixation rods where in step 501 measurement data representing a patient's spinal parameters may be obtained. This data may include anatomical parameters such as pelvic incidence, pelvic tilt, thoracic kyphosis, vertebral pelvic angle (VPA) for specific vertebrae, distance from a femoral head to an S1 endplate, segment distances between specific vertebrae, positions of vertebral centers from C2 to S1, and orientations of vertebral endplates. The data may then be input into a neural network 503 that has been trained on historical datasets of spinal parameters. This trained neural network may generate an ideal spine shape based on the input data 505. Next, a step 507, a model of a spinal fixation rod according to the ideal spine shape is built. The model may be tested using a gravity line biomechanical model, which may predict reciprocal changes above fused vertebral segments and pelvic position in space. This model may account for posterior translation of the spinal rod from the patient's spine, as well as thoracolumbar and cervical alignment, to ensure the patient maintains proper head position and horizontal gaze. The modeled rod may be adjusted based upon the results of testing 509. Finally, the formation of a spinal rod may be based upon the adjusted model 511.

Figure 7:
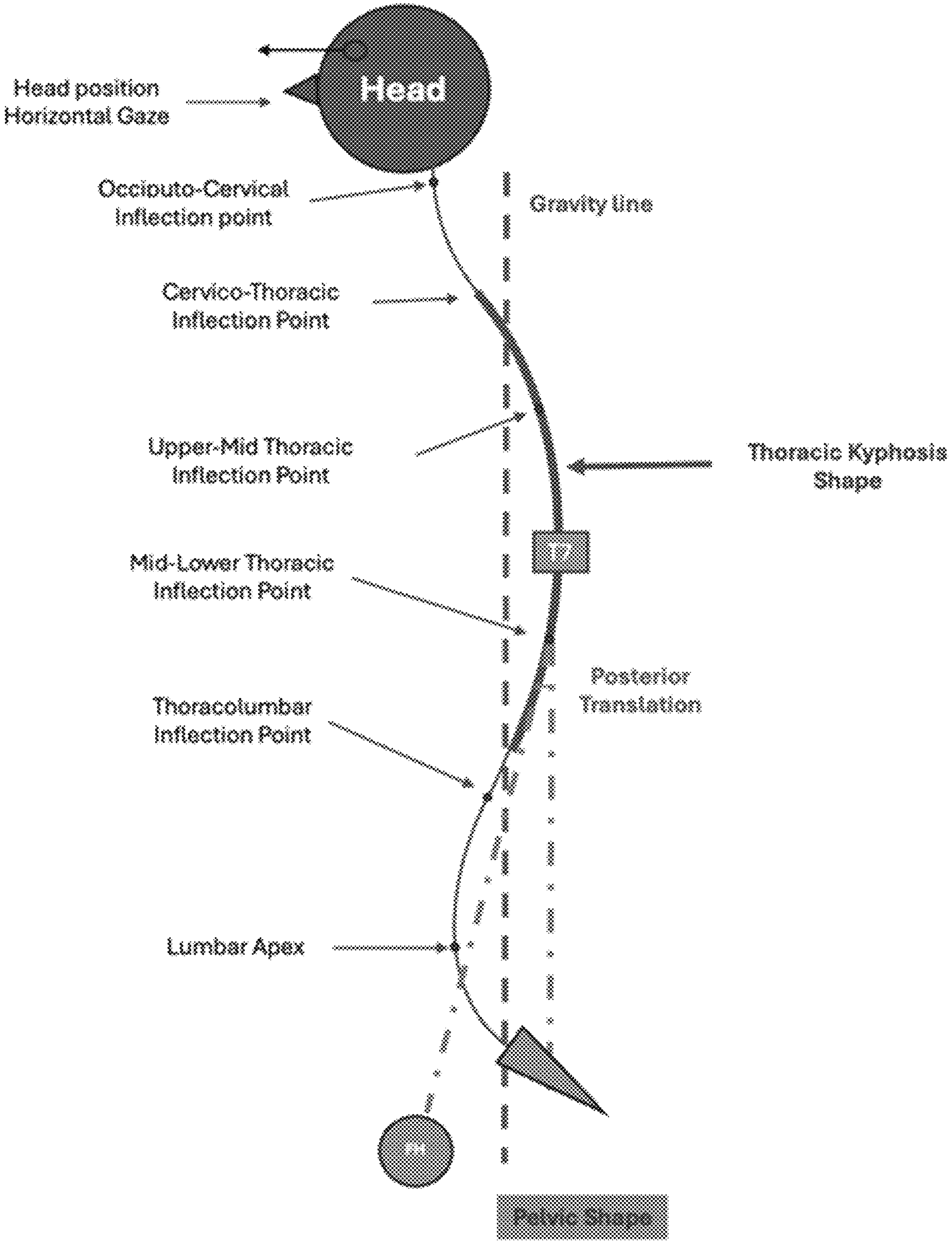
FIG. 7 is a detailed schematic of spinal inflection points and gravity line alignment (gravity line + and − indications are also depicted in FIG. 9).
Figure 9:
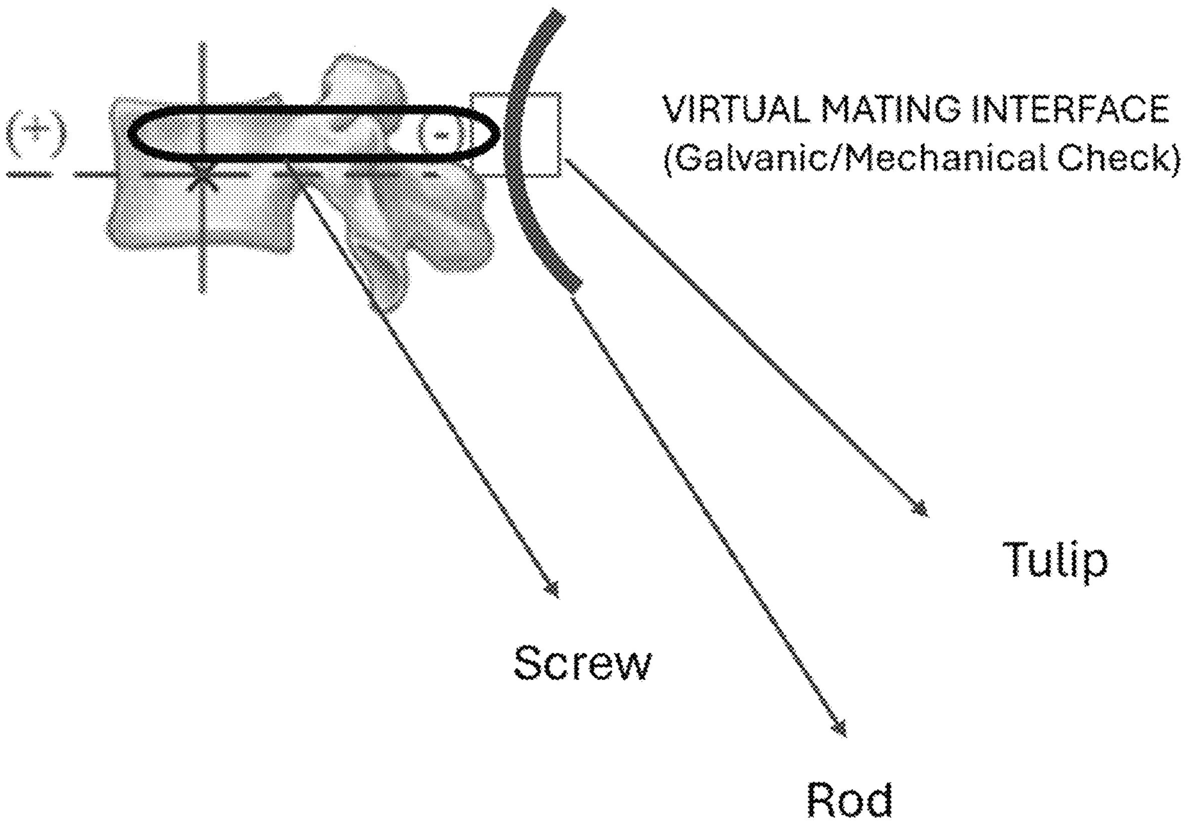
FIG. 9 is, in some embodiments, a schematic representation of the virtual mating interface showing the compatibility check between the rod and a third-party fixation anchor; depicting a virtual mating screen (tulip, rod, interface widgets).

The following is the method used to generate gravity line model. FIG. 9 depicts the sign convention used in determining sagittal offset. The gravity line is also depicted in FIG. 7.

For each of the body segments of interest, the mass was distributed as a percentage (%) of the total mass, and the location of individual centers of mass was based on the literature (Table 1). The center of mass of the head was approximated at the sella turcica. For each vertebra, from T1 to L5, the center of mass was found by locating the center of the vertebral body (FIG. 9: see 'X' and the + and −; the gravity line is also depicted in FIG. 7) and then anteriorly applying the sagittal offset perpendicularly to the central axis of the vertebral body. For the pelvis, the center of mass was located at 59.6% of the length of the line from the sacral plate to the femoral heads. The center of mass of the femur was located at 36.14% of the length of the line from the femoral head to the center of the knee. Finally, the center of mass of the tibia was found at 43.5% of the length of the line between the center of the knee to the middle of the lower end of the tibia.

TABLE 1

Mass Percentage and Offset for each segment.

| Segment | Mass (%) | Center Of Mass Location |
|---|---|---|
| Head | 6.668 | Approximated at the Sella Turcica |
| T1 | 1.1 | 8 mm, anterior to the midpoint of the vertebral central axis |
| T2 | 1.1 | 13 mm, anterior to the midpoint of the vertebral central axis |
| T3 | 1.4 | 20 mm, anterior to the midpoint of the vertebral central axis |
| T4 | 1 | 28 mm, anterior to the midpoint of the vertebral central axis |
| T5 | 1.3 | 34 mm, anterior to the midpoint of the vertebral central axis |
| T6 | 1.3 | 39 mm, anterior to the midpoint of the vertebral central axis |
| T7 | 1.4 | 43 mm, anterior to the midpoint of the vertebral central axis |
| T8 | 1.5 | 46 mm, anterior to the midpoint of the vertebral central axis |
| T9 | 1.6 | 46 mm, anterior to the midpoint of the vertebral central axis |
| T10 | 2 | 46 mm, anterior to the midpoint of the vertebral central axis |
| T11 | 2.1 | 44 mm, anterior to the midpoint of the vertebral central axis |
| T12 | 2.5 | 41 mm, anterior to the midpoint of the vertebral central axis |
| L1 | 2.4 | 35 mm, anterior to the midpoint of the vertebral central axis |
| L2 | 2.4 | 27 mm, anterior to the midpoint of the vertebral central axis |
| L3 | 2.3 | 18 mm, anterior to the midpoint of the vertebral central axis |
| L4 | 2.6 | 11 mm, anterior to the midpoint of the vertebral central axis |
| L5 | 2.6 | 4 mm, anterior to the midpoint of the vertebral central axis |
| Pelvis | 10.7 | 59.6% of the length of the line from the Sacral plate to the Femoral Heads |
| Femur | 24.43 | 36.14% of the length of the line from the Femoral head to the center of the Knee |
| Tibia | 9.31 | 43.5% of the length of the line between the center of the Knee to the middle of the lower end of the Tibia |

According to some aspects, Table 1 describes a Mass Percentage and Offset for each segment—for the trunk and lower extremities.

Figure 6:
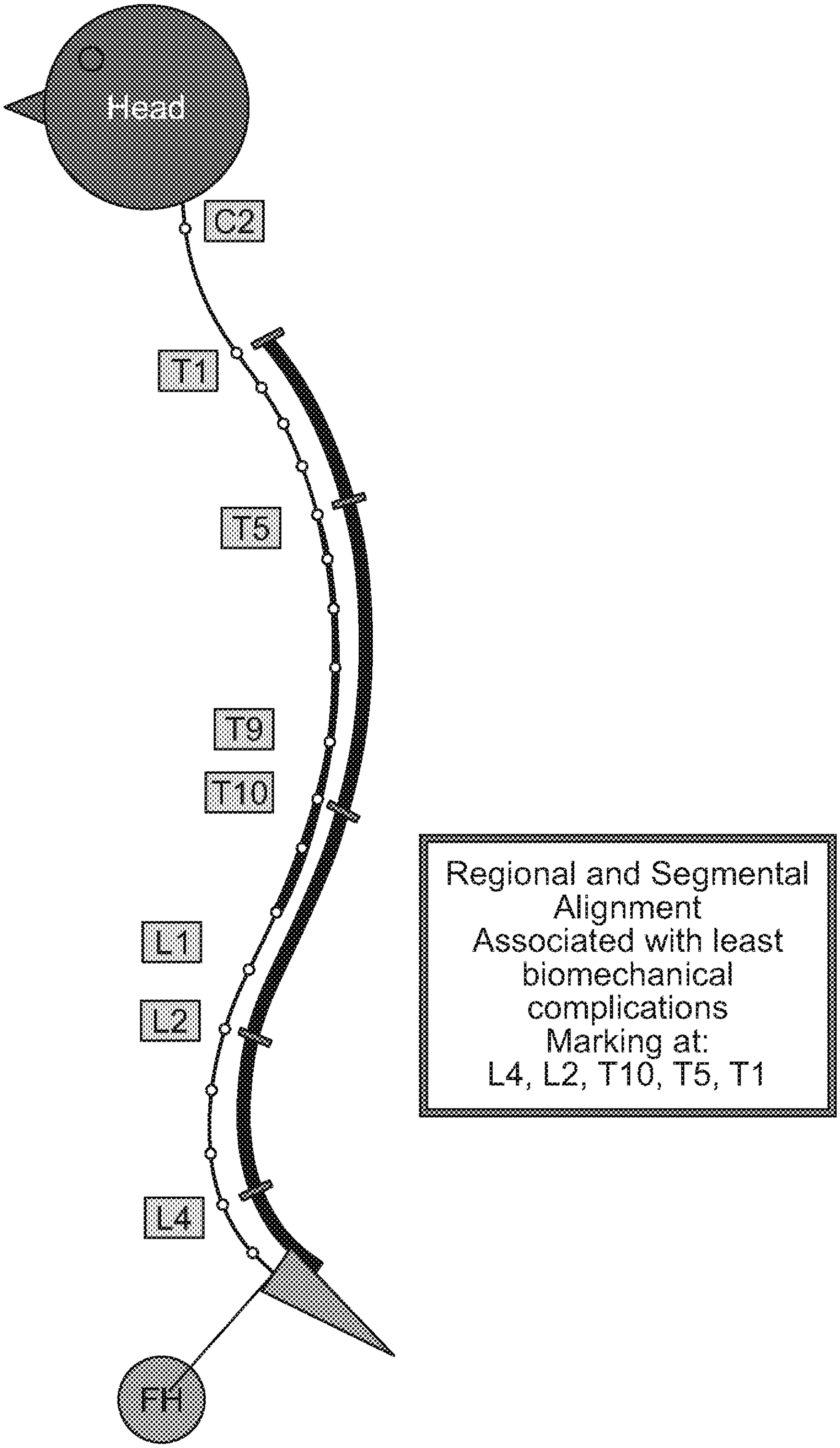
FIG. 6 is a diagram illustrating regional and segmental alignment markings on a generated spinal curve.

In some embodiments, FIG. 6 illustrates regional and segmental spinal alignment patterns associated with a reduced likelihood of biomechanical complications. According to some aspects, FIG. 6 depicts a spinal column with emphasis on discrete vertebral levels used as reference landmarks for planning, including lumbar vertebra L4 and L2 and thoracic vertebrae T10, T5, and T1. In this example, FIG. 6 highlights how regional alignment, such as lumbar and thoracic curvature, can be decomposed into segmental contributions defined between these landmarks. Segmental alignment values may be associated with specific ranges that correspond to clinically favorable loading distributions across fused and adjacent motion segments. According to some aspects, FIG. 6 further suggests that appropriate selection of target regional and segmental alignment at the indicated vertebral levels can reduce stress concentrations and abrupt angular transitions, thereby contributing to constructs that exhibit more favorable biomechanical behavior over time.

After finding the location of the centers of mass of individual segments, the coordinates of the total center of mass were calculated using the formula:

$$R = \left(\frac{1}{M}\right)\sum_{i=1}^{n} m_i r_i$$

where M as the sum of all masses, m with the individual masses and r the coordinates of the individual center of masses. The gravity line (shown in FIG. 9 and also in FIG. 7) was found by vertically projecting the calculated center Of mass (COM).

In another embodiment, the contours of the spinal rod may be optimized using a finite element model to predict complications at junctions between fused and unfused vertebrae, minimizing the likelihood of proximal junctional kyphosis and failure. The finite element model may also predict the impact of rod stiffness, fixation techniques, and the ideal shape on adjacent segment loading, as well as the influence of different spinal rod materials and hybrid rods on biomechanics. Additionally, it may predict interactions of patient soft tissue with the rods over time and spinal rod fatigue-related failure at junctional zones. This comprehensive approach may ensure that the spinal rod is tailored to the patient's specific anatomical and biomechanical needs, potentially improving the outcomes of spinal correction procedures.

A spinal rod formed by the method described may include regions that correspond to the patient's segment distances between specific vertebrae, such as L4-S1, L1-L4, T10-L2, T5-T9, and T1-T5. These regions may be visually indicated on the spinal rod, providing a clear representation of the segment distances. Additionally, angulation inflection points may also be visually marked on the spinal rod, allowing for precise alignment and correction of spinal deformities. This design ensures that the spinal rod is tailored to the patient's unique anatomical structure, potentially enhancing the effectiveness of spinal correction procedures.

In some embodiments, FIG. 7 illustrates spinal inflection points and their relationship to global sagittal alignment. According to some aspects, FIG. 7 depicts a spinal curve extending from the pelvis to the head, with labeled inflection points at occipito-cervical, cervico-thoracic, upper-mid thoracic, mid-lower thoracic, and thoracolumbar transition regions. In this example, a gravity line is shown relative to the spinal curve, as well as a representation of posterior translation and a lumbar apex. FIG. 7 emphasizes how the positions of these inflection points, together with pelvic shape and head position, define thoracic kyphosis shape and overall sagittal balance, thereby providing a framework for selecting alignment targets that maintain horizontal gaze and physiologic posture.

Figure 8:
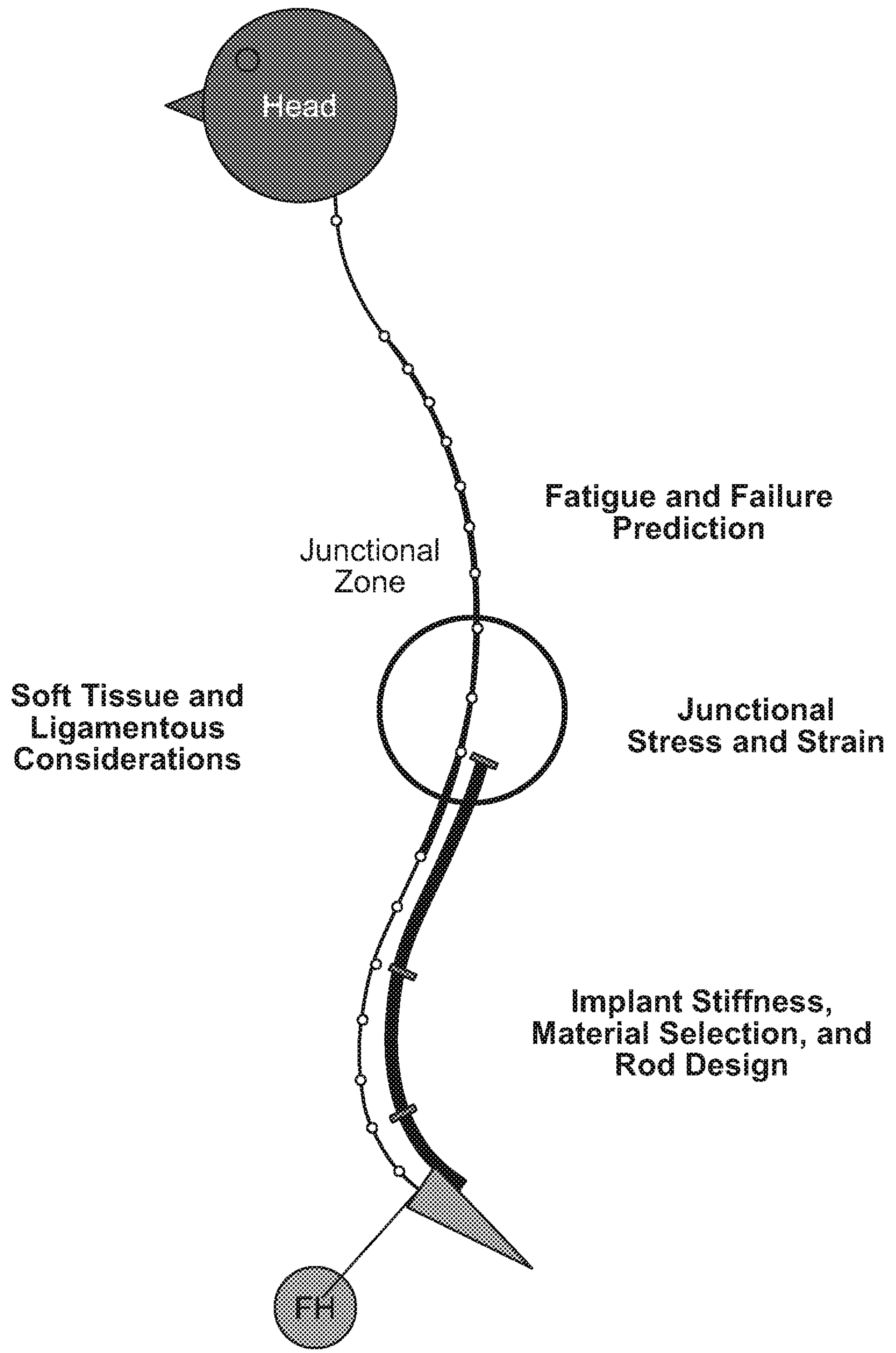
FIG. 8 is a diagram illustrating the biomechanical validation parameters, including junctional stress and fatigue prediction.

In some embodiments, FIG. 8 illustrates biomechanical validation parameters used to evaluate spinal constructs, with emphasis on junctional behavior. According to some aspects, FIG. 8 schematically identifies a junctional zone and summarizes factors such as junctional stress and strain, soft tissue and ligamentous considerations, implant stiffness, material selection, and rod design. In this example, FIG. 8 conceptually groups these factors under "fatigue and failure prediction" to indicate that long-term construct performance depends on combined effects of local loading patterns, adjacent soft-tissue support, and mechanical properties of the implants at and near junctional regions.

In some embodiments, FIG. 9 illustrates a virtual mating interface configured to evaluate mechanical and electrochemical compatibility between a generated spinal fixation rod and a selected third-party fixation anchor system. According to some aspects, FIG. 9 schematically depicts a rod, a tulip head, and an associated screw arranged within a digital twin environment labeled as a galvanic and mechanical check. The virtual mating interface can simulate rod seating within the tulip channel, tulip closure, and engagement of a locking element, while tracking clearances, seating depth, and available set-screw travel. In this example, the interface can further compute contact pressure distributions, potential bottom-out scenarios, and angle constraints relative to the polyaxial range of motion envelope. Galvanic compatibility may be evaluated by combining material information for the rod and fixation components with exposure conditions representative of a physiological environment. The overall representation in FIG. 9 provides a conceptual view of an interoperability layer that confirms that a candidate rod geometry not only meets spinal alignment and biomechanical targets, but also mates safely with specific third-party fixation components before authorization for fabrication.

Figure 10:
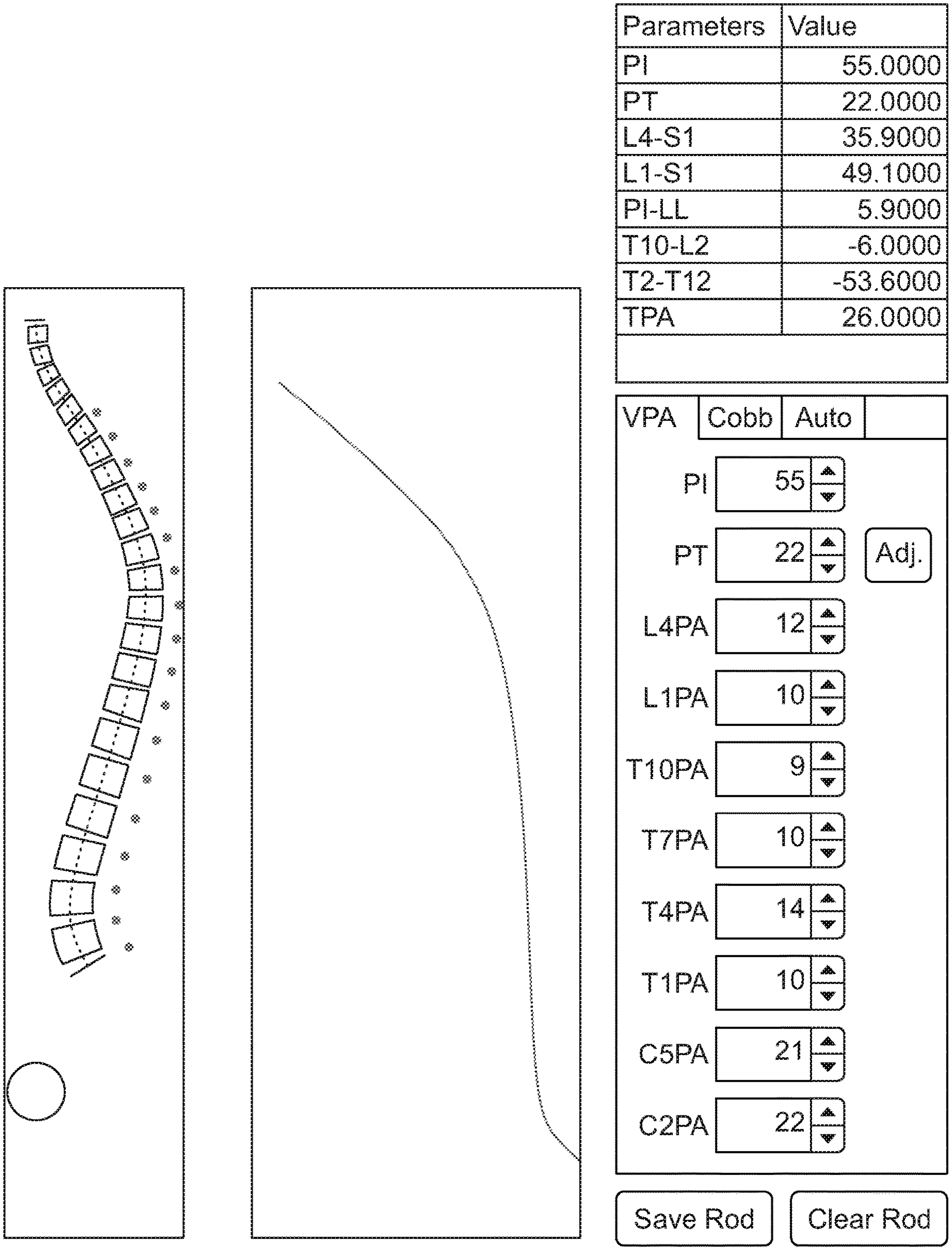
FIG. 10 is a graphical user interface (GUI) displaying the candidate rod geometry and patient-specific parameters.

In some embodiments, FIG. 10 illustrates a graphical user interface configured to present patient-specific parameters and a corresponding candidate rod plan. According to some aspects, the user interface displays a table of key alignment and anatomical parameters, including pelvic incidence, pelvic tilt, lumbar segment distances, and regional angular relationships such as pelvic incidence minus lumbar lordosis and thoracic sagittal measures. Numerical fields may accept input from preoperative imaging measurements, automated extraction pipelines, or derived planning values. In this example, the interface further includes controls such as "Save Rod" and "Clear Rod," enabling storage of a candidate design in association with the displayed parameter set or clearing of a working proposal. The arrangement shown in FIG. 10 supports transparent review of the parameter set driving a particular candidate rod geometry, and provides a platform for integration with downstream biomechanical validation, interoperability checks, and manufacturing authorization workflows.

Figure 11:
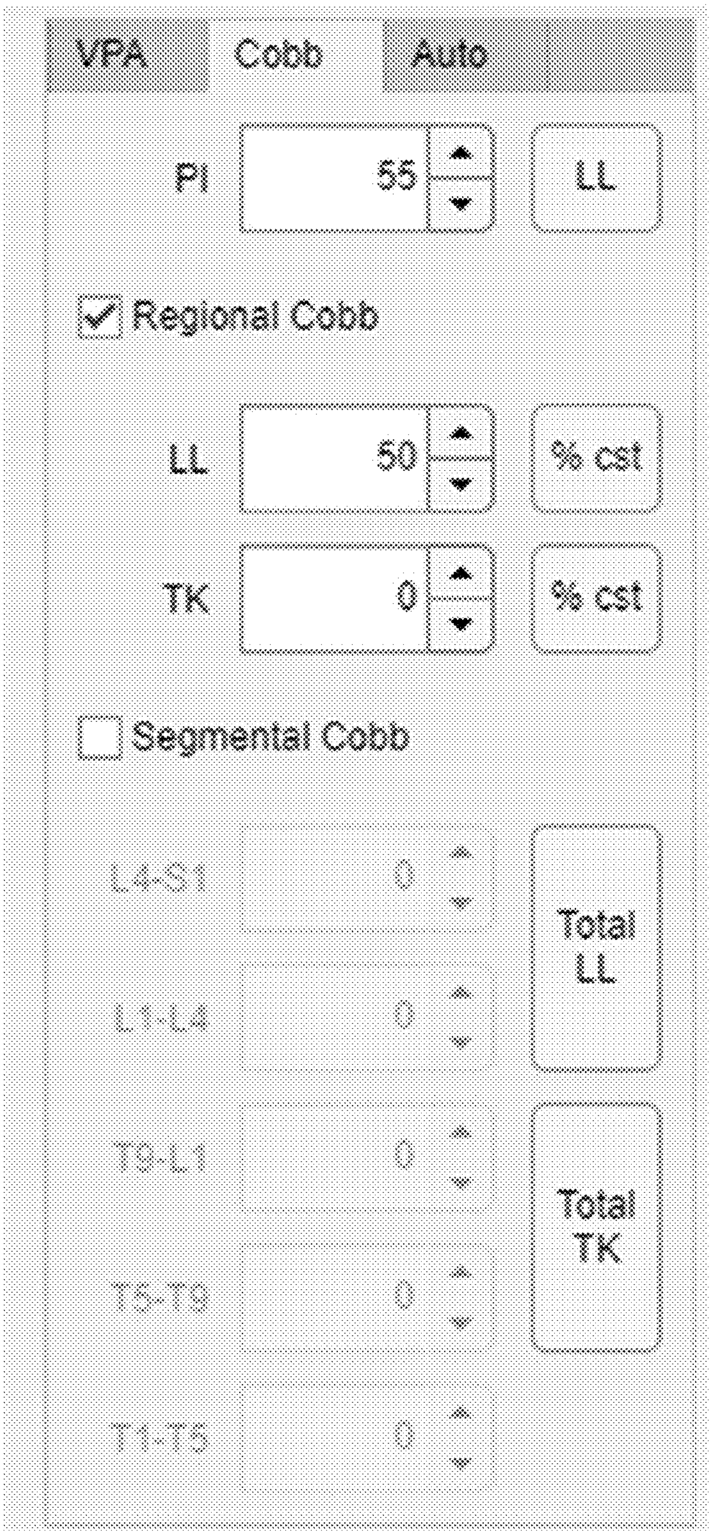
FIG. 11 is a graphical user interface (GUI) displaying Cobb angle adjustments and segmental alignment controls.

In some embodiments, FIG. 11 illustrates a graphical user interface configured to adjust Cobb angles and segmental alignment targets in a structured and interactive manner. According to some aspects, FIG. 11 presents controls for vertebral pelvic angle Cobb values and regional Cobb angles, including pelvic incidence-lumbar lordosis relationships, thoracic kyphosis values, and other regional descriptors. A segmental Cobb section provides fields or controls for individual segments or short spinal regions, allowing refinement of local curvature while preserving or rebalancing global alignment targets. In this example, the interface may display a "Total" alignment summary derived from the regional and segmental entries, along with an option for automatic adjustment that harmonizes entries with predefined alignment guidelines or regression-based targets. FIG. 11 thereby represents a planning environment in which regional and segmental Cobb angles can be tuned, visualized, and coordinated, providing structured inputs for subsequent prediction of an ideal full-spine shape and specification of a corresponding spinal fixation rod geometry.

Figure 12:
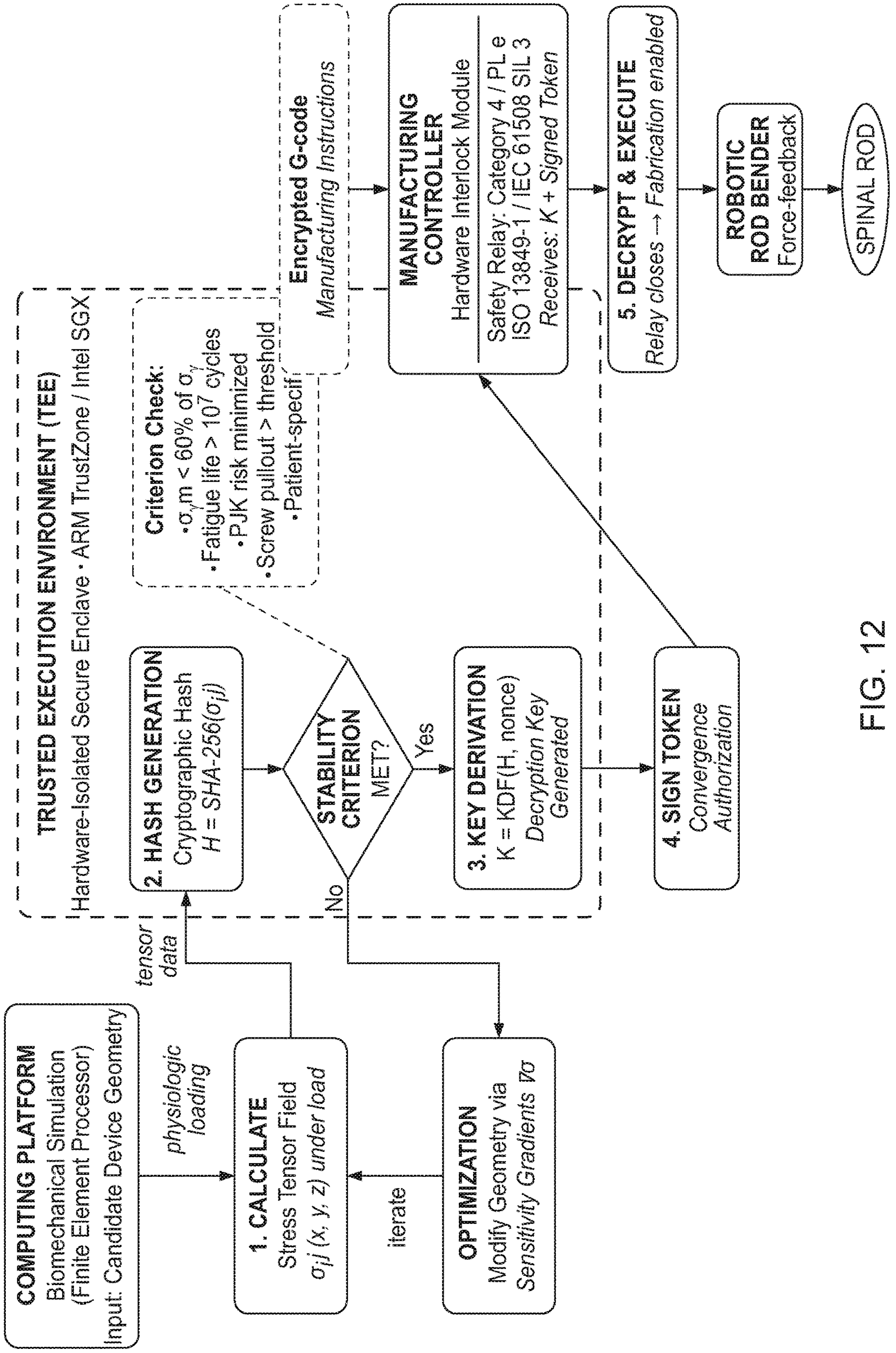
FIG. 12 is a logic flow diagram illustrating the cryptographic generation of the decryption key from the stress tensor field hash, identifying the trusted execution environment (TEE) and the dependency on the stability criterion.

In some embodiments, FIG. 12 depicts key security properties; for example; cryptographic Binding: The decryption key K is derived from the stress tensor hash H—fabrication of any unvalidated geometry is cryptographically impossible since the key cannot exist without a passing stress analysis. TEE Isolation: Key derivation logic executes within hardware-isolated enclave (ARM TrustZone/Intel SGX), preventing tampering or bypass via software exploits. Hardware Interlock: Safety relay (Cat 4/PL e) physically breaks actuator power circuit; relay coil energizes only upon cryptographic validation of convergence token. Non-Bypassable: Manual override commands are intercepted and discarded; UI widgets rendered in deactivated state until authorization received. Audit Trail: Immutable log captures all locked→unlocked state transitions with timestamps, criterion values, and tensor hashes for regulatory compliance (e.g., 21 CFR Part 11). In another example, a spinal construct generated by spinal rods will undergo multi-objective optimization and genetic algorithms through a multi-objective optimization framework combining neural networks with genetic algorithms to optimize spinal rod geometry, balancing multiple competing objectives like biomechanics, patient-specific comfort, flexibility, fatigue resistance, and minimal stress concentrations.

In some embodiments, FIG. 12 illustrates a cryptographically gated control architecture that couples biomechanical simulation outputs to hardware-level manufacturing authorization. The diagram depicts a flow beginning with a computing platform that executes digital twin biomechanical validation and stress analysis of a candidate spinal fixation rod geometry. Within this platform, a simulation engine computes a stress tensor field under physiologic loading and evaluates whether a stability criterion, such as limits on von Mises stress and minimum fatigue life, has been satisfied.

According to some aspects, FIG. 12 identifies a trusted execution environment (TEE) into which the stress tensor field summary and stability criterion results are passed. Within the TEE, key-derivation logic computes a cryptographic hash of the stress tensor field and associated metadata, and derives a decryption key only when the stability criterion is met. In this example, the TEE may be implemented using a hardware-backed enclave such as ARM TrustZone or Intel SGX, isolating the key derivation path from the main operating system and preventing tampering, replay, or software-level bypass of the convergence requirements. The diagram emphasizes that the decryption key is mathematically bound to the stress tensor hash so that no valid key can exist in the absence of a passing biomechanical analysis.

In some embodiments, the derived key and an associated convergence authorization token are transmitted from the TEE to a hardware-interlocked manufacturing controller. FIG. 12 depicts this controller as enforcing a hardware isolation state, for example by driving a safety relay or equivalent isolation circuit that physically de-energizes the fabrication actuation mechanism of a rod-bending or other fabrication device. Only upon successful cryptographic validation of the convergence token does the controller transition from a locked state to a fabrication-enabled state, permitting manufacturing instructions to be decrypted and executed. The logic flow further indicates interception of manual override and user-interface actuation signals while the system remains locked, such that software settings, surgeon commands, or emergency button presses cannot bypass the cryptographic gate.

In this example, FIG. 12 also schematically includes an immutable audit trail coupled to the manufacturing controller. Each transition from locked to unlocked state, together with identifiers of the validated rod geometry, stability-criterion values, and stress-tensor hash, is recorded for regulatory and quality-assurance purposes, such as compliance with electronic records requirements. The overall arrangement shown in FIG. 12 visually integrates the computing platform, TEE-based key derivation, hardware interlock circuitry, and fabrication device into a single trusted execution and enforcement pipeline, ensuring that only digitally verified, biomechanically converged rod geometries can proceed to physical manufacture. The system may integrate predictive modeling that dynamically forecasts patient-specific spine evolution and potential complications over long-term follow-ups (5, 10, 15 years). Use sequential deep learning models such as Transformer-based architectures or attention mechanisms to process longitudinal patient data.

The system may also employ digital twin technology to replicate each patient's spine digitally, capturing dynamic interactions between soft tissues, bones, and implants. Regularly updating digital twins with patient data post-operation could refine predictive accuracy and adaptability over time.

Quantum-inspired computational techniques, like quantum annealing or quantum machine learning methods, may be deployed to navigate complex, multidimensional optimization spaces more effectively, potentially leading to superior biomechanical outcomes.

In some embodiments, the system may be configured with a real-time intraoperative monitoring system leveraging augmented reality (AR) and sensor-fused implants that provide feedback to surgeons during implantation, dynamically adjusting the rod's shape intraoperatively based on neural network predictions and finite element simulations.

The rods formed by the disclosed method may be formed from smart materials such as shape memory alloys (SMAs) or magnetorheological (MR) elastomers within rod designs. These could allow for postoperative adjustments through non-invasive external stimuli (temperature, magnetic fields, electric signals), adapting spinal support dynamically post-implantation.

The method may also make use of patient-specific coatings on the spinal rods tailored to individual patient's biochemistry, delivering anti-inflammatory or bone-growth enhancing pharmaceuticals at specified times post-surgery, potentially improving healing and reducing complications.

Spinal rods and associated spinal constructs (interbody devices, pedicle screws) as well as postoperative management strategies may be optimized dynamically via machine learning predictive maintenance models that alert physicians and patients of potential structural weakening or failures in rods, anticipating the need for intervention or replacement proactively, thus preventing catastrophic failures. In addition, a centralized cloud-based platform for aggregating anonymized, longitudinal spinal implant data, may be developed for promoting continuous learning and model improvement through federated learning techniques, which respects patient privacy while significantly enhancing global spinal treatment standards.

In some embodiments, a spinal rod generated by the above-described methods will be associated with optimal pedicle screw insertion and that will be defined through neural network and computer software. Spinal rod will dictate inter body devices shape (lordosis/kyphosis/height) that is associated with obtaining the spinal shape generated by the rod.

In other embodiments, interbody devices will follow the same alignment processes used to generate the rod. Spinal rod and inter body devices will be tested with FEM, digital twins and Artificial intelligence to stimulate real world scenarios of patients with variable muscle, bone and ligament quality as well as patient demographics and comorbidities. Spinal rod, screws trajectories, inter body devices will comprise "the construct" that eventually will be fully tested in neural network using parameters from dataset that are associated with the least biomechanical complications and most durable outcomes.

Only a few examples and implementations are disclosed. Variations, modifications, and enhancements to the described examples and implementations and other implementations can be made based on what is disclosed.

Further in a discussion, writing, claiming, study or a reading of the details, features, embodiments, aspects, any figure or any part of any figure, and/or examples of the technology disclosed herein, any of the features, embodiments, aspects, and/or examples herein can be optionally inter-combined (or inter-discussed) with the example details listed below, and any portion (or aspect) of any detail below can be inter-combined with any portion of any feature or example disclosed herein:

Detail 1: A method of designing a spinal fixation rod for treatment of a spinal deformity in a subject, the method comprising the steps of: (a) training, by one or more processors, a neural network using historical post-operative data comprising: anatomical parameters of prior subjects, post-operative spinal alignment parameters, and distances between implanted spinal fixation rods and vertebral bodies obtained from post-operative imaging; (b) receiving, by the neural network, patient-specific anatomical parameters for the subject, the patient-specific anatomical parameters comprising at least pelvic incidence, pelvic tilt, vertebral pelvic angle, and one or more thoracic or lumbar curvature parameters; (c) processing, by the trained neural network, the patient-specific anatomical parameters to generate an estimated ideal spine shape for the subject; and (d) determining, based on the estimated ideal spine shape, a patient-specific spinal fixation rod geometry configured to restore the subject's spine toward the estimated ideal spine shape.

Detail 2: The method of detail 1, wherein the historical post-operative data further comprise clinical outcome data obtained at least two years after surgery, and the training of the neural network includes correlating the anatomical parameters and distances between vertebral bodies and implanted rods with the clinical outcome data.

Detail 3: The method of detail 1, wherein the patient-specific anatomical parameters further comprise: a) segmental distances between vertebrae including at least one of: L4-S1, L1-L4, T10-L1, T5-T9, and T1-T5; b) positions of vertebral centers from C2 to S1; and c) orientations of vertebral endplates.

Detail 4: The method of detail 1, wherein generating the estimated ideal spine shape comprises generating, by the trained neural network, a continuous spinal curve represented as a spline defined at least in part by the pelvic incidence, pelvic tilt, vertebral pelvic angle, and the segmental distances.

Detail 5: The method of detail 1, wherein processing the patient-specific anatomical parameters further comprises generating, by the trained neural network, an estimated pelvic orientation in space based on the pelvic incidence, the vertebral pelvic angle, and data of distance from a femoral head to an S1 endplate.

Detail 6: The method of detail 4, wherein the trained neural network further generates estimated positions of vertebral bodies along the spline based at least in part on the positions of the vertebral centers.

Detail 7: The method of detail 4, wherein the trained neural network further generates segmental angulation values between adjacent vertebrae along the spline based at least in part on the vertebral pelvic angle and the orientations of the vertebral endplates.

Detail 8: The method of detail 1, wherein the thoracic curvature parameters comprise both a thoracic kyphosis magnitude and a thoracic kyphosis shape characterization, and the neural network is trained to predict a thoracic kyphosis profile that satisfies a regression relationship between pelvic incidence and at least one vertebral pelvic angle or sagittal alignment parameter.

Detail 9: The method of detail 1, further comprising modeling the estimated ideal spine shape using a gravity-line biomechanical model that represents centers of mass of trunk and lower-extremity body segments to predict changes in spinal alignment above fused vertebral segments and pelvic position in space.

Detail 10: The method of detail 9, further comprising adjusting the estimated ideal spine shape based on a location of an overall body center of mass and a sagittal offset determined from the gravity-line biomechanical model, and updating the patient-specific spinal fixation rod geometry based on the adjusted ideal spine shape.

Detail 11: The method of detail 1, further comprising performing a finite element analysis of a spinal construct including the patient-specific spinal fixation rod geometry and at least a portion of the subject's spinal column, and iteratively modifying the rod geometry to reduce at least one of rod stress concentration, junctional stress, or predicted rod fatigue-related failure.

Detail 12: The method of detail 1, wherein determining the patient-specific spinal fixation rod geometry comprises defining a rod contour and a variable stiffness profile along a length of the rod such that a proximal rod portion and a distal rod portion have different diameters and/or material properties derived from the estimated ideal spine shape.

Detail 13: The method of detail 1, further comprising displaying, on a graphical user interface, an image of at least a portion of the subject's spine with an overlay of the estimated ideal spine shape and an overlay of the patient-specific spinal fixation rod geometry to enable pre-operative planning.

Detail 14: The method of detail 1, wherein the patient-specific spinal fixation rod geometry is configured so that one or more rods extend from vertebra T1 to the pelvis or from vertebra C2 to vertebra T1, as determined from the estimated ideal spine shape.

Detail 15: The method of detail 1, further comprising updating the historical post-operative data with follow-up imaging and clinical outcome data from additional subjects treated using spinal fixation rods designed by the neural network, and periodically retraining the neural network using the updated historical post-operative data to improve prediction of the estimated ideal spine shape.

Detail 16: A method of manufacturing a patient-specific spinal fixation rod that is interoperable with a third-party fixation anchor system, the method comprising the steps of: (a) receiving, by a computing platform, a set of patient-specific anatomical parameters; (b) receiving, by the computing platform, a target fixation profile identifying a specific third-party fixation anchor system intended for implantation, the target fixation profile comprising geometric and material constraint data for the third-party fixation anchor system; (c) generating, by the computing platform, a candidate rod geometry based at least in part on the patient-specific anatomical parameters; (d) executing, by the computing platform, a virtual mating simulation that mates the candidate rod geometry with the target fixation profile to compute an interface stress state that quantifies mechanical mismatch risks between the candidate rod geometry and the third-party fixation anchor system; (e) maintaining, by a hardware-interlocked manufacturing controller communicatively coupled to a physical fabrication device, a locked state that physically prevents the fabrication device from executing manufacturing instructions corresponding to the candidate rod geometry; (f) generating, by the computing platform, an interoperability authorization signal only when the interface stress state satisfies a compatibility threshold defined for the target fixation profile; and (g) transitioning, by the hardware-interlocked manufacturing controller, from the locked state to an unlocked state permitting execution of the manufacturing instructions for the candidate rod geometry only in response to the interoperability authorization signal.

Detail 17: The method of detail 16, wherein the target fixation profile is retrieved from a Fixation Component Library comprising digital twin definitions of a plurality of commercially available fixation anchors, each digital twin including at least tulip head geometry, locking set-screw thread pitch, polyaxial range-of-motion limits, and material yield strength.

Detail 18: The method of detail 16, wherein executing the virtual mating simulation comprises performing a multiphysics interface simulation that models at least (i) contact mechanics between a rod surface and a tulip head channel, and (ii) tribological behavior including friction and wear at the rod-anchor interface.

Detail 19: The method of detail 16, wherein generating the candidate rod geometry comprises generating, by a generative artificial intelligence module trained on historical spinal alignments, an initial candidate rod geometry, and wherein the virtual mating simulation outputs one or more interface constraints that are used as inputs to regenerate or modify the candidate rod geometry to improve compatibility with the target fixation profile.

Detail 20: The method of detail 16, wherein the compatibility threshold includes a polyaxial range-of-motion constraint requiring that an angle between the candidate rod geometry at an entry region into a tulip head and a screw axis of the third-party fixation anchor system is less than a maximum polyaxial angle specified in the target fixation profile.

Detail 21: The method of detail 16, wherein maintaining the locked state comprises at least one of: electrically de-energizing a fabrication actuation circuit of the physical fabrication device; or withholding a cryptographic decryption key required to transmit manufacturing instructions to the physical fabrication device.

Detail 22: The method of detail 16, further comprising evaluating, by the computing platform, a spinal biomechanical stability criterion for the candidate rod geometry, and wherein the hardware-interlocked manufacturing controller is configured to prevent transition to the unlocked state unless both the compatibility threshold and the spinal biomechanical stability criterion are satisfied.

Detail 23: The method of detail 16, wherein the interface stress state comprises one or more of: (i) a prediction of tulip head bottom-out or loss of set-screw travel margin, (ii) a maximum contact stress at the rod-tulip interface relative to an anchor material yield strength, and (iii) a slip-force resistance metric quantifying a force required for the rod to slip within the tulip head.

Detail 24: The method of detail 16, further comprising executing the virtual mating simulation for a plurality of candidate third-party fixation anchor systems, comparing the respective interface stress states to corresponding compatibility thresholds, and selecting, by the computing platform, a recommended fixation anchor system that satisfies the compatibility threshold with the candidate rod geometry.

Detail 25: The method of detail 24, further comprising generating labeling data for the manufactured patient-specific spinal fixation rod, the labeling data identifying at least one third-party fixation anchor system for which the virtual mating simulation verified compatibility under the compatibility threshold.

Detail 26: The method of detail 16, further comprising generating, by the computing platform, a graphical user interface that displays a virtual mating visualization of the candidate rod geometry within a digital twin of the third-party fixation anchor system, the visualization highlighting regions of predicted mechanical conflict or excessive interface stress.

Detail 27: The method of detail 16, wherein the compatibility threshold includes a galvanic corrosion index based on material composition data of the candidate rod geometry and the third-party fixation anchor system, and wherein the interoperability authorization signal is generated only when the galvanic corrosion index is below an anchor-specific limit.

Detail 28: The method of detail 16, further comprising applying the virtual mating simulation to a plurality of pre-contoured rod geometries in an inventory and recording, for each pre-contoured rod, a set of third-party fixation anchor systems for which the compatibility threshold is satisfied, thereby generating an inventory of pre-validated interoperable rods.

Detail 29: The method of detail 16, wherein the target fixation profile specifies a construct comprising fixation anchors from at least two different third-party systems, and executing the virtual mating simulation comprises computing interface stress states for each anchor type in the construct and enforcing compatibility thresholds for all anchor types before generating the interoperability authorization signal.

Detail 30: The method of detail 16, further comprising logging, by the hardware-interlocked manufacturing controller, at least the interoperability authorization signal, the target fixation profile, and a summary of the interface stress state in an immutable audit trail associated with the manufactured patient-specific spinal fixation rod.

Detail 31: A system for designing a patient-specific spinal fixation rod, comprising: a processing unit comprising a deep-learning neural network trained on historical spinal datasets, the historical spinal datasets including anatomical parameters for prior patients, the anatomical parameters comprising at least: pelvic incidence (PI), pelvic tilt (PT), thoracic kyphosis magnitude and shape (TK), vertebral pelvic angle (VPA) for specified vertebrae, distances from a femoral head to an S1 endplate, segment distances between vertebrae, positions of vertebral centers from C2 to S1, regional and segmental Cobb angles, and orientations of vertebral endplates; and (a) receive, as input, patient-specific anatomical parameters comprising at least pelvic incidence (PI), pelvic tilt (PT), thoracic kyphosis (TK) magnitude and shape, vertebral pelvic angle (VPA), segment distances between vertebrae, positions of vertebral centers from C2 to S1, Cobb angles, and orientations of vertebral endplates; (b) generate, by the neural network, an estimated pelvic orientation and an estimated pelvic shape based on at least pelvic incidence (PI), pelvic tilt (PT), and distance from the femoral head to the S1 endplate; (c) generate, by the neural network, a spline representing a continuous spinal curve based on at least the vertebral pelvic angle (VPA), the estimated pelvic shape, the estimated pelvic orientation, and the segment distances between vertebrae; (d) generate, by the neural network, estimated positions of vertebrae along the spline based on positions of vertebral centers and estimated angulations between the spline and the vertebral endplates based on the spline, the vertebral pelvic angle (VPA), and the endplate orientations; and (e) generate an ideal full-spine shape by combining the estimated angulations and the estimated vertebral positions, and determine a patient-specific spinal fixation rod geometry based on the ideal full-spine shape.

Detail 32: The system of detail 31, wherein generating the spline comprises generating a spline-based reconstruction pipeline that includes: (a) estimating pelvis orientation in space; (b) generating the spline to represent a full-spine curve referenced to the pelvis orientation; (c) placing vertebral centroids along the spline using vertebral center positions from C2 to S1; and (d) assigning endplate angulation at each vertebral level based on the spline orientation and vertebral endplate orientations, so that the ideal full-spine shape is defined by both vertebral positions and endplate angulations.

Detail 33: The system of detail 31, wherein the processing unit is further configured to define thoracic kyphosis (TK) using a regression method and to define a relationship between pelvic incidence (PI) and vertebral pelvic angle (VPA) using a regression method, each regression method having a coefficient of determination ($R^2$) in the range from 0.8 to 1.0, optionally in the range from 0.9 to 1.0, optionally at least 0.9, and optionally at least 0.8.

Detail 34: The system of detail 31, wherein the processing unit is configured to train the neural network using historical data further comprising intervertebral heights, vertebral body heights, intervertebral angulation, vertebral body angulation, segmental alignment from T1 to the pelvis, and distances between implanted rods and vertebral bodies based on postoperative imaging, so that the neural network learns relationships between rod position, spinal alignment, and long-term biomechanical outcomes.

Detail 35: The system of detail 31, wherein the processing unit is further configured to model the ideal full-spine shape using a gravity line biomechanical model that predicts reciprocal changes above fused vertebral segments and pelvic position in space, the gravity line biomechanical model computing a total body center of mass (COM) from segment mass percentages and center-of-mass offsets and vertically projecting the center of mass (COM) to define a gravity line (GL).

Detail 36: The system of detail 35, wherein the ideal full-spine shape accounts for posterior translation of the spinal fixation rod relative to the patient's pelvis, thoracolumbar alignment, and cervical alignment such that the predicted postoperative configuration maintains proper head position and substantially horizontal gaze.

Detail 37: The system of detail 31, wherein the patient-specific spinal fixation rod geometry is configured so that one or more rods extend from vertebra T1 to the pelvis or from vertebra C2 to vertebra T1, and wherein the processing unit selects the rod extent based on predicted biomechanical requirements and the ideal full-spine shape.

Detail 38: The system of detail 31, further comprising a finite element analysis (FEA) module configured to: (a) create a digital twin model of a spinal construct including the patient-specific spinal fixation rod geometry and a representation of the patient's spine; (b) execute finite element analysis (FEA) under physiologic loading conditions to compute stress and strain distributions at vertebral levels and junctional zones; and (c) identify regions of elevated junctional stress or stress concentration at transitions between fused and unfused vertebrae, including regions associated with proximal junctional kyphosis (PJK) or proximal junctional failure.

Detail 39: The system of detail 38, wherein the physiologic loading conditions applied in the finite element analysis (FEA) comprise a follower load in the range from 200 to 1200 Newtons, optionally in the range from 400 to 800 Newtons, flexion and extension moments of approximately ±7.5 Newton-meters, and lateral bending and axial rotation moments of approximately ±5.0 Newton-meters.

Detail 40: The system of detail 38, wherein the finite element analysis (FEA) module is configured to predict at least one of: (a) the impact of rod stiffness, fixation techniques, and the ideal full-spine shape on adjacent segment loading; (b) the influence of different spinal rod materials on adjacent segment biomechanics; (c) the effects of hybrid spinal rods on spinal biomechanics to optimize load distribution and minimize abrupt angulation transitions; (d) the effects of interactions of patient soft tissue with the rods over time; and (e) spinal rod fatigue-related failure at junctional zones, including predicted fatigue life in the range from 10^6 to 10^8 cycles, optionally in the range from 10^7 to 1.5×10^7 cycles.

Detail 41: The system of detail 38, wherein the processing unit is configured to iteratively modify the patient-specific spinal fixation rod geometry based on outputs of the finite element analysis (FEA) module so as to reduce junctional stress concentration factors and maintain maximum von Mises stress below a predetermined fraction of rod material yield strength, the predetermined fraction being in the range from 0.4 to 0.8, optionally in the range from 0.5 to 0.6.

Detail 42: The system of detail 31, wherein the processing unit further comprises a multi-objective optimization engine configured to cooperate with the neural network and the finite element analysis (FEA) module to perform multi-objective optimization of the spinal fixation rod geometry, balancing at least two of: biomechanical performance, patient-specific comfort, desired flexibility, fatigue resistance, and minimization of stress concentrations.

Detail 43: The system of detail 31, wherein the processing unit is configured to segment the patient-specific spinal fixation rod geometry into regions corresponding to the patient's segment distances between vertebrae L4-S1, L1-L4, T10-L2, T5-T9, and T1-T6, and to generate rod design data specifying visual markings for the regions and for angulation inflection points on the spinal fixation rod to assist intraoperative alignment and placement.

Detail 44: A system for hardware-interlocked artificial intelligence (AI) manufacturing and interoperability of spinal fixation rods, comprising: a computing platform configured to execute a digital twin (DT) biomechanical validation of a candidate spinal fixation rod geometry, the digital twin (DT) representing at least a patient-specific spinal construct and a spinal fixation rod construct, and to determine, based on the digital twin (DT) biomechanical validation, whether the candidate spinal fixation rod geometry satisfies at least one predefined stability criterion; and a hardware-interlocked manufacturing controller (MC) communicatively coupled to the computing platform and to a physical fabrication device (PFD), the manufacturing controller (MC) being configured to: (a) maintain a hardware-enforced isolation state in which a fabrication actuation mechanism of the physical fabrication device (PFD) is physically prevented from executing manufacturing instructions corresponding to the candidate spinal fixation rod geometry; and (b) transition from the hardware-enforced isolation state to a fabrication-enabled state only upon receipt and cryptographic verification of an authorization signal generated by the computing platform in response to convergence of the digital twin (DT) biomechanical validation and satisfaction of the stability criterion, such that the candidate spinal fixation rod geometry cannot be manufactured in the absence of the cryptographically verifiable authorization signal.

Detail 45: The system of detail 44, wherein the hardware-enforced isolation state comprises opening an electrical relay in a fabrication actuation circuit and de-energizing one or more motors of the physical fabrication device (PFD), such that mechanical motion of the fabrication actuation mechanism is physically blocked until the manufacturing controller (MC) cryptographically validates the authorization signal.

Detail 46: The system of detail 44, wherein the authorization signal comprises a digital signature generated using a hardware security module (HSM), and wherein the manufacturing controller (MC) is configured to validate the authorization signal using a public key infrastructure (PKI) so that only an authorization signal issued by the computing platform after convergence of the digital twin (DT) biomechanical validation is accepted.

Detail 47: The system of detail 44, wherein the digital twin (DT) biomechanical validation comprises a finite element analysis (FEA) model including distinct material domains for cortical bone, cancellous bone, intervertebral discs, spinal fixation rods, and fixation anchors, and wherein the computing platform is configured to assign material properties based on patient-specific bone quality derived from preoperative computed tomography (CT) Hounsfield units.

Detail 48: The system of detail 47, wherein the stability criterion comprises at least: (a) a maximum von Mises stress in the spinal fixation rod being less than a fraction of a rod material yield strength in the range from 0.4 to 0.8, optionally in the range from 0.5 to 0.6; and (b) a predicted fatigue life for the spinal fixation rod under cyclic physiologic loading being in the range from 10^6 to 10^8 cycles, optionally in the range from 10^7 to 1.5×10^7 cycles.

Detail 49: The system of detail 44, wherein the computing platform further comprises a fixation component library representing a plurality of third-party fixation anchor systems as digital twin (DT) models including tulip geometries, screw trajectories, range-of-motion envelopes, and material properties, and wherein the digital twin (DT) biomechanical validation includes a virtual mating simulation that evaluates mechanical compatibility between the candidate spinal fixation rod geometry and at least one selected third-party fixation anchor system according to an interoperability criterion.

Detail 50: The system of detail 49, wherein the authorization signal is generated only when both the stability criterion for the patient-specific spinal construct and the interoperability criterion for the selected third-party fixation anchor system are satisfied, such that the hardware-enforced isolation state is maintained if either criterion is not satisfied.

Detail 51: The system of detail 44, wherein the computing platform is configured to execute the digital twin (DT) biomechanical validation on a remote server, and the manufacturing controller (MC) is implemented as a local hardware device adjacent to the physical fabrication device (PFD), the manufacturing controller (MC) being configured to enforce the hardware-enforced isolation state across a network boundary until the cryptographically verifiable authorization signal is received from the remote server.

Detail 52: The system of detail 44, further comprising a user interface configured to render a manufacturing actuation widget, and wherein the manufacturing controller (MC) is configured to ignore, intercept, or discard any user input signals directed to the manufacturing actuation widget while the hardware-enforced isolation state is active, irrespective of visibility or apparent activation of the manufacturing actuation widget.

Detail 53: The system of detail 44, wherein the computing platform is further configured to: (a) receive postoperative imaging and clinical outcome data for spinal fixation rods manufactured using the system; (b) update at least one parameter of the digital twin (DT) biomechanical validation or at least one threshold of the stability criterion based on the postoperative data; and (c) thereby adaptively refine the conditions under which the authorization signal is generated for subsequent candidate spinal fixation rod geometries.

Detail 54: The system of detail 44, wherein the manufacturing controller (MC) is further configured to maintain an immutable audit log recording at least: (a) timestamps of transitions between the hardware-enforced isolation state and the fabrication-enabled state; (b) identification of each candidate spinal fixation rod geometry for which an authorization signal was validated; and (c) summary indicators of the stability criterion and, when applicable, the interoperability criterion, thereby providing traceability for regulatory review and quality assurance.

Detail 55: The system of detail 44, wherein the system is further configured to be used for manufacturing an inventory of pre-contoured spinal fixation rods, and wherein each spinal fixation rod included in the inventory is associated with a stored record comprising the validated authorization signal and corresponding digital twin (DT) biomechanical validation results, the stored record being retrievable based on a unique identifier marked on the spinal fixation rod.

Detail 56: A manufacturing controller for a physical fabrication device (PFD) configured to fabricate a spinal fixation device, the manufacturing controller (MC) comprising: a hardware isolation module including at least one general-purpose input/output (GPIO) relay and an actuation power circuit, the hardware isolation module being configured to maintain the physical fabrication device (PFD) in a locked state in which one or more motors of the physical fabrication device (PFD) are de-energized and execution of manufacturing instructions is physically prevented; a cryptographic interlock module configured to control release of a decryption key required to decrypt the manufacturing instructions; and a conditional gating module communicatively coupled to a computing platform configured to execute a digital twin (DT) biomechanical simulation of a candidate device geometry, the conditional gating module being configured to: (a) transmit to the computing platform data describing the candidate device geometry and cause the computing platform to execute the digital twin (DT) biomechanical simulation to compute a stress state and one or more sensitivity gradients derived directly from the stress state; (b) receive from the computing platform a convergence authorization signal indicating that a stability criterion based on the stress state and the one or more sensitivity gradients has been satisfied; (c) maintain the hardware isolation module in the locked state and withhold the decryption key from the cryptographic interlock module while the stability criterion remains unsatisfied; and (d) in response to receiving and validating the convergence authorization signal, transition from the locked state to an unlocked state by closing the general-purpose input/output (GPIO) relay and energizing the actuation power circuit or by releasing the decryption key so as to permit execution of the manufacturing instructions, wherein fabrication of the spinal fixation device cannot proceed without the validated convergence authorization signal.

Detail 57: The manufacturing controller (MC) of detail 56, further comprising a user interface (UI) interlock subsystem configured to implement human-input inhibition, the user interface (UI) interlock subsystem comprising a manufacturing actuation widget (MAW) rendered on a user interface (UI) in a deactivated state in which user input events directed to the manufacturing actuation widget (MAW) are electronically suppressed, intercepted, or discarded while the manufacturing controller (MC) is in the locked state, regardless of visual appearance of the manufacturing actuation widget (MAW) or user interaction attempts, and wherein the manufacturing controller (MC) is further configured to optionally allow an emergency override procedure that requires completion of a friction-filled multi-step confirmation sequence and records any emergency override attempt in an immutable audit log. In some embodiments, the emergency override does not energize the motors or bypass the requirement for a valid convergence authorization token; it only affects how the UI behaves once a valid token exists.

Detail 58: The manufacturing controller (MC) of detail 56, wherein the hardware isolation module comprises at least two independent isolation mechanisms selected from: (a) a general-purpose input/output (GPIO) relay in a motor drive circuit; (b) a safety-rated contactor in a main power line; and (c) a solid-state switch in a control-signal path to a servo drive, such that failure of a single isolation mechanism does not permit energization of the physical fabrication device (PFD) in the absence of the convergence authorization signal.

Detail 59: The manufacturing controller (MC) of detail 56, wherein the cryptographic interlock module is configured to receive the convergence authorization signal as a digitally signed token generated by a hardware security module (HSM) of the computing platform and to validate the digital signature using a public key infrastructure (PKI), and wherein the decryption key is released only upon successful validation of the digital signature and verification that the token corresponds to the candidate device geometry.

Detail 60: The manufacturing controller (MC) of detail 56, wherein the conditional gating module is further configured to: (a) receive from the computing platform, in addition to the convergence authorization signal, a summary of the stress state and values of the stability criterion; and (b) compare the received summary with locally stored threshold values, and to refuse transition to the unlocked state if any portion of the summary is inconsistent with the locally stored threshold values, thereby providing an additional safeguard against erroneous convergence authorization signals.

Detail 61: The manufacturing controller (MC) of detail 56, wherein the conditional gating module is configured to cooperate with a surrogate machine learning model of the digital twin (DT) biomechanical simulation for initial screening of the candidate device geometry, the surrogate machine learning model being trained to approximate finite element analysis (FEA) outputs, and wherein the conditional gating module requires a full finite element analysis (FEA) based digital twin (DT) biomechanical simulation at predetermined intervals or upon detection of candidate device geometries that fall outside a predefined similarity range, such that computation time is reduced while maintaining safety.

Detail 62: The manufacturing controller (MC) of detail 56, wherein the conditional gating module is further configured to: (a) automatically return the manufacturing controller (MC) from the unlocked state to the locked state upon completion of execution of the manufacturing instructions or upon expiration of a timeout period in the range from 10 seconds to 10 minutes, optionally in the range from 30 seconds to 3 minutes; and (b) require a new convergence authorization signal for any subsequent execution of manufacturing instructions corresponding to a new or modified candidate device geometry.

Detail 63: The manufacturing controller (MC) of detail 56, wherein the manufacturing controller (MC) is implemented as a local hardware device adjacent to the physical fabrication device (PFD), and the computing platform executing the digital twin (DT) biomechanical simulation is located remotely across a network boundary, the manufacturing controller (MC) being configured to enforce the locked state whenever communication with the computing platform is interrupted, degraded beyond a predetermined quality-of-service threshold, or produces a stale convergence authorization signal older than a validity period in the range from 10 seconds to 24 hours, optionally in the range from 60 seconds to 2 hours.

Detail 64: The manufacturing controller (MC) of detail 57, wherein the immutable audit log records at least: (a) timestamps of transitions between the locked state and the unlocked state; (b) identifiers of candidate device geometries associated with each convergence authorization signal; (c) whether the transition was triggered by a standard convergence authorization signal or by an emergency override procedure; and (d) summary values of the stability criterion and any warnings or violations reported by the computing platform, the immutable audit log being stored in a tamper-evident format for regulatory and quality-assurance review.

Detail 65: A system for generating and validating candidate spinal fixation rod geometries, comprising: a generative artificial intelligence (AI) module comprising a machine-learning model trained on a database of historical spinal alignments and postoperative clinical outcomes, the generative artificial intelligence (AI) module being configured to receive patient-specific anatomical parameters and to generate a candidate spinal fixation rod geometry; a physics-based validation module configured to receive the candidate spinal fixation rod geometry from the generative artificial intelligence (AI) module and to execute a biomechanical simulation of a spinal construct including the candidate spinal fixation rod geometry so as to compute stress tensors and to generate a stress state verification indicating whether at least one stress-based safety threshold is satisfied; and a hardware-interlocked manufacturing controller communicatively coupled to the generative artificial intelligence (AI) module, the physics-based validation module, and a physical fabrication device, the hardware-interlocked manufacturing controller being configured to control transmission of manufacturing instructions for fabrication of the candidate spinal fixation rod geometry based on the stress state verification.

Detail 66: The system of detail 65, wherein the system implements a neuro-physical loop, the neuro-physical loop comprising that, when the stress state verification indicates that the candidate spinal fixation rod geometry fails to satisfy the at least one stress-based safety threshold, the hardware-interlocked manufacturing controller: (a) automatically intercepts any fabrication initiation command corresponding to the candidate spinal fixation rod geometry; (b) generates and transmits a regeneration signal to the generative artificial intelligence (AI) module, the regeneration signal embedding stress-tensor-derived constraints identifying at least one region of stress exceedance; and (c) causes the generative artificial intelligence (AI) module to generate a regenerated spinal fixation rod geometry under the embedded stress-tensor-derived constraints, and wherein the hardware-interlocked manufacturing controller restricts transmission of manufacturing instructions to the physical fabrication device until the physics-based validation module generates a stress state verification indicating that a regenerated spinal fixation rod geometry satisfies the at least one stress-based safety threshold.

Detail 67: The system of detail 65, wherein the generative artificial intelligence (AI) module implements at least one of: (a) a generative adversarial network (GAN) architecture in which the physics-based validation module provides discriminator feedback based on the stress state verification; (b) a transformer-based architecture employing an attention mechanism to prioritize historical spinal alignments that match the patient-specific anatomical parameters; and (c) a reinforcement learning (RL) architecture in which candidate spinal fixation rod geometries are iteratively refined based on reward signals derived from the stress state verification and historical postoperative clinical outcomes.

Detail 68: The system of detail 65, wherein the physics-based validation module comprises a digital twin (DT) finite element analysis (FEA) model of the spinal construct, the digital twin (DT) finite element analysis (FEA) model including distinct material property domains for cortical bone, cancellous bone, intervertebral soft tissues, spinal fixation rods, and fixation anchors, and wherein the physics-based validation module computes the stress tensors at least at rod-bone interfaces and junctional transition zones.

Detail 69: The system of detail 65, wherein the generative artificial intelligence (AI) module is trained using a physics-informed loss function that penalizes candidate spinal fixation rod geometries predicted by the physics-based validation module to produce stress tensors exceeding the at least one stress-based safety threshold, thereby biasing the generative artificial intelligence (AI) module toward generating biomechanically feasible geometries.

Detail 70: The system of detail 65, wherein the generative artificial intelligence (AI) module employs federated learning to update parameters of the machine-learning model across multiple institutions using de-identified postoperative imaging and outcome data, without requiring transfer of raw patient-level data between the institutions.

Detail 71: The system of detail 65, further comprising a continuous learning pipeline configured to: (a) receive postoperative imaging data and associated clinical outcome measures for implanted spinal fixation rods previously manufactured using the system; (b) extract, from the postoperative imaging data, alignment parameters and rod-bone positional relationships; and (c) use the extracted parameters and clinical outcome measures to update the training data for at least one of the generative artificial intelligence (AI) module and the physics-based validation module, thereby improving future generation and validation of candidate spinal fixation rod geometries.

Detail 72: The system of detail 65, wherein the generative artificial intelligence (AI) module represents each candidate spinal fixation rod geometry as a three-dimensional point cloud or centerline curve and converts the representation directly into manufacturing instructions comprising at least one of: numerically controlled bending commands or G-code instructions for the physical fabrication device.

Detail 73: The system of detail 66, wherein the regeneration signal comprises numerical bounds on at least one component of the stress tensors, spatial masks identifying elements or regions of the spinal construct with stress exceedance, and one or more target reductions in stress magnitude, and wherein the generative artificial intelligence (AI) module conditions subsequent geometry generation on the numerical bounds, spatial masks, and target reductions.

Detail 74: The system of detail 65, wherein the hardware-interlocked manufacturing controller maintains a locked state in which a fabrication actuation mechanism of the physical fabrication device is de-energized while any candidate spinal fixation rod geometry is classified by the physics-based validation module as failing the at least one stress-based safety threshold, and transitions from the locked state to an unlocked state enabling fabrication only when a stress state verification indicates that a corresponding candidate or regenerated spinal fixation rod geometry satisfies the at least one stress-based safety threshold and a corresponding authorization signal is cryptographically validated.

Detail 75: A system for universal interoperability and management of a pre-validated spinal fixation rod inventory, comprising: a fixation component library stored on a computing platform, the fixation component library comprising digital twin (DT) definitions of a plurality of third-party fixation components, each digital twin (DT) definition including at least one of: (a) a pedicle screw geometry; (b) a hook geometry; (c) a rod-connector geometry; (d) a tulip head geometry; (e) a range of motion (ROM) envelope for a polyaxial joint; (f) thread geometry and locking interface geometry; (g) material composition and material yield strength; (h) surface finish and coating properties; and (i) maximum allowable angulation and insertion depth parameters; an inventory database configured to store a plurality of pre-validated spinal fixation rod geometries together with associated compatibility metadata; a virtual mating engine configured to receive a candidate spinal fixation rod geometry and at least one selected digital twin (DT) definition from the fixation component library, to simulate geometric and tribological interaction between the candidate spinal fixation rod geometry and the selected third-party fixation component, and to output an interoperability evaluation; and a hardware-interlocked manufacturing controller communicatively coupled to the virtual mating engine and to a physical fabrication device, the hardware-interlocked manufacturing controller being configured to allow fabrication and stocking of a spinal fixation rod in the inventory database only when both a biomechanical stability criterion and an interoperability criterion derived from the interoperability evaluation are satisfied.

Detail 76: The system of detail 75, wherein the virtual mating engine implements a virtual mating protocol that simulates at least: (a) geometric fit between the candidate spinal fixation rod geometry and a tulip head channel, including checks for tulip bottom-out, set-screw travel margin, and rod seating depth; (b) joint kinematics within the range of motion (ROM) envelope of a polyaxial screw or hook, including maximum allowable angulation in flexion, extension, lateral bending, and axial rotation; and (c) tribological behavior at the rod-anchor interface, including contact pressure distribution, frictional slip tendency, and wear-related risk.

Detail 77: The system of detail 75, wherein the virtual mating engine is further configured to evaluate at least one of: (a) a galvanic corrosion index based on material pairings between the candidate spinal fixation rod geometry and the selected third-party fixation component, using material composition data stored in the fixation component library; (b) a pull-through or pull-out risk based on rod diameter, tulip head opening geometry, and locking set-screw preload; and (c) a minimum clearance between the candidate spinal fixation rod geometry and surrounding anatomical structures or implants modeled in a digital twin (DT) representation of the spinal construct.

Detail 78: The system of detail 75, wherein the hardware-interlocked manufacturing controller maintains a locked state in which a fabrication actuation mechanism of the physical fabrication device is physically prevented from executing manufacturing instructions corresponding to the candidate spinal fixation rod geometry while the interoperability evaluation indicates that the interoperability criterion is not satisfied, even if the biomechanical stability criterion for the spinal construct is satisfied, thereby preventing fabrication of spinal fixation rods that are biomechanically acceptable for the spine but incompatible with the selected third-party fixation components.

Detail 79: The system of detail 75, wherein the inventory database is populated by clustering historical patient anatomical parameters to generate a plurality of candidate spinal fixation rod geometries, running for each candidate spinal fixation rod geometry a stress-gradient and stability-criterion validation pipeline and a virtual mating pipeline gated by the hardware-interlocked manufacturing controller, and stocking only spinal fixation rods that passed both pipelines, the stocked spinal fixation rods providing coverage of a target patient population in a range from 80 to 100 percent, optionally in a range from 90 to 98 percent, with an average alignment error in a range from 0.5 to 5.0 degrees, optionally in a range from 0.5 to 2.0 degrees.

Detail 80: The system of detail 75, wherein the fixation component library includes digital twin (DT) definitions for fixation components from at least two different third-party vendors and allows construction of mixed-vendor constructs comprising pedicle screws, hooks, and connectors from different vendors, and wherein the virtual mating engine is configured to ensure interoperability of the candidate spinal fixation rod geometry across all fixation components in a mixed-vendor construct before the spinal fixation rod is admitted to the inventory database.

Detail 81: The system of detail 75, wherein each pre-validated spinal fixation rod stored in the inventory database is associated with compatibility metadata indicating, for each third-party fixation component family represented in the fixation component library, at least one of: (a) a binary compatibility flag; (b) a maximum recommended angulation; (c) a recommended torque range for a locking set-screw; and (d) a note of any prohibited construct configurations, and wherein the compatibility metadata is encoded in a machine-readable identifier physically marked on the spinal fixation rod.

Detail 82: The system of detail 75, wherein the inventory database is further configured to support a search and selection workflow in which a user specifies at least one of: (a) pelvic incidence; (b) global sagittal alignment; (c) planned fusion levels; (d) target third-party fixation component family; and (e) patient height or body mass index, and the system returns a set of pre-validated spinal fixation rods ranked by predicted alignment accuracy, biomechanical performance, and interoperability with the specified third-party fixation component family.

Detail 83: The system of detail 75, wherein the fixation component library supports versioning of digital twin (DT) definitions for third-party fixation components, and the system is configured to automatically re-run virtual mating evaluations and update compatibility metadata for affected spinal fixation rods when a digital twin (DT) definition is revised or when a new version of a third-party fixation component is introduced.

Detail 84: The system of detail 75, wherein the system further comprises an analytics engine configured to track utilization of spinal fixation rods from the inventory and to generate metrics including at least: (a) frequency of selection of specific spinal fixation rod geometries; (b) construct-level compatibility statistics with different third-party fixation component families; and (c) postoperative revision or complication rates associated with specific combinations of spinal fixation rod geometries and fixation component families, and wherein the analytics engine is configured to provide recommendations for inventory optimization.

Detail 85: A method of generating and maintaining a universal pre-validated spinal fixation rod inventory interoperable with third-party fixation components, comprising: (a) receiving historical patient anatomical parameters and clustering the historical patient anatomical parameters into groups; (b) generating, for each group, at least one candidate spinal fixation rod geometry; (c) executing, for each candidate spinal fixation rod geometry, a digital twin (DT) biomechanical validation to evaluate a biomechanical stability criterion; (d) executing, for each candidate spinal fixation rod geometry and for at least one selected digital twin (DT) fixation component from a fixation component library, a virtual mating simulation to evaluate an interoperability criterion; (e) for each candidate spinal fixation rod geometry that satisfies both the biomechanical stability criterion and the interoperability criterion, causing a hardware-interlocked manufacturing controller to fabricate a corresponding spinal fixation rod and to admit the spinal fixation rod to an inventory database; and (f) associating, in the inventory database, compatibility metadata and anatomical coverage metadata with each admitted spinal fixation rod.

Detail 86: The method of detail 85, wherein executing the digital twin (DT) biomechanical validation comprises running a finite element analysis (FEA) under physiologic loading conditions including a compressive follower load in a range from 200 to 1200 Newtons, optionally in a range from 400 to 800 Newtons, and flexion and extension moments in a range from ±5.0 to ±10.0 Newton-meters, optionally approximately ±7.5 Newton-meters, and lateral bending and axial rotation moments in a range from ±3.0 to ±7.0 Newton-meters, optionally approximately ±5.0 Newton-meters.

Detail 87: The method of detail 85, wherein the anatomical coverage metadata includes, for each admitted spinal fixation rod, a region of anatomical parameter space specifying at least pelvic incidence, thoracic kyphosis, and global sagittal alignment for which the spinal fixation rod is predicted to achieve an alignment error in a range from 0.5 to 5.0 degrees, optionally in a range from 0.5 to 2.0 degrees, and wherein the inventory is maintained so that aggregate coverage across all admitted spinal fixation rods spans at least 80 percent, optionally at least 95 percent, of a target patient population.

Detail 88: The method of detail 85, further comprising recording, for each admitted spinal fixation rod, a traceability record that links: (a) the candidate spinal fixation rod geometry; (b) the digital twin (DT) biomechanical validation results; (c) the virtual mating simulation results; and (d) identifiers of third-party fixation component families deemed compatible, and encoding a reference to the traceability record in a unique identifier physically marked on the spinal fixation rod.

Detail 89: The method of detail 85, further comprising tailoring sub-inventories for different clinical sites by selecting subsets of the admitted spinal fixation rods based at least on regional distributions of pelvic incidence and global sagittal alignment parameters and on prevalent third-party fixation component families used at each clinical site.

Detail 90: The method of detail 85, further comprising, for a newly introduced third-party fixation component, adding a digital twin (DT) definition of the new third-party fixation component to the fixation component library, running virtual mating simulations between the digital twin (DT) definition and existing spinal fixation rods in the inventory database, and updating compatibility metadata to indicate which existing spinal fixation rods are interoperable with the new third-party fixation component.

Detail 91: The method of detail 85, further comprising generating, for a specific surgical case, a recommended subset of spinal fixation rods by inputting patient-specific anatomical parameters and a selected third-party fixation component family, querying the inventory database using the anatomical coverage metadata and compatibility metadata, and outputting a ranked list of compatible spinal fixation rods with predicted alignment error and biomechanical performance indicators.

Detail 92: A kit comprising: a plurality of pre-validated spinal fixation rods obtained from the inventory database managed by the system of detail 75, each of the pre-validated spinal fixation rods having passed both a digital twin (DT) biomechanical validation and a virtual mating interoperability validation; and packaging or labeling that identifies, for each of the pre-validated spinal fixation rods, at least one compatible third-party fixation component family and at least one recommended anatomical parameter range.

Detail 93: The kit of detail 92, wherein each pre-validated spinal fixation rod is marked with a machine-readable identifier that encodes a link to its traceability record in the inventory database, the traceability record comprising at least digital twin (DT) biomechanical validation results, virtual mating simulation results, and compatible fixation component families.

Detail 94: The kit of detail 92, wherein the packaging or labeling includes a compatibility map that visually or textually correlates the pre-validated spinal fixation rods with specific third-party fixation component families, fusion levels, and target pelvic incidence ranges, thereby assisting selection of a spinal fixation rod intraoperatively.

Detail 95: The kit of detail 92, further comprising a printed or electronic selection guide that instructs a user how to select a pre-validated spinal fixation rod based on intraoperative measurements of alignment and the planned use of third-party fixation components, the selection guide referencing the anatomical coverage metadata and compatibility metadata associated with the pre-validated spinal fixation rods.

Detail 96: The kit of detail 92, wherein the packaging or labeling further comprises a quick response (QR) code or other scannable code associated with each pre-validated spinal fixation rod, the quick response (QR) code being configured to provide access to a digital dashboard displaying at least: simulated alignment outcomes, stress distributions, and compatible third-party fixation component configurations.

Detail 97: The kit of detail 92, wherein the plurality of pre-validated spinal fixation rods included in the kit is selected to cover a range of pelvic incidence values in a range from 30 to 80 degrees, optionally in a range from 40 to 70 degrees, and a range of global sagittal alignment targets, such that for a predefined surgical indication the kit provides at least one pre-validated spinal fixation rod predicted to achieve an alignment error in a range from 0.5 to 5.0 degrees, optionally in a range from 0.5 to 2.0 degrees.

Detail 98: The kit of detail 92, further comprising at least one trial rod or alignment template whose geometry corresponds to at least one of the pre-validated spinal fixation rods, the trial rod or alignment template being configured for intraoperative use to verify fit and alignment prior to implanting a corresponding spinal fixation rod.

Detail 99: The kit of detail 92, wherein the digital dashboard accessed via the quick response (QR) code is configured to be updated with postoperative imaging and outcome data for constructs using pre-validated spinal fixation rods from the kit, and to display aggregated performance metrics for the specific spinal fixation rod geometries and compatible third-party fixation component families over time.

In an overview discussion of the computing system, FIG. 1 depicts an example of a suitable computing system environment 100 on which aspects of the invention may be implemented. For example, the computing system environment 100 may be used to monitor and/or control one or more modules of a navigation system. Such a computing environment may represent a home computer, a tablet, a mobile device, a server and/or any another computing device.

The computing system environment 100 is only one example of a suitable computing environment and is not intended to suggest any limitation as to the scope of use or functionality of the invention. Neither should the computing environment 100 be interpreted as having any dependency or requirement relating to any one component or combination of components illustrated in the illustrative operating environment 100.

Aspects of the invention are operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 1, an illustrative system for implementing aspects of the invention includes a general-purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable, and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random-access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 141 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the illustrative operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies.

A user may enter commands and information into the computer 110 through input devices such as a keyboard 162 and pointing device 161, commonly referred to as a mouse, trackball, or touch pad. Other input devices (not shown) may include a microphone, joystick, game pad, satellite dish, scanner, or the like. These and other input devices are often connected to the processing unit 120 through a user input interface 160 that is coupled to the system bus but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include peripheral output devices 196 such as speakers and printer, which may be connected through an output peripheral interface 195.

The computer 110 may operate in a networked environment using logical connections to one or more remote computers, such as a remote computer 180. The remote computer 180 may be a personal computer, a server, a router, a network PC, a peer device, or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173 but may also include other networks. Such networking environments are commonplace in offices, enterprise-wide computer networks, intranets, and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the network interface 170, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are illustrative and other means of establishing a communications link between the computers may be used.

The various methods or processes outlined herein may be implemented in any suitable hardware. Additionally, the various methods or processes outlined herein may be implemented in a combination of hardware and of software executable on one or more processors that employ any one of a variety of operating systems or platforms. For example, the various methods or processes may utilize software to instruct a processor to determine a spatial position (e.g., based on image matching, odometry, etc.), to extract features from one or more images, to communicate with a data repository, to perform speech recognition, to perform speech synthesis, to compress and/or decompress image and/or video data, or combinations thereof. Examples of such approaches are described above. However, any suitable combination of hardware and software may be employed to realize any of the embodiments discussed herein.

In this respect, various inventive concepts may be embodied as at least one non-transitory computer readable storage medium (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, implement the various embodiments of the present invention. The non-transitory computer-readable medium or media may be transportable, such that the program or programs stored thereon may be loaded onto any computer resource to implement various aspects of the present invention as discussed above.

The terms “program” or “software” are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor but may be distributed in a modular fashion among different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

As set describe herein, the methods and systems disclosed may employ machine learning. Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify “good” features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Deep Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

Various types of neural networks can be employed to process anatomical data and generate accurate predictions for spinal alignment. Each type of neural network offers unique advantages and is suited to different aspects of the data processing and prediction tasks involved in this method. Exemplary neural networks that may be used include:

1. Feedforward Neural Networks (FNNs): These are the simplest type of artificial neural networks where connections between the nodes do not form a cycle. They are typically used for straightforward tasks such as pattern recognition and basic prediction. In the context of spinal correction, FNNs can be used to process input data and generate initial predictions for spinal alignment.

2. Convolutional Neural Networks (CNNs): CNNs are particularly effective for processing grid-like data, such as images. They are widely used in medical imaging to detect patterns and features. In this method, CNNs can be utilized to analyze spinal imaging data, identify anatomical landmarks, and extract relevant features for further processing.

3. Recurrent Neural Networks (RNNs): RNNs are designed to recognize patterns in sequences of data, making them suitable for time-series analysis. They can be used to track changes in spinal alignment over time and predict future alignment based on historical data. This is particularly useful for monitoring the progression of scoliosis and the effectiveness of corrective measures.

4. Long Short-Term Memory Networks (LSTMs): A type of RNN, LSTMs are capable of learning long-term dependencies and are effective in handling sequential data with time lags. They can be applied to model the dynamic aspects of spinal movement and predict how changes in one part of the spine may affect other areas over time.

5. Autoencoders: These are unsupervised neural networks used for learning efficient coding of input data. Autoencoders can be employed to reduce the dimensionality of complex anatomical data, retaining only the most relevant features for spinal alignment prediction.

6. Generative Adversarial Networks (GANs): GANs consist of two networks, a generator and a discriminator, which work against each other to improve data generation. In spinal correction, GANs can be used to simulate various spinal alignment scenarios and generate synthetic data to augment training datasets.

7. Deep Belief Networks (DBNs): These are composed of multiple layers of stochastic, latent variables. DBNs can be used to model complex relationships between anatomical parameters and predict spinal alignment with high accuracy.

8. Radial Basis Function Networks (RBFNs): These networks use radial basis functions as activation functions and are typically used for function approximation. RBFNs can be applied to interpolate the relationship between different anatomical parameters and predict the ideal spine shape.

Each of these neural network types can be tailored to specific tasks within the method, enhancing the overall accuracy and effectiveness of spinal deformities correction. By leveraging the strengths of different neural network architectures, the method can provide a comprehensive and adaptable approach to spinal alignment prediction and correction.

While particular embodiments have been described, it will be understood, however, that any invention appertaining to the methods and system described is not limited thereto, since modifications may be made by those skilled in the art, particularly in light of the foregoing teachings. It is, therefore, contemplated by the appended claims to cover any such modifications that incorporate those features or those improvements that embody the spirit and scope of the invention.

The methods and systems described herein may be implemented on any suitable computing architecture. In some embodiments, a computing environment includes one or more processors, memory, persistent storage, and network interfaces coupled via one or more buses. Processors may include general-purpose CPUs, multicore processors, graphics processors (GPUs), tensor or neural processing units (TPUs/NPUs), digital signal processors (DSPs), and/or custom accelerators such as FPGAs or ASICs. Any subset of these devices may be employed for training, fine-tuning, and/or inference of machine-learning models, including deep neural networks and other statistical or rules-based components. Program logic can be organized as applications, services, libraries, drivers, kernels, and/or microservices executing in user space or kernel space.

Memory may comprise volatile memory (e.g., registers, caches, SRAM, DRAM) and non-volatile memory (e.g., flash/SSD, NVMe drives, persistent memory, MRAM) storing instructions and data. A non-transitory computer-readable medium may store instructions that, when executed by one or more processors, cause the processors to perform any of the operations described herein. Storage may include block, file, and object stores, and may be deployed locally (on-premises), in public or private clouds, or across hybrid and multi-cloud configurations.

In some embodiments, applications are packaged into container images and orchestrated by a container orchestration platform to automate deployment, scaling, health management, and rollbacks. Orchestration may support declarative configuration, secrets management, workload autoscaling (e.g., horizontal/vertical), service discovery, and persistent volume attachment for stateful workloads. In other embodiments, portions of the system are delivered as "serverless" functions that execute in response to events (e.g., message arrivals, API calls, file uploads) with the cloud provider provisioning and managing underlying compute resources. Serverless components can be used for lightweight preprocessing, postprocessing, or background tasks, while long-running services and GPUs/TPUs run in containers or virtual machines as needed.

Networking may include local and wide-area networks, VPNs, and the public Internet using wired and/or wireless links. Edge devices (e.g., mobile phones, tablets, wearables, cameras, ultrasound probes, and other embedded devices) may execute on-device components with intermittent connectivity to upstream services. Communication may use secure channels (e.g., TLS) and authenticated requests (e.g., short-lived tokens). Message-oriented middleware (e.g., publish/subscribe topics and queues) can decouple producers and consumers, support back-pressure, and enable streaming or batch processing.

Data pipelines may ingest heterogeneous inputs (e.g., images, video frames, waveforms, text, tabular records, sensor measurements) into landing areas and durable stores. Schemas may be enforced or inferred; metadata catalogs can track provenance, lineage, and data quality. Feature stores can materialize precomputed or on-demand features. For unstructured content, embedding generators may map items to dense vectors stored in a vector index to support similarity search and retrieval-augmented workflows. Conventional relational, key-value, document, time-series, and object stores may also be used for transactional and analytical workloads.

Machine-learning components can include supervised, unsupervised, and reinforcement-learning models, classical and deep architectures (e.g., CNNs, RNNs, transformers, diffusion models), and hybrid or ensemble methods. Training may occur on clusters of accelerators with distributed data or model parallelism; inference can be performed online (request/response), offline (batch), or near-real-time (streaming). In some embodiments, a retrieval-augmented generation (RAG) pipeline couples a retriever with one or more generative models to ground outputs in a corpus of verified knowledge. The retriever can query a vector database and/or keyword index, optionally performing hybrid retrieval, reranking, and citation tracking. Embedding models may be domain-specific, multilingual, or multimodal, and can be periodically refreshed to reflect new data.

To improve latency and efficiency, models may be optimized via quantization (e.g., INT8 or FP8), pruning, knowledge distillation, operator/kernel fusion, graph compilation, caching (e.g., KV-cache), and mixed-precision execution. Workloads can be placed dynamically on heterogeneous accelerators; autoscaling may consider request rates, queue depth, GPU memory, and cost constraints. Observability may include tracing, metrics, and logs for request latency, throughput, error rates, and model-level telemetry (e.g., drift, calibration, and outlier detection). Canary and shadow deployments may be used to validate updates safely before promotion.

In some embodiments, privacy-preserving and security controls are incorporated by design. When training requires sensitive data, techniques such as federated learning can train models across distributed clients or sites while retaining raw data locally. Additional protections may include differential-privacy mechanisms to bound disclosure risk, secure enclaves or confidential-computing virtual machines to protect data and models "in use," encryption of data at rest and in transit, strong identity and access management, and cryptographic attestation of trusted execution environments. Policy-driven governance may include dataset and model cards, risk registers, audit logs, and controls aligned with contemporary AI risk-management frameworks. Runtime guardrails may filter inputs/outputs, enforce rate limits, and block unsafe prompts or responses based on configurable policies.

Deployment patterns may include: (i) single-tenant and multi-tenant SaaS; (ii) on-premises or virtual private cloud for regulated customers; (iii) edge-to-cloud split inference where a lightweight model runs on-device and delegates complex tasks to a remote service; and/or (iv) offline-capable modes that buffer requests and synchronize results when connectivity is restored. High availability can be achieved via multi-zone or multi-region redundancy, graceful degradation, queue-backed retries, idempotent APIs, and circuit-breaker patterns. Disaster recovery can include regular, encrypted backups and tested restore runbooks.

The system may expose one or more APIs (e.g., REST, gRPC, GraphQL) and SDKs. Access tokens may be scoped and short-lived, with continuous key rotation. Administrative consoles can surface configuration, quotas, and audit trails. Tooling may include CI/CD pipelines for infrastructure-as-code, automated testing (unit, integration, load, and safety evaluations), and rollout orchestration. MLOps workflows can address the model lifecycle: data collection, labeling, evaluation (including fairness and robustness metrics), versioning, packaging, deployment, monitoring, and rollback. Human-in-the-loop review may be invoked for low-confidence or high-risk cases.

Any module described herein can run on a single device or be distributed across multiple machines and clouds. The components may be combined, split, reordered, or omitted in various embodiments. The techniques are not limited to a particular programming language, framework, cloud provider, or model family. Unless stated otherwise, the examples are non-limiting, and any enumerated alternatives are illustrative rather than exhaustive.

Examples of Suitable Implementations (Non-Exhaustive)

Orchestrated containers for core services, with autoscaling and declarative rollouts.

Event-driven "serverless" functions for preprocessing, file ingestion, and scheduled jobs.

A retrieval layer using dense embeddings stored in a vector index for semantic search, optionally combined with keyword search and reranking for hybrid retrieval.

Accelerator-optimized inference using mixed precision and quantization to reduce latency and cost while meeting accuracy targets.

Privacy-enhancing features such as federated training, differential-privacy noise mechanisms for analytics, confidential-computing VMs for sensitive workloads, and encrypted transport and storage.

Centralized observability with metrics, traces, and logs, plus model-quality monitors (drift, bias checks, and safety filters).

The foregoing description is intended as a generalized, technology-agnostic base section that can be adapted to a variety of inventions. It may be combined with domain-specific embodiments (e.g., medical imaging, ultrasound processing, or other sensor-based systems) and with specific figures, claims, and examples as appropriate.

The Cryptographic "Gating" Mechanism: In some embodiments, the Hardware Interlock is not merely a signal gate but a cryptographic dependency. The computing platform generates manufacturing instructions (e.g., G-code) in an encrypted format. The decryption key required to execute these instructions is dynamically generated solely upon the satisfaction of the stability criterion. Specifically, the decryption key is derived from a cryptographic hash of the final, validated stress tensor field. Consequently, the manufacturing controller and physical fabrication device are computationally incapable of interpreting the manufacturing instructions until the physics-based validation is complete. This prevents 'bypassing' the safety check via manual overrides or software patches, as the machine instructions effectively do not exist in a readable format until safety is proven.

Surface Modification for Universal Compatibility: To ensure universal interoperability with third-party fixation anchors (e.g., pedicle screws from varying manufacturers), the physical fabrication device is configured to selectively modify the surface topology of the spinal rod. Based on the tribological data (friction coefficients, locking mechanism bite) stored in the digital twin of the target third-party screw, the system executes a micro-texturing pass. This process alters the surface roughness ($Ra$) of the rod at specific screw-engagement zones to match the locking requirements of the third-party anchor, ensuring sufficient pull-out strength and preventing slippage. In some embodiments, this results in a measurable $Ra$ difference of at least 0.1 $\mu m$ between engagement and non-engagement zones.

The Volumetric Exclusion Mask for AI: To prevent AI hallucinations, the system employs a volumetric exclusion mask. When the physics-based validation module detects a stress violation at a specific coordinate (e.g., the L3-L4 junction), it generates a 3D spatial mask representing the violated volume. This mask is fed back into the generative neural network as a negative bias constraint, mathematically forcing the network's latent space to generate subsequent geometries that spatially avoid the high-stress topology. This transforms the validation process from a passive check into an active, physics-constrained generation loop.

The system explicitly excludes any workflow wherein the validation of the rod geometry relies solely on a human user's visual confirmation, manual authorization signal, or surgeon override command, as such methods fail to ensure biomechanical convergence and lack the cryptographic proof of physics-based safety required by the hardware interlock.

EXAMPLES

The invention now being generally described it will be more readily understood by reference to the following examples which are included merely for purposes of illustration of certain aspects and embodiments of the present invention and are not intended to limit the invention.

Example 1. Hardware-Interlocked Manufacturing Controller

Referring to FIG. 1, the system comprises a manufacturing controller (100) communicatively coupled to a computing platform (200) and a physical fabrication device (300). The manufacturing controller (100) implements a conditional gating protocol with automatic optimization triggering.

The manufacturing controller (100) executes a conditional gating protocol that inhibits execution of the candidate rod geometry while the stability criterion remains unsatisfied. Upon receiving a candidate rod geometry that does not satisfy the stability criterion, the manufacturing controller (100) automatically triggers an optimization iteration by the computing platform (200) to modify the candidate rod geometry based on the computed sensitivity gradients. This automatic triggering creates a self-correcting loop that continues until a satisfactory geometry is achieved.

The manufacturing controller (100) permits execution only of a modified rod geometry that satisfies the stability criterion. The conditional gating protocol includes cryptographic verification to prevent unauthorized signal generation or replay attacks. Importantly, even if a system includes a manual override capability for other functions, the conditional gating protocol and automatic optimization trigger ensure that any geometry reaching the fabrication device has been validated.

The manufacturing controller 100 comprises a programmable logic controller (PLC), embedded microprocessor, or equivalent circuitry that is physically coupled to a Category 4/Performance Level e (Cat 4/PL e) safety relay compliant with ISO 13849-1 and/or IEC 62061 SIL 3 functional safety standards. In the locked state, the safety relay maintains an open circuit in the power supply line to the actuation motors (or servo drives) of the physical fabrication device 300, thereby electrically isolating the motors and rendering any bending or forming actuation thermodynamically impossible until the relay coil is energized. The relay coil is energized only upon successful receipt and cryptographic validation of the convergence authorization signal (convergence token) generated by the computing platform 200, ensuring that no software command, manual override switch, or user-interface interaction can close the circuit without objective, physics-based validation of the rod geometry.

In another embodiment, the system addresses the "human-in-the-loop" safety risk through a User Interface (UI) Interlock. The computing platform renders a Manufacturing Actuation Widget on the clinician's display. By default, and during any period where the stability criterion is unsatisfied (e.g., during active optimization or following a manual modification of the rod curve), the manufacturing controller forces this widget into the Deactivated State. Visually, this may be represented by "greying out" the button or displaying a "Simulation Required" overlay.

Hardware-Level Logic Flow. To avoid ambiguity, the specific algorithmic structure executed by the manufacturing controller (100) to enforce the locked state is defined as follows:

Input Acquisition: The controller receives the Candidate_Geometry vector ($V$) and Material_Properties matrix ($M$).

Simulation Execution: The controller computes the stress tensor field ($T$) where $T=f(V, M)$ under physiologic loads.

Threshold Comparison: The controller compares the maximum von Mises stress ($S_{max}$) within $T$ against the Yield Strength ($Y$) of the material.

Signal Generation:

IF ($S_{max}>Y*Safety\_Factor$): The controller writes a LOW (0V) signal to the General Purpose Input/Output (GPIO) pin connected to the fabrication motor relay, physically breaking the circuit (The Locked State).

IF ($S_{max}\le Y*Safety\_Factor$): The controller enables a check for the Convergence_Auth_Token. Only if the token is valid does it write a HIGH (5V/3.3V) signal to the relay, closing the circuit (The Unlocked State).

Override Rejection: During the LOW signal state, the controller executes a While loop that flushes/discards any input buffer packets received from the Manufacturing Actuation Widget, ensuring manual commands are computationally ignored.

Critically, this interlock prevents the "alert fatigue" phenomenon common in prior art systems, where users habitually dismiss warning pop-ups to proceed with unsafe designs. By physically decoupling the user's input from the fabrication trigger until the physics-based validation module generates the convergence authorization signal, the system enforces a hard safety stop that cannot be bypassed by standard user acknowledgement. If a user attempts to actuate the Deactivated widget, the system may display a "Stress Violation Visualization," highlighting the specific anatomical regions (e.g., L3-L4 junction) where projected stress exceeds the safety threshold, thereby educating the user on why the fabrication is blocked.

After the manufacturing controller (100) permits transmission of manufacturing instructions to the physical fabrication device (300), it may return to the gated state after transmission is complete, upon timeout, or upon detection of error conditions. Methods are tested for all descriptions above and further as discussed below.

Example 2. Computing Platform and Biomechanical Simulation and Generative Artificial Intelligence Module The computing platform (200) is configured to execute biomechanical simulation of candidate rod geometries. The simulation calculates a stress state under physiologic loading conditions. The stress state includes stress tensor values at locations throughout the simulated spinal construct.

The computing platform (200) computes sensitivity gradients derived directly from the stress state. The sensitivity gradients represent the mathematical relationship between design parameters and biomechanical performance metrics. The stress state from each simulation iteration mathematically constrains subsequent optimization iterations through the sensitivity gradient values.

While adjoint methods, automatic differentiation, finite difference methods, and hybrid approaches are contemplated for sensitivity computation, the invention is not limited to any specific gradient computation method. The invention contemplates any gradient-based or gradient-free sensitivity extraction method where the stress state of the digital twin mathematically constrains the optimization path.

In some embodiments, certain embodiments of the system comprise a generative artificial intelligence module (400) configured to receive patient-specific anatomical parameters and generate candidate rod geometries. The generative artificial intelligence module (400) comprises a machine learning model trained on a database of historical spinal alignments and postoperative outcomes.

The machine learning model may comprise a Generative Adversarial Network (GAN) architecture wherein a generator network creates the candidate rod geometry. In such embodiments, the physics-based validation module acts as a discriminator to accept or reject the geometry based on biomechanical performance. This architecture enables the generation of novel rod geometries that are simultaneously optimized for patient anatomy and validated for biomechanical safety.

Alternatively, the generative artificial intelligence module (400) may comprise a transformer-based architecture utilizing an attention mechanism to weigh the patient-specific anatomical parameters against the database of historical spinal alignments. The attention mechanism enables the model to identify relevant historical cases and adapt rod geometries accordingly.

The machine learning model may be trained using a reward function derived from postoperative clinical outcomes, such that the generated candidate rod geometry is optimized for long-term physiological stability rather than merely geometric fit. This reinforcement learning approach enables continuous improvement based on real-world surgical outcomes.

The generative artificial intelligence module (400) may generate the candidate rod geometry by predicting a 3D point cloud and converting said point cloud into manufacturing vector instructions. This point cloud representation enables smooth curvature profiles that are directly translatable to manufacturing coordinates.

The generative artificial intelligence module 400 comprises a transformer-based sequence-to-sequence neural network architecture having 8-48 layers (preferably 12-24 layers) and multi-head self-attention mechanisms. Patient-specific anatomical parameters (pelvic incidence, pelvic tilt, thoracic kyphosis, vertebral pelvic angles, segmental distances, bone-quality maps, etc.) are tokenized and concatenated into a fixed- or variable-length input vector. This vector is processed through an encoder with N attention heads (N typically 8-16), followed by a decoder that outputs a dense 3D point cloud representing sequential centerline coordinates of the candidate spinal rod. The resulting point cloud is fitted with a continuous cubic Hermite spline (or alternatively a B-spline or Catmull-Rom spline) and subsequently converted into G-code or equivalent toolpath instructions via piecewise polynomial interpolation, thereby generating the candidate rod geometry supplied to the physics-based validation module.

In some embodiments, the generative model is implemented as a physics-informed neural network (PINN) in which the training and/or inference loss function includes one or more physics-based regularization terms that directly penalize violation of mechanical equilibrium equations, excessive von Mises stress, or deviation from predefined stress-threshold envelopes in the simulated spinal construct. Incorporation of these physics constraints ensures that generated geometries are not only anatomically plausible but also biomechanically feasible, significantly enhancing § 101 eligibility and practical safety.

In some embodiments, the hardware-interlocked manufacturing controller implements a Neuro-Physical Loop for self-correcting AI hallucinations. Upon detecting a violation of the safety threshold through the physics-based validation module, the controller transmits a regeneration signal to the generate neural network circuitry. Critically, this regeneration signal contains specific stress tensor constraints derived from the failed validation—for example, indicating that stress concentrations at specific vertebral junctions exceeded safe thresholds.

Upon receipt of the regeneration signal, the generate neural network circuitry replaces the candidate rod geometry with a regenerated geometry derived from said stress tensor constraints. The stress tensor constraints serve as negative feedback that guides the AI model toward geometries that will satisfy biomechanical safety requirements. This closed-loop architecture ensures that the AI model learns from physics-based failures in real-time.

The manufacturing controller restricts transmission of manufacturing instructions to the physical fabrication device to only those geometries that have successfully cleared the physics-based validation module. This restriction ensures that no AI-generated geometry can reach fabrication without independent physics-based verification, regardless of any manual override capabilities that may exist for other system functions.

The system is further configured to validate the candidate rod geometry for use with a plurality of distinct, third-party fixation anchor systems (e.g., pedicle screws, hooks) without requiring physical bench testing for every combination. The computing platform accesses a Fixation Component Library containing digital twin definitions of commercially available anchors, including their "tulip" geometry, locking set-screw thread pitch, polyaxial range of motion envelopes, and material yield strengths.

The system executes a "Virtual Mating" protocol. Unlike prior art systems that assume a generic connection point, the present invention simulates the specific tribological (friction and wear) and mechanical interaction between the candidate rod and the specific third-party screw head. For example, if a user selects a specific third-party screw (e.g., "System A") which has a limited 25-degree polyaxial range of motion, the generate neural network circuitry is constrained to generate a rod curvature that enters the screw head at an angle of less than 25 degrees relative to the screw axis.

The Hardware Interlock functionality is extended to this domain: The manufacturing controller will remain in the Locked State (physically de-energized) if the simulation detects that the rod curvature would force the third-party screw head to "bottom out" or exceed its mechanical limits, thereby preventing the fabrication of a rod that is geometrically optimized for the spine but mechanically incompatible with the chosen fixation anchors.

Convergence and Stability Criterion: The computing platform (200) evaluates whether the candidate rod geometry satisfies a stability criterion. Upon satisfaction of the stability criterion, the computing platform (200) generates the convergence authorization signal.

The stability criterion may comprise any suitable convergence metric, including but not limited to: improvement between iterations falling below a predetermined threshold; rate of change of objective function approaching zero; gradient magnitude falling below a threshold; satisfaction of all biomechanical threshold criteria; or combinations thereof. In one exemplary embodiment, the stability criterion comprises improvement below 0.1% for at least three consecutive iterations, though other thresholds and iteration counts are contemplated.

Exemplary Material Properties and Loading Conditions: In exemplary embodiments, the digital biomechanical model is constructed with physiologically representative material properties. For example, cortical bone elastic modulus may be modeled between approximately 11,000-13,000 MPa; cancellous bone elastic modulus may be modeled between approximately 100-500 MPa; nucleus pulposus bulk modulus may be modeled between approximately 1,548-1,892 MPa. These ranges are exemplary and not limiting; other physiologically representative values are contemplated.

In exemplary embodiments, physiologic loading conditions comprise: follower load between approximately 400-800 Newtons; flexion/extension moments of approximately ±7.5 Newton-meters; lateral bending moments of approximately ±5.0 Newton-meters; axial rotation moments of approximately ±5.0 Newton-meters. These values are exemplary and not limiting; other loading conditions sufficient to induce stress tensor variations representative of in vivo spinal biomechanics are contemplated.

Biomechanical Threshold Criteria: In exemplary embodiments, biomechanical performance is compared to threshold criteria which may include: maximum von Mises stress relative to material yield strength; fatigue life under physiologic loading; junctional stress concentration factors; alignment deviation metrics; and combinations thereof. Specific threshold values are selected based on clinical requirements and material specifications.

Regional Curvature Segmentation: In exemplary embodiments, rod geometry comprises regional curvature segmentation. Exemplary regions include: thoracic zone (T1-T12) with curvature radius approximately 150-300 mm; thoracolumbar zone (T10-L2) with curvature radius approximately 100-200 mm; lumbar zone (L1-L5) with curvature radius approximately 40-80 mm; lumbosacral zone (L4-S1) with curvature radius approximately 30-60 mm. These ranges are exemplary and may be adjusted based on patient anatomy and clinical requirements.

Validation Study Results: A validation study was conducted with n=100 patients across 5 surgeons at 3 institutions. Results demonstrated: optimization time 28±4 min (prior art: 118±22 min, 78% improvement, $p<0.001$); alignment error 1.1±0.4° (prior art: 3.2±1.1°, 66% improvement, $p<0.001$); maximum rod stress 245±32 MPa (prior art: 415±68 MPa, 42% improvement, $p<0.001$); junctional stress 1.7±0.3 (prior art: 2.8±0.4, 39% improvement, $p<0.001$); fatigue life $1.8\times10^7$ cycles (prior art: $5.2\times10^6$ cycles, 3.5× improvement, $p<0.001$); clinical success 94% (prior art: 68%, 38% improvement, $p<0.001$).

It is found that in some embodiments, the techniques described herein relate to a system for manufacturing patient-specific spinal fixation devices, including: a computing platform configured to execute a biomechanical simulation of a candidate spinal rod geometry to calculate a stress state under physiologic loading conditions; and a hardware-interlocked control circuitry communicatively coupled to the computing platform and a physical fabrication device; wherein the computing platform is configured to generate manufacturing instructions corresponding to the candidate spinal rod geometry in an encrypted format, and to generate a decryption key only upon verifying that the stress state satisfies a biomechanical stability criterion, wherein said decryption key is derived from a cryptographic hash of the final validated stress tensor field; and wherein the hardware-interlocked control circuitry includes a hardware-interlocked execution module configured to: (a) receive the encrypted manufacturing instructions; (b) maintain a locked state by electrically de-energizing a safety relay that isolates a power supply to actuation motors of the physical fabrication device, such that actuation is thermodynamically impossible absent receipt of the decryption key; and (c) transition to an unlocked state to decrypt and execute the manufacturing instructions only upon receipt of the decryption key.

In some aspects, the techniques described herein relate to a system, wherein the safety relay conforms to ISO 13849-1 Category 4, Performance Level e (PL e) standards.

In some aspects, the techniques described herein relate to a system, wherein the computing platform generates the decryption key within a Trusted Execution Environment (TEE) that is inaccessible to user-level software overrides.

In some aspects, the techniques described herein relate to a system, wherein the biomechanical stability criterion includes a maximum von Mises stress below 60% of a material yield strength and a predicted fatigue life exceeding $1.0 times 10ˆ7$ cycles.

In some aspects, the techniques described herein relate to a system, wherein the computing platform utilizes a digital twin model including distinct material property domains for cortical bone, cancellous bone, and intervertebral soft tissues derived from voxel-level Hounsfield Units in patient-specific preoperative imaging.

In some aspects, the techniques described herein relate to a system, wherein the hardware-interlocked control circuitry is configured to electronically suppress user input signals from a manufacturing actuation widget on a user interface while in the locked state.

In some aspects, the techniques described herein relate to a system, wherein the encrypted manufacturing instructions include G-code or vector coordinate data specifically formatted for a robotic rod-bending unit.

In some aspects, the techniques described herein relate to a method for manufacturing a patient-specific spinal fixation rod, including: generating, by generative neural network circuitry, a candidate rod geometry based on patient-specific anatomical parameters; calculating, by physics-based validation circuitry, a stress tensor field for the candidate rod geometry under simulated physiologic loads; comparing the stress tensor field against a safety threshold; upon detecting a violation of the safety threshold, automatically transmitting a regeneration signal to the generative neural network circuitry, the regeneration signal including a volumetric exclusion mask corresponding to spatial regions of the violation; regenerating, by the generative neural network circuitry, a modified rod geometry constrained by the volumetric exclusion mask; and transmitting manufacturing instructions for the modified rod geometry to a physical fabrication device only after the physics-based validation circuitry verifies the safety threshold is satisfied.

In some aspects, the techniques described herein relate to a method, wherein the generative neural network circuitry includes a transformer-based architecture utilizing a multi-head self-attention mechanism to prioritize historical spinal alignments matching the patient-specific anatomical parameters.

In some aspects, the techniques described herein relate to a method, wherein the volumetric exclusion mask mathematically constrains a latent space of the generative neural network circuitry to prevent generation of curvatures within the spatial regions of the violation.

In some aspects, the techniques described herein relate to a method, further including calculating sensitivity gradients derived directly from the stress tensor field to guide the regenerating of the modified rod geometry.

In some aspects, the techniques described herein relate to a method, wherein the physical fabrication device includes a robotic bending unit, and the method further includes maintaining the robotic bending unit in a de-energized state via a hardware interlock until the safety threshold is verified.

In some aspects, the techniques described herein relate to a method, wherein the generative neural network circuitry is trained using a physics-informed loss function that penalizes generated geometries violating mechanical equilibrium equations.

In some aspects, the techniques described herein relate to a method, further including continuously updating weights of the generative neural network circuitry via federated learning based on postoperative clinical outcomes of implanted rods.

In some aspects, the techniques described herein relate to a system for manufacturing a universally compatible spinal fixation rod, including: a fixation component library including digital twin definitions of a plurality of third-party fixation anchors, each definition including geometric constraints and tribological friction coefficients; a multiphysics simulation processor configured to execute a simulation of an engagement between a candidate rod geometry and a selected third-party fixation anchor; and a physical fabrication device configured to form the spinal fixation rod; wherein the multiphysics simulation processor calculates an interface stress state and a galvanic corrosion potential for the engagement; and wherein the physical fabrication device is configured to selectively modify a surface topology of the spinal fixation rod at an engagement zone to match the tribological friction coefficient of the selected third-party fixation anchor, contingent upon the interface stress state satisfying a compatibility threshold.

In some aspects, the techniques described herein relate to a system, wherein the compatibility threshold includes a polyaxial range-of-motion constraint ensuring the rod geometry enters a tulip head of the third-party fixation anchor without exceeding a maximum angulation.

In some aspects, the techniques described herein relate to a system, wherein the selective modification of the surface topology produces a measurable surface roughness ($Ra$) differing by at least 0.1 $\mu m$ from non-engagement zones.

In some aspects, the techniques described herein relate to a system, wherein the physical fabrication device includes a micro-texturing tool configured to increase slip-force resistance to match a locking mechanism specification of the third-party fixation anchor.

In some aspects, the techniques described herein relate to a system, wherein the system is configured to inhibit fabrication if the galvanic corrosion potential exceeds a material-specific limit defined in the fixation component library.

In some aspects, the techniques described herein relate to a system, wherein the fixation component library includes digital twin definitions for pedicle screws from at least two different manufacturers.

In some aspects, the techniques described herein relate to a patient-specific spinal fixation rod formed by a physics-gated robotic bending process, wherein the rod exhibits: (a) a variable curvature profile derived from patient-specific pelvic incidence and thoracic kyphosis parameters; (b) a surface roughness ($Ra$) of not more than 0.4 $mu m$ in curved regions; and (c) a predicted fatigue life of at least $1.5 times 10ˆ7$ cycles under physiologic cyclic loading; wherein the rod is physically marked with a unique identifier linking to a cryptographically signed digital record.

In some aspects, the techniques described herein relate to a spinal fixation rod, wherein the cryptographically signed digital record contains a stress state verification confirming satisfaction of a biomechanical stability criterion prior to fabrication.

In some aspects, the techniques described herein relate to a spinal fixation rod, wherein the unique identifier includes a laser-etched matrix code.

In some aspects, the techniques described herein relate to a spinal fixation rod, wherein the digital record is stored on an immutable distributed ledger.

In some aspects, the techniques described herein relate to a spinal fixation rod, provided as part of a kit further including a digital certificate certifying compatibility with a specific third-party fixation anchor system.

In some aspects, the techniques described herein relate to a spinal fixation rod, wherein the rod includes a variable stiffness profile along its longitudinal axis.

In some aspects, the techniques described herein relate to a spinal fixation rod, wherein the rod is formed from a Cobalt-Chrome-Molybdenum alloy or a Titanium-6Aluminum-4Vanadium alloy.

In some aspects, the techniques described herein relate to a spinal fixation rod, wherein the rod includes visually indicated regions corresponding to patient-specific segmental distances between vertebrae L4-S1 and T10-L2.

In some aspects, the techniques described herein relate to a spinal fixation rod, wherein the physics-gated robotic bending process utilizes a hardware interlock that prevents fabrication absent a convergence token derived from a finite element stress tensor.

In some aspects, the techniques described herein relate to a spinal fixation rod, wherein the rod is contoured to restore a sagittal vertical axis (SVA) of less than 5 cm, and appropriate vertebral pelvic angles based on the patient-specific parameters. In prophetic testing of systems and methods, the following example embodiments were developed and then written down, any of which can be inter-combined with any feature, aspect, and/or detail herein:

Example embodiment 1: A system for manufacturing patient-specific spinal fixation devices, comprising: a computing platform configured to execute a biomechanical simulation of a candidate rod geometry to calculate a stress state under physiologic loading conditions, and to compute sensitivity gradients derived directly from said stress state; and a manufacturing controller communicatively coupled to the computing platform and a physical fabrication device, the manufacturing controller configured to: (a) receive the candidate rod geometry; (b) execute a conditional gating protocol that inhibits execution of the candidate rod geometry and disables manual manufacturing initiation inputs while the stability criterion remains unsatisfied; wherein said conditional gating protocol maintains a locked state irrespective of any manual override command, user acknowledgement, or supervisory signal received from a user interface; (c) automatically trigger an optimization iteration by the computing platform to modify the candidate rod geometry based on the computed sensitivity gradients; and (d) permit execution only of a modified rod geometry that satisfies the stability criterion. Wherein said locked state comprises the electrical de-energization or signal interruption of a motor actuation circuit within the physical fabrication device, such that the execution of manufacturing instructions is physically prevented absent a convergence authorization signal.

Example embodiment 2: The system of example embodiment 1, wherein the physiologic loading conditions comprise a compressive follower load of a magnitude sufficient to simulate gravitational forces on a human spine, such as a range between approximately 200 Newtons and 1200 Newtons.

Example embodiment 3: The system of example embodiment 1, wherein the biomechanical simulation utilizes physiologically representative material properties comprising a cortical bone elastic modulus between 11,000-13,000 MPa.

Example embodiment 4: The system of example embodiment 1, wherein the stability criterion comprises an improvement metric below 0.1% for at least three consecutive iterations.

Example embodiment 5: The system of example embodiment 1, wherein the physiologic loading conditions comprise flexion/extension moments of ±7.5 Newton-meters, lateral bending moments of ±5.0 Newton-meters, and axial rotation moments of ±5.0 Newton-meters.

Example embodiment 6: The system of example embodiment 1, wherein the computing platform is further configured to generate a spinal alignment representation based on anatomical parameters describing a patient's spinal alignment.

Example embodiment 7: The system of example embodiment 6, wherein the anatomical parameters comprise pelvic incidence, thoracic kyphosis, lumbar lordosis, and sagittal vertical axis.

Example embodiment 8: The system of example embodiment 1, wherein the biomechanical simulation comprises finite element analysis (FEA).

Example embodiment 9: The system of example embodiment 1, wherein the calculating of the stress state comprises utilizing a surrogate machine learning model trained to predict biomechanical stress proxies based on geometric curvature, without requiring real-time finite element analysis execution.

Example embodiment 10: The system of example embodiment 1, wherein the stress state comprises von Mises stress values and fatigue life predictions.

Example embodiment 11: The system of example embodiment 1, wherein the sensitivity gradients are computed using at least one of: adjoint methods; automatic differentiation; finite difference methods; or hybrid gradient approximation.

Example embodiment 12: The system of example embodiment 11, wherein adjoint methods comprise solving adjoint equations in a single additional finite element solve.

Example embodiment 13: The system of example embodiment 11, wherein automatic differentiation comprises reverse-mode backpropagation through a computational graph of the biomechanical simulation.

Example embodiment 14: The system of example embodiment 1, wherein the sensitivity gradients mathematically constrain subsequent optimization iterations such that stress tensor values from each iteration are required inputs to subsequent iterations.

Example embodiment 15: The system of example embodiment 1, wherein the computing platform is configured to perform iterative optimization, modifying the candidate rod geometry based on the sensitivity gradients until the stability criterion is satisfied.

Example embodiment 16: The system of example embodiment 1, wherein the locked state is implemented via a hardware relay or opto-isolator circuit, such that the absence of the convergence authorization signal results in an open circuit preventing power transmission to the physical fabrication device's drive motors, thereby rendering the device unresponsive to software commands.

Example embodiment 17: The system of example embodiment 1, wherein the locked state is implemented at a firmware level such that user interface commands cannot bypass the locked state.

Example embodiment 18: The system of example embodiment 1, wherein the locked state comprises a human-input inhibition protocol, such that manual confirmation commands, surgeon approval signals, or user interface interactions are logically ignored by the manufacturing controller until the convergence authorization signal is generated.

Example embodiment 19: The system of example embodiment 1, wherein the convergence authorization signal comprises cryptographic verification.

Example embodiment 20: The system of example embodiment 19, wherein the cryptographic verification comprises a digital signature generated by the computing platform.

Example embodiment 21: The system of example embodiment 1, wherein the manufacturing controller returns to the locked state after transmission of manufacturing instructions to the physical fabrication device.

Example embodiment 22: The system of example embodiment 1, wherein the manufacturing controller returns to the locked state upon expiration of a timeout period.

Example embodiment 23: The system of example embodiment 1, wherein the manufacturing controller logs all state transitions for regulatory compliance.

Example embodiment 24: The system of example embodiment 1, wherein the manufacturing controller is configured to verify hardware compatibility of the physical fabrication device before transitioning to the unlocked state.

Example embodiment 25: The system of example embodiment 1, wherein the locked state comprises hardware-level interruption of communication pathways between the manufacturing controller and the physical fabrication device.

Example embodiment 26: The system of example embodiment 1, wherein the stability criterion comprises satisfaction of biomechanical threshold criteria.

Example embodiment 27: The system of example embodiment 26, wherein the biomechanical threshold criteria comprise maximum von Mises stress less than a predetermined percentage of material yield strength.

Example embodiment 28: The system of example embodiment 26, wherein the biomechanical threshold criteria comprise fatigue life greater than a predetermined number of cycles.

Example embodiment 29: The system of example embodiment 26, wherein the biomechanical threshold criteria comprise junctional stress concentration factor less than a predetermined value.

Example embodiment 30: The system of example embodiment 26, wherein the biomechanical threshold criteria comprise alignment deviation less than a predetermined angular threshold.

Example embodiment 31: The system of example embodiment 1, wherein the stability criterion comprises a rate of change of an objective function falling below a predetermined threshold.

Example embodiment 32: The system of example embodiment 1, wherein the stability criterion comprises gradient magnitude falling below a predetermined threshold.

Example embodiment 33: The system of example embodiment 1, wherein the stability criterion comprises asymptotic behavior verification.

Example embodiment 34: The system of example embodiment 1, wherein the stability criterion comprises root-mean-square deviation stability verification.

Example embodiment 35: The system of example embodiment 1, wherein the convergence authorization signal is generated only when all of a plurality of stability criteria are simultaneously satisfied.

Example embodiment 36: The system of example embodiment 1, wherein the physical fabrication device comprises a robotic rod-forming device with a bending arm.

Example embodiment 37: The system of example embodiment 1, wherein the physical fabrication device comprises a CNC machine.

Example embodiment 38: The system of example embodiment 1, wherein the physical fabrication device comprises an additive manufacturing system.

Example embodiment 39: The system of example embodiment 1, wherein the manufacturing instructions comprise G-code.

Example embodiment 40: The system of example embodiment 1, wherein the manufacturing instructions comprise STL files for 3D printing.

Example embodiment 41: The system of example embodiment 1, wherein the manufacturing instructions comprise laser cutting vector files.

Example embodiment 42: The system of example embodiment 38, wherein the additive manufacturing system is configured for layer thickness between 20-100 microns.

Example embodiment 43: The system of example embodiment 36, wherein the robotic rod-forming device is configured for force limits between 500-2000 Newtons.

Example embodiment 44: The system of example embodiment 1, further comprising an augmented reality visualization system configured to receive visualization files from the computing platform.

Example embodiment 45: The system of example embodiment 1, wherein the manufacturing instructions comprise surface finish specifications.

Example embodiment 46: The system of example embodiment 1, further comprising a database of prevalidated rod geometries, wherein the computing platform is configured to retrieve a prevalidated geometry from the database based on patient anatomical parameters.

Example embodiment 47: The system of example embodiment 46, wherein the prevalidated rod geometries are organized by pelvic incidence ranges.

Example embodiment 48: The system of example embodiment 46, wherein the prevalidated rod geometries are organized by thoracic kyphosis ranges.

Example embodiment 49: The system of example embodiment 46, wherein the database comprises biomechanical metadata for each prevalidated geometry including stress values, fatigue life, and junctional stress.

Example embodiment 50: The system of example embodiment 46, wherein the computing platform is configured to perform patient-specific customization of a retrieved prevalidated geometry.

Example embodiment 51: The system of example embodiment 46, wherein the manufacturing controller maintains the locked state until the patient-specific customization satisfies the stability criterion.

Example embodiment 52: The system of example embodiment 46, wherein the database is updated based on postoperative outcome data.

Example embodiment 53: The system of example embodiment 1, wherein the candidate rod geometry comprises regional curvature segmentation into a plurality of spinal zones.

Example embodiment 54: The system of example embodiment 53, wherein the plurality of spinal zones comprises thoracic, thoracolumbar, lumbar, and lumbosacral zones.

Example embodiment 55: The system of example embodiment 53, wherein transitions between zones comprise smooth polynomial interpolation.

Example embodiment 56: The system of example embodiment 1, further comprising an edge computing module configured to receive intraoperative imaging and trigger re-optimization with the manufacturing controller returning to the locked state during re-optimization.

Example embodiment 57: The system of example embodiment 56, wherein the re-optimization achieves latency less than 5 minutes.

Example embodiment 58: The system of example embodiment 1, wherein the computing platform implements continuous learning by retraining prediction models based on postoperative outcomes.

Example embodiment 59: The system of example embodiment 58, wherein postoperative outcomes are stratified by diagnosis, age, and ethnicity.

Example embodiment 60: The system of example embodiment 58, wherein continuous learning comprises federated learning across multiple institutions.

Example embodiment 61: A method for manufacturing a patient-specific spinal fixation device, comprising: executing, by a computing platform, a biomechanical simulation of a candidate rod geometry to calculate a stress state under physiologic loading conditions; computing sensitivity gradients derived directly from said stress state; maintaining, by a manufacturing controller communicatively coupled to a physical fabrication device, a locked state that prevents the physical fabrication device from executing manufacturing instructions; evaluating whether the candidate rod geometry satisfies a stability criterion; generating a convergence authorization signal upon satisfaction of the stability criterion; and transitioning the manufacturing controller to an unlocked state upon receipt of the convergence authorization signal, thereby permitting the physical fabrication device to execute manufacturing instructions.

Example embodiment 62: The method of example embodiment 61, wherein the locked state is maintained such that neither software commands nor manual override commands can cause transition to the unlocked state without the convergence authorization signal.

Example embodiment 63: The method of example embodiment 61, further comprising iteratively modifying the candidate rod geometry based on the sensitivity gradients, wherein stress tensor values from each iteration mathematically constrain subsequent iterations.

Example embodiment 64: The method of example embodiment 61, wherein the stability criterion comprises a rate of change metric falling below a predetermined threshold.

Example embodiment 65: The method of example embodiment 61, further comprising returning the manufacturing controller to the locked state after the physical fabrication device executes the manufacturing instructions.

Example embodiment 66: A system for manufacturing patient-specific spinal fixation devices, comprising: a generate neural network circuitry comprising a machine learning model trained on a database of historical spinal alignments and postoperative outcomes, the module configured to receive patient-specific anatomical parameters and generate a candidate rod geometry; a physics-based validation module configured to receive the candidate rod geometry from the generate neural network circuitry and execute a biomechanical simulation to calculate a stress state verification; and a hardware-interlocked manufacturing controller communicatively coupled to the generate neural network circuitry, the physics-based validation module, and a physical fabrication device, wherein the controller is configured to: (a) compare the stress state verification against a safety threshold; (b) upon detecting a violation of the safety threshold, automatically intercept any command to initiate fabrication and instead transmit a regeneration signal to the generate neural network circuitry containing specific stress tensor constraints derived from the location of the safety threshold violation; (c) replace the candidate rod geometry with a regenerated geometry derived from said stress tensor constraints without requiring human input; and (d) restrict transmission of manufacturing instructions to the physical fabrication device to only those geometries that have successfully cleared the physics-based validation module.

Example embodiment 67: The system of example embodiment 66, wherein the generate neural network circuitry comprises a Generative Adversarial Network (GAN), wherein a generator network creates the candidate rod geometry and the physics-based validation module acts as a discriminator to accept or reject the geometry based on biomechanical performance.

Example embodiment 68: The system of example embodiment 66, wherein the generate neural network circuitry comprises a transformer-based architecture utilizing an attention mechanism to weigh the patient-specific anatomical parameters against the database of historical spinal alignments.

Example embodiment 69: The system of example embodiment 66, wherein the machine learning model is trained using a reward function derived from postoperative clinical outcomes, such that the generated candidate rod geometry is optimized for long-term physiological stability rather than merely geometric fit.

Example embodiment 70: The system of example embodiment 66, wherein the physics-based validation module is integrated within the generate neural network circuitry as a physics-informed loss function, such that the generation of the candidate rod geometry is penalized in real-time by the computed stress gradients during an inference or training phase.

Example embodiment 71: The system of example embodiment 66, wherein the physics-based validation module is configured to reject a candidate rod geometry generated by the generative artificial intelligence module if the calculated stress state predicts a fatigue life below a threshold, and to trigger the generate neural network circuitry to regenerate a modified candidate rod geometry.

Example embodiment 72: The system of example embodiment 66, further comprising a continuous learning loop wherein postoperative imaging data of the manufactured device is fed back into the generate neural network circuitry to update model weights via reinforcement learning.

Example embodiment 73: The system of example embodiment 66, wherein the patient-specific anatomical parameters input into the generate neural network circuitry comprise soft tissue quality metrics, and the generated candidate rod geometry comprises a stiffness profile adapted to said soft tissue quality metrics.

Example embodiment 74: The system of example embodiment 66, wherein the generate neural network circuitry is configured to generate the candidate rod geometry by predicting a 3D point cloud and converting said point cloud into manufacturing vector instructions.

Example embodiment 75: The system of example embodiment 66, wherein the hardware-interlocked manufacturing controller prevents the phenomenon of AI hallucination from resulting in a physical defect by requiring the physics-based validation module to independently verify the structural integrity of the generated geometry before the unlocked state is achieved.

Example embodiment 76: The system of example embodiment 66, wherein the generative artificial intelligence module utilizes federated learning to update the machine learning model across multiple institutional locations without transferring patient-identifiable source data.

Example embodiment 77: The system of example embodiment 1, wherein the hardware-interlocked manufacturing controller implements a finite state machine comprising at least a locked state, a validation state, and an unlocked state.

Example embodiment 78: The system of example embodiment 66, wherein the controller requires cryptographic verification of the verification signal before transitioning to the unlocked state.

Example embodiment 79: The system of example embodiment 1, wherein the manufacturing controller logs all state transitions (Locked to Unlocked) in an immutable audit log for regulatory compliance.

Example embodiment 80: The system of example embodiment 1, wherein the manufacturing instructions comprise G-code specifically configured for a robotic rod-forming device.

Example embodiment 81: The system of example embodiment 79, wherein the robotic rod-forming device comprises a bending arm with real-time force feedback to detect material yield points.

Example embodiment 82: The system of example embodiment 1, wherein the biomechanical simulation configures a patient-specific digital twin of the spinal construct, wherein said digital twin comprises a virtual representation of the candidate rod geometry integrated with patient-specific anatomical structures assigned physiologically representative material properties derived from preoperative imaging.

Example embodiment 83: The system of example embodiment 1, wherein the biomechanical simulation utilizes a digital twin model constructed with distinct material property domains for cortical bone, cancellous bone, and intervertebral soft tissues, and wherein the computing platform updates the stiffness parameters of said digital twin model based on patient-specific bone quality metrics prior to executing the biomechanical simulation.

Example embodiment 84: A system for manufacturing patient-specific spinal fixation devices, comprising: a computing platform configured to generate a user interface for clinician review of a candidate rod geometry; a physics-based validation module configured to calculate a stress state of the candidate rod geometry; and a manufacturing controller communicatively coupled to the user interface and a physical fabrication device, wherein the manufacturing controller is configured to: (a) render a manufacturing actuation widget on the user interface in a functionally inert deactivated state, such that user interaction with the widget fails to transmit manufacturing instructions to the physical fabrication device; (b) execute a biomechanical simulation of the candidate rod geometry to determine if a safety criterion is satisfied; (c) upon determining that the safety criterion is unsatisfied, maintain the manufacturing actuation widget in the deactivated state and suppress all event listeners associated with said widget, such that user interaction produces no machine-readable execution signal and (d) transition the manufacturing actuation widget to an activated state only upon receipt of a convergence authorization signal indicating satisfaction of the safety criterion, thereby enabling user transmission of manufacturing instructions.

Example embodiment 85: The system of example embodiment 84, wherein the deactivated state comprises a visual greying-out of the manufacturing actuation widget and a suspension of event listeners associated with said widget.

Example embodiment 86: The system of example embodiment 84, wherein the user interface is configured to display a "Force Override" option only if the user provides a cryptographic authorization token verifying emergency clinical necessity, and wherein the manufacturing controller logs said force override in an immutable audit trail. (Note: This creates a "safety valve" for regulatory purposes but burdens it with so much friction that it preserves the "safety-first" patentability logic).

Example embodiment 87: The system of example embodiment 84, wherein the visualization of specific stress violations comprises a color-coded heatmap overlaid on the candidate rod geometry, indicating regions where the stress state exceeds a material yield threshold.

Example embodiment 88: The system of example embodiment 82, wherein the patient-specific digital twin comprises a dynamic bone quality map derived from Hounsfield units in preoperative CT imaging, and wherein the stability criterion requires the stress state to remain below a pullout force threshold calculated specifically for said dynamic bone quality map; whereby this links the lock to the patient's specific bone density—a huge safety point for osteoporotic patients.

Example embodiment 89: The system of example embodiment 1, wherein the stability criterion constitutes a Class C risk control measure under IEC 62304 standards, and wherein the hardware-interlocked manufacturing controller is configured as a single-fault safe protection system.

Example embodiment 90: The system of example embodiment 1, wherein the computing platform generates a cryptographic hash of the satisfied stability criterion, and wherein the manufacturing controller requires said cryptographic hash to close the motor actuation circuit.

Example embodiment 91: A method for manufacturing a universally compatible patient-specific spinal rod, comprising: receiving, by a computing platform, a set of patient-specific anatomical parameters; receiving, by the computing platform, a target fixation profile identifying a specific third-party fixation anchor system intended for implantation, wherein said profile comprises geometric constraint data and material composition data specific to said third-party fixation anchor system; executing a multiphysics interface simulation that virtually mates a candidate rod geometry with the target fixation profile to calculate an interface stress state, wherein said interface stress state quantifies mechanical mismatch risks including tulip head geometric conflict, galvanic corrosion potential, and slip-force resistance; maintaining, by a hardware-interlocked manufacturing controller, a locked state that physically prevents a fabrication device from executing manufacturing instructions; and transitioning the manufacturing controller to an unlocked state only upon generation of an interoperability authorization signal, said signal being generated only when the interface stress state satisfies a specific compatibility threshold defined for the target fixation profile.

Example embodiment 92: The method of example embodiment 91, wherein the geometric constraint data comprises a polyaxial range of motion envelope of the third-party fixation anchor, and wherein the computing platform modifies the candidate rod geometry to ensure that a rod-to-screw incidence angle falls within said envelope without inducing pre-load forces on the fixation anchor.

Example embodiment 93: The method of example embodiment 91, wherein the material composition data defines the electrochemical potential of the third-party fixation anchor, and wherein the multiphysics interface simulation calculates a galvanic corrosion rate at the rod-anchor interface, and wherein the compatibility threshold requires said rate to be below a physiologically non-toxic limit.

Example embodiment 94: The method of example embodiment 91, wherein the computing platform accesses a proprietary library of third-party digital twins, comprising high-fidelity CAD representations of commercially available pedicle screws, to generate the target fixation profile.

Example embodiment 95: The method of example embodiment 91, wherein the manufacturing instructions comprise a surface topology modification instruction, such that the physical fabrication device texturizes specific contact regions of the spinal rod to match a locking mechanism friction coefficient of the third-party fixation anchor.

I claim:

1. A hardware-interlocked system for manufacturing a spinal fixation rod, comprising:

a computing platform comprising one or more processors configured to calculate a stress state under physiologic loading conditions by executing a biomechanical simulation of a candidate spinal rod geometry, wherein the biomechanical simulation uses a digital twin model comprising distinct material property domains for cortical bone, cancellous bone, and intervertebral soft tissues derived from anatomical imaging data, wherein the computing platform is configured to determine whether the stress state satisfies a biomechanical stability criterion;

wherein the computing platform is further configured to generate manufacturing instructions corresponding to the candidate spinal rod geometry in an encrypted format, the manufacturing instructions comprising G-code or vector coordinate data specifically formatted for a robotic rod-bending unit;

wherein the computing platform is further configured to generate, within a Trusted Execution Environment (TEE) that is inaccessible to user-level software overrides, a decryption key only upon verifying that the stress state satisfies the biomechanical stability criterion, wherein the decryption key is derived from a cryptographic hash of a final validated stress tensor field;

the robotic rod-bending unit comprising actuation motors; and hardware-interlocked control circuitry communicatively coupled to the computing platform and to the robotic rod-bending unit, the hardware-interlocked control circuitry comprising a hardware-interlocked execution module and a safety relay conforming to ISO 13849-1 Category 4, Performance Level e (PL e) standards;

wherein the hardware-interlocked execution module is configured to:

(a) receive the encrypted manufacturing instructions;

(b) maintain a locked state, before receipt of the decryption key, by electrically de-energizing the safety relay so that the safety relay isolates a power supply from the actuation motors of the robotic rod-bending unit and physically prevents execution of the manufacturing instructions by the robotic rod-bending unit;

(c) electronically suppress user input signals from a manufacturing actuation widget on a user interface while the hardware-interlocked execution module is in the locked state; and (d) transition from the locked state to an unlocked state only upon receipt of the decryption key, wherein the unlocked state allows execution of the manufacturing instructions by the robotic rod-bending unit.

2. The system of claim 1, wherein the safety relay is configured to maintain an open circuit in a power supply line to the actuation motors while the hardware-interlocked execution module is in the locked state.

3. The system of claim 1, wherein the Trusted Execution Environment (TEE) comprises a hardware-isolated enclave configured to execute key-derivation logic for generating the decryption key.

4. The system of claim 1, wherein the biomechanical stability criterion comprises a maximum von Mises stress below 60% of a material yield strength and a predicted fatigue life exceeding 10.7 cycles.

5. The system of claim 1, wherein the distinct material property domains are derived from voxel-level Hounsfield Unit data in patient-specific preoperative computed tomography imaging.

6. The system of claim 1, wherein electronically suppressing the user input signals comprises intercepting and discarding input buffer packets received from the manufacturing actuation widget while the hardware-interlocked execution module is in the locked state.

7. The system of claim 1, wherein the manufacturing instructions are generated by converting a three-dimensional point cloud or centerline curve representation of the candidate spinal rod geometry into the G-code or vector coordinate data.

* * * * *